US009062072B2

(12) United States Patent
Van Meir et al.

(10) Patent No.: US 9,062,072 B2
(45) Date of Patent: Jun. 23, 2015

(54) INHIBITORS OF HIF AND ANGIOGENESIS

(75) Inventors: Erwin G. Van Meir, Tucker, GA (US); Binghe Wang, Marietta, GA (US)

(73) Assignees: Emory University, Atlanta, GA (US); Georgia State University Research Foundation, Atlanta, GA (US)

( * ) Notice: Subject to any disclaimer, the term of this patent is extended or adjusted under 35 U.S.C. 154(b) by 263 days.

(21) Appl. No.: 13/642,836

(22) PCT Filed: Apr. 20, 2011

(86) PCT No.: PCT/US2011/033230
§ 371 (c)(1),
(2), (4) Date: Jan. 25, 2013

(87) PCT Pub. No.: WO2011/133659
PCT Pub. Date: Oct. 27, 2011

(65) Prior Publication Data
US 2013/0116275 A1 May 9, 2013

Related U.S. Application Data

(60) Provisional application No. 61/326,039, filed on Apr. 20, 2010.

(51) Int. Cl.
| | | |
|---|---|---|
| *A61K 31/44* | (2006.01) | |
| *A61K 31/47* | (2006.01) | |
| *A61K 31/35* | (2006.01) | |
| *A61K 31/34* | (2006.01) | |
| *C07D 491/052* | (2006.01) | |
| *C07D 215/12* | (2006.01) | |
| *C07D 307/81* | (2006.01) | |
| *C07D 311/04* | (2006.01) | |
| *C07D 405/12* | (2006.01) | |
| *C07D 311/58* | (2006.01) | |

(52) U.S. Cl.
CPC .......... *C07D 491/052* (2013.01); *C07D 215/12* (2013.01); *C07D 307/81* (2013.01); *C07D 311/04* (2013.01); *C07D 405/12* (2013.01); *C07D 311/58* (2013.01)

(58) Field of Classification Search
None
See application file for complete search history.

(56) References Cited

U.S. PATENT DOCUMENTS

| 7,652,033 B2 | 1/2010 | Van Meir et al. |
| 8,071,795 B2 | 12/2011 | Van Meir et al. |
| 2013/0164218 A1 | 6/2013 | Mun et al. |

FOREIGN PATENT DOCUMENTS

| WO | 2004/087066 | 10/2004 |
| WO | 2007/025169 | 3/2007 |
| WO | 2007/136592 | 11/2007 |
| WO | WO 2007/136592 | * 11/2007 |
| WO | 2008/113006 | 9/2008 |
| WO | 2008/136756 | 11/2008 |
| WO | 2010/006184 | 1/2010 |
| WO | 2010/006189 | 1/2010 |
| WO | 2010/039977 | 4/2010 |

OTHER PUBLICATIONS

Mooring et al (J Med Chem 54:8471-8489, 2011).*
Yin et al., Arylsulfonamide KCN1 inhibits in vivo glioma growth and interferes with HIF signaling by disrupting HIF-1a interaction with cofactors p300/CBP, Clin Cancer Res. 2012, 18(24):6623-33.
Tan et al., Identification of a novel small-molecule inhibitor of the hypoxia-inducible factor 1 pathway. Cancer Res. 2005, 65(2):605-12.
Burroughs, Design and Synthesis of HIF-1 Inhibitors as Anticancer Therapeutics, Dissertation, Georgia State University, 2013. http://scholarworks.gsu.edu/chemistry_diss/78.
Gundla, Discovery of Novel Small-Molecule Inhibitors of Human Epidermal Growth Factor Receptor-2: Combined Ligand and Target-Based Approach, J. Med. Chem. 2008, 51, 3367-3377.
Narita et al. Identification of a novel small molecule HIF-1alpha translation inhibitor, Clin Cancer Res. 2009,15 (19):6128-36.
Tan et al. Sulfonamides as a New Scaffold for Hypoxia Inducible Factor Pathway Inhibitors, Bioorg Med Chem Lett. 2011, 21(18): 5528-5532.
Patani Bioisosterism: A Rational Approach in Drug Design, Chem. Rev. 1996, 96, 3147-3176.
Lee et al. Acriflavine inhibits HIF-1 dimerization, tumor growth, and vascularization, PNAS, 2009, 106(42):17910-17915.
Mun, et al., (2012), "Structure-Activity Relationship of 2,2-Dimethyl-2H-Chromene Based Arylsulfonamide Analogs of 3,4-Dimethoxy-N-[(2,2-Dimethyl-2H-Chromen-6-y1)Methy1]-N-Phenylbenzenesulfonamide, a Novel Small Molecule Hypoxia Inducible Factor-1 (HIF-1) Pathway Inhibitor and Anti-Cancer Agent.", Bioorganic & Medicinal Chemistry, 20 (14): 4590-4597.
Mun, et al., (2012), "Design and in Vitro Activities of N-Alkyl-N-[(8-R-2,2-dimethyl-2H-Chromen-6-y1)Methyl] Heteroarylsulfonamides, Novel, Small-Molecule Hypoxia Inducible Factor-1 Pathway Inhibitors and Anticancer Agents.", Journal of Medicinal Chemistry, 55(15): 6738-6750.
Mooring, et al., (2011), "Design and Synthesis of Novel Small-Molecule Inhibitors of the Hypoxia Inducible Factor Pathway.", Journal of Medicinal Chemistry, 54(24): 8471-8489.
Chau, et al., (2005), "Identification of Novel Small Molecule Inhibitors of Hypoxia-Inducible Factor-1 that Differentially Block Hypoxia-Inducible Factor-1 Activity and Hypoxia-Inducible Factor-1 a Induction in Response to Hypoxic Stress and Growth Factors.", Cancer Research, 65(11):4918-4928.
Prado, et al., (2007), "Synthesis and Antimycobacterial Evaluation of Benzofurobenzopyran Analogues.", Bioorganic & Medicinal Chemistry, 15(5): 2177-2186.
Park, et al., (2006), "Targeting the PAS-A Domain of HIF-1a for Development of Small Molecule Inhibitors of HIF-1.", Cell Cycle, 5(16): 1847-1853.

* cited by examiner

*Primary Examiner* — Craig Ricci
(74) *Attorney, Agent, or Firm* — Emory Patent Group

(57) ABSTRACT

Inhibitors of the Hypoxia Inducible Factor (HIF) and angiogenesis and their methods of use including the treatment of cancer, hypoxia related pathologies, disorders leading to ischemia, for example stroke and ischemic heart disease, and non-cancerous angiogenic diseases are provided.

7 Claims, 2 Drawing Sheets

| IC₅₀ (n=) | STDev | Log P | Structure |
|---|---|---|---|
| 0.59 (21) | 0.29 | 5.2 | 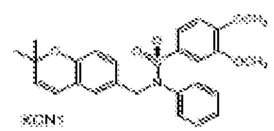 |
| 0.68 (5) | 0.51 | 4.9 | 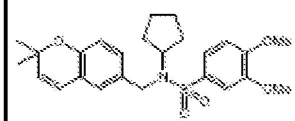 |
| 0.88 (7) | 0.75 | 5.6 | 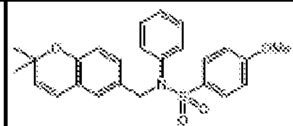 |
| 0.67 (7) | 0.64 | 6.4 | 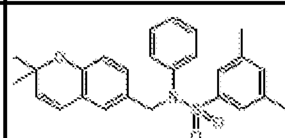 |
| 0.29 (8) | 0.17 | 4.8 | 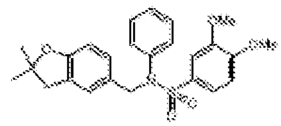 |
| 0.70 (5) | 0.16 | 4.2 | 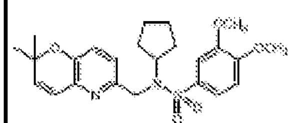 |
| 0.28 (21) | 0.12 | 3.5 | 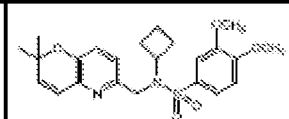 |
| 0.41 (6) | 0.28 | 4.6 | 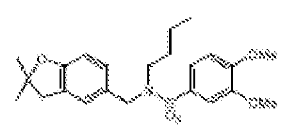 |
| 0.43 (6) | 0.19 | 4.5 | 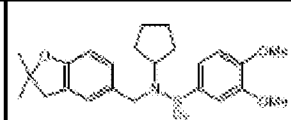 |

FIG. 2

INHIBITORS OF HIF AND ANGIOGENESIS

This application claims priority to U.S. Provisional Application No. 61/326,039 filed 20 Apr. 2010, hereby incorporated by reference.

ACKNOWLEDGEMENTS

This invention was made with government support under Grant No. CA116804 awarded by the National Institutes of Health. The government has certain rights in the invention.

FIELD

The present disclosure is generally directed to inhibitors of the Hypoxia Inducible Factor (HIF) pathway and their methods of use including anti-tumor therapies and disorders leading to ischemia (stroke, ischemic heart disease etc.) as well as non-cancerous angiogenic diseases (rheumatoid arthritis and macular degeneration).

BACKGROUND

Cancer accounts for nearly one quarter of deaths in the United States, exceeded only by heart diseases. In 2006, there were 559,888 cancer deaths in the US (National Center for Health Statistics: 2009). Although recent advances have increased our understanding of some of the mechanisms leading to cancer, to this day, finding effective treatments for cancer is a major challenge among researchers. Cancer is now primarily treated with one or a combination of three types of therapies: surgery; radiation; and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone or brainstem, nor in the treatment of disseminated neoplastic conditions such as leukemia. Radiation therapy involves the exposure of living tissue to ionizing radiation causing death or damage to exposed cells. Side effects from radiation therapy may be acute and temporary, while others may be irreversible. Chemotherapy involves the disruption of cell replication or cell metabolism. It is used most often in the treatment of breast, lung, and testicular cancer. One of the main causes of failure in this treatment of cancer is the development of drug resistance by cancer cells, a serious problem that may lead to recurrence of the disease or even death.

Hypoxia, a characteristic of solid tumors, can pose a major hindrance to effective solid tumor therapy. It is characterized by a reduction in the partial oxygen pressure in cells or tissue. Oxygen can diffuse 100-180 μM from the end of the nearest capillary to the cells before it is used up completely (Powis and Kirkpatrick, 2004, *Mol Cancer Ther.*, 3:647-654). Therefore, in solid tumors, when the existing vascular system is unable to supply the growing tumor with adequate amounts of oxygen, it results in hypoxia, low pH and lack of sufficient nutrients (Denko, 2008, *Nat Rev Cancer,* 8:705-713; Pouyssegur et al., 2006, *Nature,* 441:437-443). Tissue oxygen electrode measurements taken in cancer patients have shown a median range of oxygen partial pressure of 10 to 30 mmHg, with a significant proportion of readings below 2.5 mmHg, whereas those in normal tissues range from 24 to 66 mmHg. (Vaupel, 1993 in *Drug Resistance in Oncology*. Teicher, (ed.) 53-85, Marcel Dekker, New York). Tumor hypoxia has been shown to reduce the effectiveness of radiation and chemotherapy (Harris, 2002, *Nat Rev Cancer,* 2:38-47; Brown and Giaccia, 1998, *Cancer Res.* 58:1408-1416). In the absence of oxygen, which is the most electro-affinic molecule in cells and reacts chemically with the fundamental biological lesion produced by ionizing radiation, radiotherapy is severely compromised in its ability to kill hypoxic tumor cells (Gray et al., 1953, *Br J Radiol,* 26:638-648). Hypoxia increases the progression of malignancy and metastasis by promoting angiogenesis (Hockel and Vaupel, 2001, *J Natl Cancer Inst,* 93:266-276; Harris, 2002, *Nat Rev Cancer,* 2:38-47). On the other hand, hypoxia (and possibly hypoxia-associated deficiencies in other nutrients such as glucose) can cause tumor cells to stop or slow their rate of progression through the cell cycle (Amellem and Pettersen, 1991, *Cell Prolif,* 24:127-141).

Because most anticancer drugs are more effective against rapidly proliferating cells than slowly or non-proliferating cells, this slowing of cell proliferation leads to decreased cell killing. Chemotherapy is further affected by hypoxia as chemotherapeutic drugs are delivered systemically. The diffusion of these drugs into the tumor decreases the exposure of the hypoxic regions to the drug as compared to oxygenated cells proximal to the vessels. Hypoxia also drives genetic changes in tumors such as loss or mutation of the p53 tumor suppressor gene. Moreover, the multidrug resistance (MDR1) gene product P-glycoprotein is induced by ambient hypoxia. (Comerford et al., 2002, *Cancer Res,* 62: 3387-3394). Finally, hypoxic regions are expected to be less amenable to immunotherapy due to their distance from nearby vessels and compromised lymphocyte function in a hypoxic environment. Tumor cells in this aberrant environment are therefore often resistant to radio- and chemotherapy (Brown and Giaccia, 1998, *Cancer Res.,* 58:1408-1416).

Hypoxia Inducible Factor is the primary transcription factor activated by hypoxia and is responsible for orchestrating a number of cellular responses such as angiogenesis and glycolysis that help tumor cells adapt to hypoxic conditions (Greijer et al., 2005, *J Pathol,* 206:291-304). Over-expression of HIF-1 has been associated with increased patient mortality in several cancer types including breast, stomach, cervical, endometrial and ovarian cancers. See review by Quintero et al., J Cancer Sur., 2004, 30, 465-468. Tumor hypoxia and the expression of the hypoxia-inducible factor (HIF) family of proteins are also linked to poorer survival in patients with non-small cell lung cancer. See Jackson et al., Expert Opin Ther Targets, 2010, 14(10):1047-57.

HIF-1 activation and regulation is complex, with numerous points of potential inhibition. Clinical evidence has determined that expression of HIF-1 is strongly associated with poor patient prognosis (Brown and Giaccia, 1998, *Cancer Res.,* 58:1408-1416). Active HIF is composed of alpha (HIF-1α, 2α) and beta (HIF-1β) subunits that dimerize and bind to consensus sequences (hypoxia responsive elements, HRE) in the regulatory regions of target genes. HIF controls the expression of more than 60 target genes whose products are critical to many aspects of tumor progression, including metabolic adaptation, apoptosis resistance, angiogenesis and metastasis. These include the Vascular Endothelial Growth Factor (VEGF), erythropoietin, glucose transporters, and glycolytic enzymes. In normoxia, HIF is hydroxylated and interacts with the von Hippel Lindau protein (pVHL), an E3 ubiquitin ligase subunit that targets HIF for degradation. In the absence of oxygen, HIF hydroxylation is inhibited, preventing binding to pVHL and leading to its intracellular accumulation. HIF-1 has been recognized as an important molecular target for solid tumor therapy due to its crucial role in tumor angiogenesis and progression.

A component of tumor growth is angiogenesis. Angiogenesis is a process by which new blood vessels are formed, and is essential in reproduction, development, and wound repair. Under these conditions, angiogenesis is highly regulated, so that it is turned on only as necessary, usually for brief periods of days, and then completely inhibited. However, many diseases are driven by persistent unregulated angiogenesis. For example, in tumor formation, angiogenesis is a critical step for tumor growth beyond a few mm² and is associated with vascular leakiness and edema; in arthritis, new capillary blood vessels can invade the joint and destroy cartilage; and in diabetes, new capillaries can invade the vitreous humor, bleed, and cause blindness. VEGF, the most important known regulator of tumor angiogenesis is transcriptionally upregulated by HIF-1.

A number of research groups have identified compounds that can inhibit the HIF-1 pathway. These compounds affect HIF-1 levels by directly inhibiting HIF-1 signaling or by indirectly inhibiting signal pathways that affect HIF-1 expression. The mechanisms of action for HIF-1 inhibitors can involve reduction in HIF-1α mRNA levels or protein levels, HIF-1 DNA-binding activity or HIF-1 mediated transactivation of target genes. Compounds may also reduce protein levels by decreasing the rate of HIF-1α synthesis or by increasing the rate of HIF-1α degradation. A number of patent applications have provided small molecules based on a 2,2-dimethylbenzopyran scaffold for use in the treatment of hypoxia related pathologies (see e.g. WO 2004/087066 A2, WO 2007/025169 A2, WO 2010/006184 A2 and WO 2010/006189 A2). PCT Publication No. WO 2007/025169 A2 provides a range of small molecules characterized by aryl or heteroaryl moieties linked by a disulphide bridge as inhibitors to HIF-1. Hsp90 inhibitors, such as geldanamycin and its analogues can inhibit the HIF-1 pathway by binding to Hsp90 and interfering with its function as Hsp90 plays an important role in the stabilization of HIF-1α under hypoxic conditions (see Sato et al., 2000, *Proc Natl Acad Sci USA*, 97:10832-10837; Whitesell et al., 1994, *Proc Natl Acad Sci USA.*, 91:8324-8328; Zhou et al. 2004, *J. Biol. Chem.* 279:13506-13513; Katschinski et al., 2002, *J. Biol. Chem.* 277:9262-9267 and Isaacs et al., 2002, *J Biol Chem.*, 277:29936-44).

Inhibitors of topoisomerase such topotecan and a campothothecin analogue have also been identified as HIF inhibitors (Rapisarda et al., 2002, *Cancer Res*, 62:4316-4324; Rapisarda et al., 2004, *Cancer Res*, 64:1475-1482 and Rapisarda et al., 2004, *Cancer Res*, 64:6845-6848). It was determined that 2-methoxyestradiol inhibits tumor growth and angiogenesis by disrupting tumor microtubules (MTs) in vivo and inhibits HIF-1 induced transcriptional activation of VEGF expression (Mabjeesh et al., 2003, *Cancer cell*, 3:363-375). Thioredoxin inhibitors PX-12 and pleurotin have also been identified as inhibitors of HIF-1α and VEGF (Welsh et al., 2003, *Mol Cancer Ther.*, 2:235-243). Echinomycin has been shown to affect HIF-1 DNA binding (Kong et al., 2005, *Cancer Res*, 65:9047-9055). PX-478 (S-2-amino-3-[4V—N, N,-bis(2-chloroethyl)amino]phenylpropionic acid N-oxide dihydrochloride) is a HIF-1 inhibitor that reduces HIF-1α protein levels (Welsh et al., 2004, *Mol Cancer Ther*, 3:233-244). The HIF-1 inhibitor DJ12 inhibits the binding of HIF-1 to DNA and prevents the activation of transcription (Jones and Harris, 2006, *Molecular Cancer Therapeutics*, 5:2193-2202).

Other mechanisms that decrease HIF-1α protein levels include inhibition of the cyclin dependent kinase by flavopiridol which also has an effect on VEGF (Newcomb et al, 2005, *Neuro-Oncology*, 7:225-235). Chetomin has been shown to be a disrupter of HIF by binding to p300, interfering with its interaction with HIF and inhibits tumor growth (Kung et al., 2004, *Cancer cell*, 6:33-43). The antifungal drug amphoteric B also inhibits HIF-1 leading to decreased recruitment of p300 (Yeo et al., 2006, *Blood*, 107:916-923). Another inhibitor includes the histone deacetylyase inhibitor, FK228, a bicyclic peptide, which has also been shown to inhibit HIF-1 activity under hypoxic conditions, as well as inhibit tumor angiogenesis (Lee et al., 2003, *Biochem and Biophys Res Commun*, 300:241-246).

Effective treatments for cancer are a major challenge among researchers and there is a need for new therapies targeting abnormal proliferative disorders. In particular, there is a need for new treatments that address hypoxia and its role in hyper-proliferative pathologies. It is thus the object of this disclosure to provide compounds and methods for treatment or prophylaxis of disorders characterized by abnormal cell proliferation. It is a further object of the disclosure to provide compounds and methods of treatment or prophylaxis of other disorders such as those leading to ischemia (e.g., stroke and ischemic heart disease), and non-cancerous angiogenic diseases such as rheumatoid arthritis and macular degeneration.

SUMMARY

General aspects of the present disclosure are directed to HIF inhibitors and derivatives thereof, pharmaceutical compositions including a HIF inhibitor, and methods of using these compounds in the treatment of hypoxia-related pathologies. Pathologies targeted by the HIF inhibitors of the present disclosure include, for example, ischemic diseases, proliferative diseases such as cancer, diseases related to excessive vascularization, and the like.

In certain embodiments, the disclosure relates to compounds disclosed herein optionally substituted with one or more substitutes that are the same or different.

In certain embodiments, the disclosure relates to compounds of Formula I

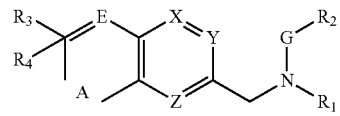

Formula I or salt, ester, or prodrug thereof wherein,

---- is a single bond or a double bond if $R^4$ is absent; A is $-CR^5R^6-$, $-CR^7=CR^8-$, or $-CR^7R^9-CR^8R^{10}-$; E is O, S, or $CR^{11}$; G is $-SO_2-$, $-SO-$, $-C(=O)-$, or a single bond between N and $R^2$; X is N or $CR^{12}$; Y is N or $CR^{13}$; Z is N or $CR^{14}$; $R^1$ is alkyl, carbocyclyl, aryl, or heterocyclyl, wherein $R^1$ is optionally substituted with one or more, the same or different, $R^{15}$; $R^2$ is alkyl, carbocyclyl, aryl, or heterocyclyl, wherein $R^2$ is optionally substituted with one or more, the same or different, $R^{16}$; $R^3$ is hydrogen or alkyl, wherein $R^3$ is optionally substituted with one or more, the same or different, $R^{17}$; $R^4$ is hydrogen, alkyl, or absent, wherein if $R^4$ is alkyl it is optionally substituted with one or more, the same or different, $R^{18}$;

$R^5$, $R^6$, $R^7$, $R^8$, $R^9$, $R^{10}$, $R^{11}$, $R^{12}$, $R^{13}$, and $R^{14}$ are each individually and independently selected from hydrogen, alkyl, halogen, nitro, cyano, hydroxy, amino, mercapto, formyl, carboxy, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, optionally substituted with one or more, the same or different, $R^{19}$;

$R^{15}$, $R^{16}$, $R^{17}$, $R^{18}$, and $R^{19}$ are halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, A is $-CR^5R^6-$; X is N, Y is $CR^{13}$, and Z is $CR^{14}$; Y is N, X is $CR^{12}$, and Z is $CR^{14}$; Z is N, X is $CR^{12}$, and Y is $CR^{13}$; $R^1$ is a cyclopropyl, cyclobutyl or cyclopentyl; G is $-C(=O)-$; $R^3$ is alkyl other than methyl; ---- is a double bond, E is $CR^{11}$, and A is $-CR^7=CR^8-$ or methylene; $R^2$ is 4-methoxyphenyl, 3,4-dimethoxyphenyl, or 3,5-dimethylphenyl; and $R^3$ and $R^4$ are alkyl.

In certain embodiments, the compound is N-cyclopentyl-N-((2,2-dimethyl-2H-chromen-6-yl)methyl)-3,4-dimethoxybenzenesulfonamide;
N-((2,2-dimethyl-2H-chromen-6-yl)methyl)-4-methoxy-N-phenylbenzenesulfonamide;
N-((2,2-dimethyl-2H-chromen-6-yl)methyl)-3,5-dimethyl-N-phenylbenzenesulfonamide;
N-((2,2-dimethyl-2,3-dihydrobenzofuran-5-yl)methyl)-3,4-dimethoxy-N-phenylbenzenesulfonamide;
N-cyclopentyl-N-((2,2-dimethyl-2H-pyrano[3,2-b]pyridin-6-yl)methyl)-3,4-dimethoxybenzenesulfonamide;
N-cyclobutyl-N-((2,2-dimethyl-2H-pyrano[3,2-b]pyridin-6-yl)methyl)-3,4-dimethoxybenzenesulfonamide;
N-butyl-N-((2,2-dimethyl-2,3-dihydrobenzofuran-5-yl)methyl)-3,4-dimethoxybenzenesulfonamide; or
N-cyclopentyl-N-((2,2-dimethyl-2,3-dihydrobenzofuran-5-yl)methyl)-3,4-dimethoxybenzenesulfonamide or salts thereof.

Compounds, pharmaceutical compositions and methods of treatment or prophylaxis of a hypoxia-related pathology including certain compounds of Formula A are provided

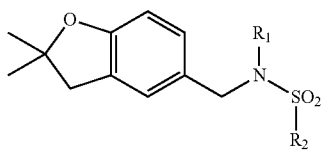

Formula A or pharmaceutically acceptable salts, prodrugs or derivatives thereof, wherein $R_1$ and $R_2$ are independently selected from: a substituted or unsubstituted phenyl group, an amide group, a heterocyclic group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. The substituents may be optional substituted with any of the following: H, OH, a substituted or unsubstituted phenyl group, an amide group, a heterocyclic group, a halogen, an alkoxy group, a carboxylic acid group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group. In certain embodiments, the $-SO_2-$ group may be replaced by a carbonyl group.

Further provided are compounds, pharmaceutical compositions and methods of inhibition or treatment or prophylaxis of a hypoxia-related pathology including certain compounds of Formula B

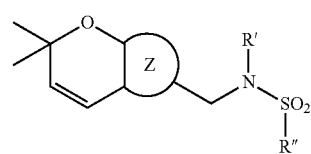

Formula B or pharmaceutically acceptable salts, prodrugs or derivatives thereof, wherein ring Z is a nitrogen containing aromatic ring and
R' and R" are independently selected from: a phenyl group, a monosubstituted phenyl group, a disubstituted phenyl group, an amide group, a heteroaromatic group, a bicyclic aromatic or heteroaromatic group a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. The substituents may be optional substituted with any of the following: H, OH, a substituted or unsubstituted phenyl group, an amide group, a heterocyclic group, a halogen, an alkoxy group, a carboxylic acid group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group. In certain embodiments, the $-SO_2-$ group may be replaced by a carbonyl group. In certain embodiments, the double bond of the pyran ring is absent. In further embodiments, the pyran ring may be replaced by a 2,2-dimethyl dihydrofuran ring.

Further provided are compounds, pharmaceutical compositions and methods of inhibition or treatment or prophylaxis of a hypoxia-related pathology including certain compounds of Formula E

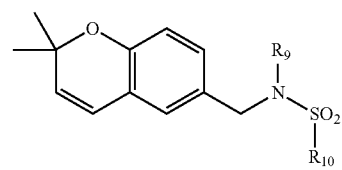

Formula E or pharmaceutically acceptable salts, prodrugs or derivatives thereof, wherein $R_9$ and $R_{10}$ are independently selected from: a phenyl group, a monosubstituted phenyl group, a disubstituted phenyl group, an amide group, a heteroaromatic group, a bicyclic aromatic or heteroaromatic group a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. The substituents may be optional substituted with any of the following: H, OH, a substituted or unsubstituted phenyl group, an amide group, a heterocyclic group, a halogen, an alkoxy group, a carboxylic acid group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group Wherein at least one of $R_9$ and $R_{10}$ is a substituted phenyl wherein at least on substituent is a carboxylic acid group or an ester derivative thereof). The carboxylic acid group may be linked to phenyl ring by a $C_1$ to $C_5$ alkyl group or a $C_1$ to $C_5$ alkoxy group. The second substituent may be chosen from H, an alkoxy group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivative thereof, or a $C_3$ to $C_8$ cycloalkyl group, which may be saturated or unsaturated. In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring.

Embodiments of the present disclosure include methods for the treatment or prevention of a hypoxia-related pathology comprising administering to a host in need of such treatment a HIF inhibiting amount of any of the compounds described herein or a pharmaceutically acceptable salt, prodrug or derivative thereof. In some embodiments, the host is typically suffering from a cancer, typically a solid tumor cancer. Embodiments of the present disclosure also include methods of modulating HIF activity in a cell comprising: contacting the cell with a HIF inhibiting amount of any of the compounds described herein or a pharmaceutically acceptable salt, prodrug or derivative thereof.

A method of treating or preventing cancer or a tumor in a subject is also provided, the method comprising administering to the subject in need thereof a therapeutically effective amount of any of the compounds described herein or a pharmaceutically acceptable salt, prodrug or derivative thereof.

This disclosure also provides a method of inhibiting angiogenesis in a subject, the method comprising administering to the subject an effective amount of a compound described herein or a pharmaceutically acceptable salt, prodrug or derivative thereof. In some embodiments, the angiogenesis is associated with non-cancerous pathologies.

Further provided herein is a method of treating macular degeneration in a subject, the method comprising administering to the subject a therapeutically effective amount of a compound described herein or a pharmaceutically acceptable salt, prodrug or derivative thereof. A method of modulating transcription and/or translation of a nucleic acid sequence in a cell is provided, the method comprising contacting the cell with an effective amount of a compound described herein or a pharmaceutically acceptable salt, prodrug or derivative thereof. In some embodiments, the cell is a cancer cell. In some embodiments, the nucleic acid sequence encodes for VEGF, erythropoietin, a glucose transporter, a glycolytic enzyme, carbonic anhydrase IX, or tyrosine hydroxylase.

Provided herein is a method of modulating a basic-helix-loop-helix transcription factor in a cell, the method comprising administering to the cell an effective amount of a compound described herein or a pharmaceutically acceptable salt, prodrug or derivative thereof.

Also provided herein is a method of modulating mRNA translation in a cell comprising contacting the cell with an effective amount of a compound described herein or a pharmaceutically acceptable salt, prodrug or derivative thereof.

This disclosure further provides a pharmaceutical composition comprising a pharmaceutically acceptable carrier and a compound described herein or a pharmaceutically acceptable salt, prodrug or derivative thereof.

Other embodiments are directed to the use of the disclosed compositions in the preparation of a medicament for the treatment hypoxia-related pathology. In certain embodiments, the disclosure relates to pharmaceutical compositions comprising a compound provided herein or pharmaceutically acceptable salt and a pharmaceutically acceptable excipient and their use in methods of treatment or preventing a hypoxia-related pathology such as cancer comprising administering a compound disclosed herein to a patient in need thereof.

In certain embodiments, the disclosure relates to processes for producing compounds disclosed herein utilizing synthetic procedures provided herein. In certain embodiments, the disclosure relates to processes for producing a compound of Formula I

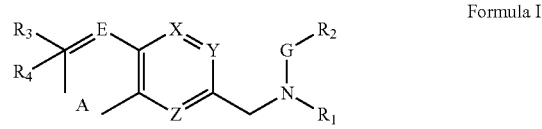

Formula I comprising mixing a compound of Formula II and a compound of Formula III

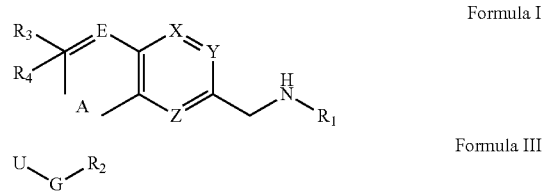

Formula I

Formula III wherein U is a leaving group such as a halogen, under conditions such that a compound of formula I is formed.

In certain embodiments, the compounds disclosed herein are administered in combination with another anticancer agent such as docetaxel, cis-platin, 5-fluorouracil, gemcitabine, tegafur, raltitrexed, methotrexate, cytosine arabinoside, hydroxyurea, adriamycin, bleomycin, doxorubicin, daunomycin, epirubicin, idarubicin, mitomycin-C, dactinomycin and mithramycin, vincristine, vinblastine, vindesine, vinorelbine taxol, taxotere, etoposide, teniposide, amsacrine, topotecan, camptothecin bortezomib anegrilide, tamoxifen, toremifene, raloxifene, droloxifene, iodoxyfene fulvestrant, bicalutamide, flutamide, nilutamide, cyproterone, goserelin, leuprorelin, buserelin, megestrol anastrozole, letrozole, vorazole, exemestane, finasteride, marimastat, trastuzumab, cetuximab, gefitinib, erlotinib, dasatinib, imatinib, bevacizumab, combretastatin, thalidomide, and/or lenalidomide or combinations thereof.

In certain embodiments, the subject is diagnosed with lung cancer, hepatocellular cancer, hematologic malignancies, gastrointestinal stromal tumors, colorectal cancer, gastric cancer, ocular melanoma, pancreatic cancer, prostate cancer, cervical cancer, breast cancer, Ewing Sarcoma family of Tumors, or skin cancer or a cancer driven by a chimeric gene resulting from a gene rearrangement involving the Ewing Sarcoma protein (EWS) gene.

The details of one or more embodiments of the disclosure are set forth in the accompanying drawings and the description below. Other compositions, methods, features, and advantages of the present disclosure will be or become apparent to one with skill in the art upon examination of the following drawings and detailed description. It is intended that all such additional compositions, methods, features, and advantages be included within this description, be within the scope of the present disclosure, and be protected by the accompanying claims.

BRIEF DESCRIPTION OF THE FIGURE

FIG. 2 shows inhibition data for embodiments disclosed herein.

DETAILED DESCRIPTION OF THE DISCLOSURE

Figure 1:
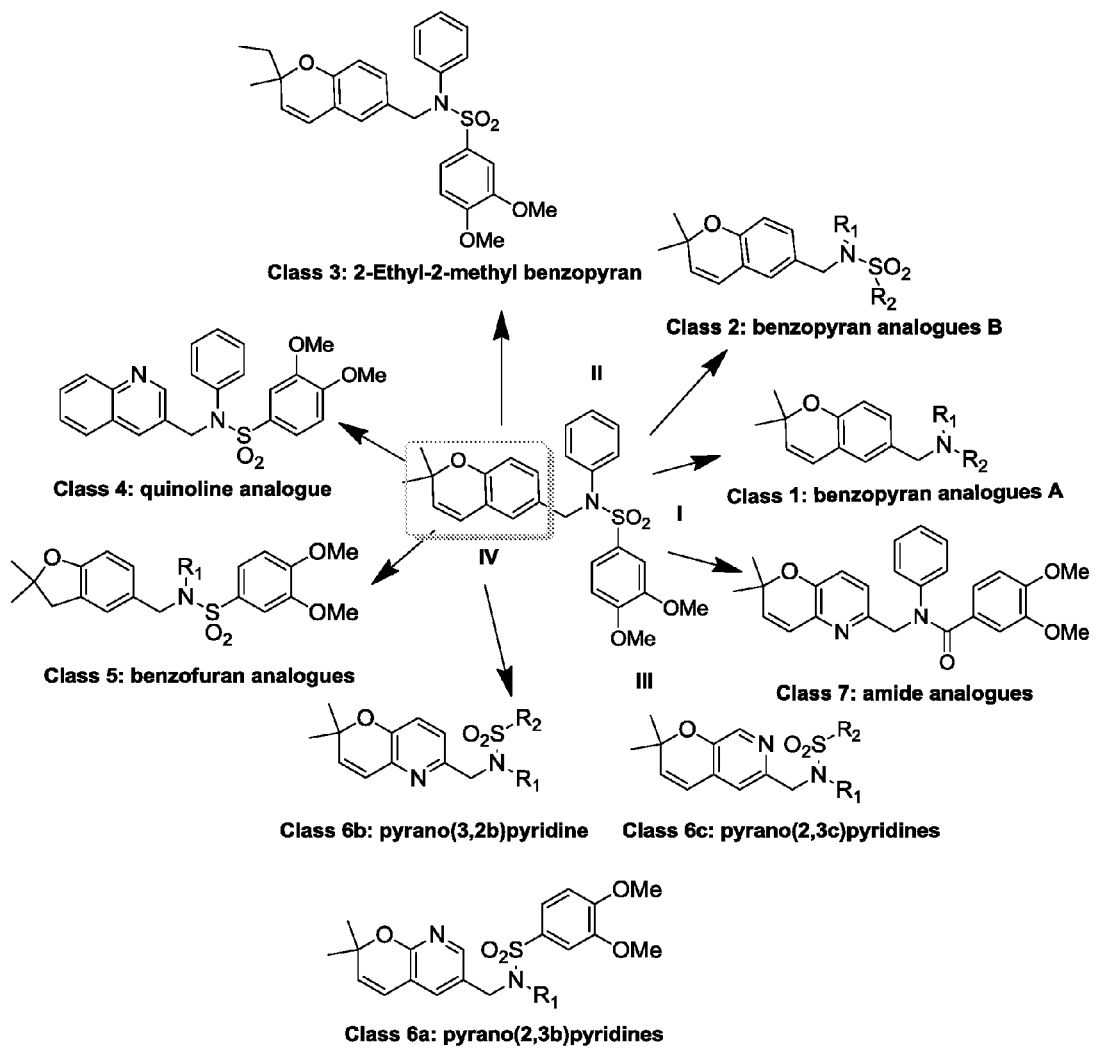
FIG. 1 illustrates embodiments disclosed herein.

It has been discovered that certain compounds disclosed herein inhibit HIF-1, bind to Ewing Sarcoma Protein (EWS), and/or are angiogenesis inhibitors. Thus, the disclosure relates to compounds, pharmaceutical compositions, and therapeutic method related thereto.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

It is also to be understood that the terminology used herein is for the purpose of describing particular embodiments only, and is not intended to be limiting, since the scope of the present disclosure will be limited only by the appended claims.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Embodiments of the present disclosure will employ, unless otherwise indicated, techniques of synthetic organic chemistry, biochemistry, biology, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a compound" includes a plurality of compounds. In this specification and in the claims that follow, reference will be made to a number of terms that shall be defined to have the following meanings unless a contrary intention is apparent.

1. Definitions

The term "HIF inhibitor" means a compound, pharmaceutically acceptable salt, prodrug, or derivative thereof that inhibits the biological activity of any of the HIF factors, e.g., HIF-1, HIF-2, and HIF-3, interferes with the HIF signal transduction pathway, or down regulates expression or availability of HIF in a cell or organism.

The term "hypoxia-related pathology" means a pathology that is caused in part, either directly or indirectly, by conditions of below typical physiological amounts of oxygen. The term includes cancer, cancer metastasis, ischemia, stroke and related conditions, diseases, or syndromes. In some embodiments a hypoxia related pathology is a disorder characterised by abnormal cell proliferation.

The term "hypoxia-related pathology" also means a pathology caused by non-hypoxic stimuli.

The term "organism", "host" or "subject" (as in the subject of the treatment) refers to any living entity comprised of at least one cell. A living organism can be as simple as, for example, a single eukaryotic cell or as complex as a mammal, including a human being. Mammals include, for example, humans; non-human primates, e.g. apes and monkeys; cattle; horses; sheep; rats; mice; pigs; and goats. Non-mammals include, for example, fish and birds.

As used herein, the term "derivative" refers to a chemically or biologically modified version of a chemical compound that is structurally similar to a parent compound and (actually or theoretically) derivable from that parent compound. A "derivative" differs from an "analogue" in that a parent compound may be the starting material to generate a "derivative," whereas the parent compound may not necessarily be used as the starting material to generate an "analogue." A derivative may or may not have different chemical or physical properties of the parent compound. For example, the derivative may be more hydrophilic or it may have altered reactivity as compared to the parent compound. Derivatization (i.e., modification) may involve substitution of one or more moieties within the molecule (e.g., a change in functional group).

The term "derivative" also includes conjugates, metabolites, and prodrugs of a parent compound (i.e., chemically modified derivatives which can be converted into the original compound under physiological conditions).

The term "therapeutically effective amount" as used herein refers to that amount of the compound being administered which will relieve to some extent one or more of the symptoms of the disorder being treated. In reference to cancer or pathologies related to unregulated cell division and/or lack of programmed cell death, a therapeutically effective amount refers to that amount which has the effect of (1) reducing the size of a tumor, (2) inhibiting (that is, slowing to some extent, preferably stopping) aberrant cell division, for example cancer cell division, (3) preventing or reducing the local invasion and distant metastasis of cancer cells, (4) relieving to some extent (or, preferably, eliminating) one or more symptoms associated with a pathology related to or caused in part by unregulated or aberrant cellular division, including for example, cancer, (5) prevention of the formation of cancer by application of the compound (like sun screen to protect against cancer), and/or (6) to prevent the chain of events downstream of an initial ischemic condition which leads to the pathology.

The term "contacting" means bringing at least two moieties together, whether in an in vitro system or an in vivo system.

The term "modulating" as used herein means changing, adjusting, or varying a property of a molecule or pathway including increasing, decreasing, inhibiting, or activating the activity or quantity of the molecule, or activity or inhibition of a pathway.

A "pharmaceutical composition" refers to a mixture of one or more of the compounds described herein, or pharmaceutically acceptable salts thereof, with other chemical components, such as physiologically acceptable carriers and excipients. One purpose of a pharmaceutical composition is to facilitate administration of a compound to an organism.

As used herein, a "pharmaceutically acceptable carrier" refers to a carrier or diluent that does not cause significant irritation to an organism and does not abrogate the biological activity and properties of the administered compound.

An "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

As used herein, the term "topically active agents" refers to compositions of the present disclosure that elicit pharmacological responses at the site of application (contact in a topical application) to a host.

As used herein, the term "topically" refers to application of the compositions of the present disclosure to the surface of the skin and mucosal cells and tissues.

As used herein, the terms "prevent" and "preventing" include the prevention of the recurrence, spread or onset. It is not intended that the present disclosure be limited to complete prevention. In some embodiments, the onset is delayed, or the severity is reduced.

As used herein, the terms "treat" and "treating" are not limited to the case where the subject (e.g. patient) is cured and the disease is eradicated. Rather, embodiments of the present disclosure also contemplate treatment that merely reduces symptoms, and/or delays disease progression.

As used herein, "alkyl" means a noncyclic straight chain or branched, unsaturated or saturated hydrocarbon such as those containing from 1 to 10 carbon atoms. Representative saturated straight chain alkyls include methyl, ethyl, n-propyl, n-butyl, n-pentyl, n-hexyl, n-septyl, n-octyl, n-nonyl, and the like; while saturated branched alkyls include isopropyl, sec-butyl, isobutyl, tert-butyl, isopentyl, and the like. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butyryl, 2-butyryl, 1-pentynyl, 2-pentynyl, 3-methyl-1-butyryl, and the like.

Non-aromatic mono or polycyclic alkyls are referred to herein as "carbocycles" or "carbocyclyl" groups. Representative saturated carbocycles include cyclopropyl, cyclobutyl, cyclopentyl, cyclohexyl, and the like; while unsaturated carbocycles include cyclopentenyl and cyclohexenyl, and the like.

"Heterocarbocycles" or heterocarbocyclyl" groups are carbocycles which contain from 1 to 4 heteroatoms independently selected from nitrogen, oxygen and sulfur which may be saturated or unsaturated (but not aromatic), monocyclic or polycyclic, and wherein the nitrogen and sulfur heteroatoms may be optionally oxidized, and the nitrogen heteroatom may be optionally quaternized. Heterocarbocycles include morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The term "aryl" refers to aromatic homocyclic (i.e., hydrocarbon) mono-, bi- or tricyclic ring-containing groups preferably having 6 to 12 members such as phenyl, naphthyl and biphenyl. Phenyl is a preferred aryl group. The term "substituted aryl" refers to aryl groups substituted with one or more groups, preferably selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane, sulfonyl, and, the like, where optionally one or more pair of substituents together with the atoms to which they are bonded form a 3 to 7 member ring.

As used herein, "heteroaryl" or "heteroaromatic" refers an aromatic heterocarbocycle having 1 to 4 heteroatoms selected from nitrogen, oxygen and sulfur, and containing at least 1 carbon atom, including both mono- and polycyclic ring systems. Polycyclic ring systems may, but are not required to, contain one or more non-aromatic rings, as long as one of the rings is aromatic. Representative heteroaryls are furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl. It is contemplated that the use of the term "heteroaryl" includes N-alkylated derivatives such as a 1-methylimidazol-5-yl substituent.

As used herein, "heterocycle" or "heterocyclyl" refers to mono- and polycyclic ring systems having 1 to 4 heteroatoms selected from nitrogen, oxygen and sulfur, and containing at least 1 carbon atom. The mono- and polycyclic ring systems may be aromatic, non-aromatic or mixtures of aromatic and non-aromatic rings. Heterocycle includes heterocarbocycles, heteroaryls, and the like.

"Alkylthio" refers to an alkyl group as defined above with the indicated number of carbon atoms attached through a sulfur bridge. An example of an alkylthio is methylthio, (i.e., —S—$CH_3$).

"Alkoxy" refers to an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

"Alkylamino" refers an alkyl group as defined above with the indicated number of carbon atoms attached through an amino bridge. An example of an alkylamino is methylamino, (i.e., —NH—$CH_3$).

"Alkanoyl" refers to an alkyl as defined above with the indicated number of carbon atoms attached through a carbonyl bride (i.e., —(C=O)alkyl).

"Alkylsulfonyl" refers to an alkyl as defined above with the indicated number of carbon atoms attached through a sulfonyl bridge (i.e., —S(=O)$_2$alkyl) such as mesyl and the like, and "Arylsulfonyl" refers to an aryl attached through a sulfonyl bridge (i.e., —S(=O)$_2$aryl).

"Alkylsulfamoyl" refers to an alkyl as defined above with the indicated number of carbon atoms attached through a sulfamoyl bridge (i.e., —NHS(=O)$_2$alkyl), and an "Arylsulfamoyl" refers to an alkyl attached through a sulfamoyl bridge (i.e., (i.e., —NHS(=O)$_2$aryl).

"Alkylsulfinyl" refers to an alkyl as defined above with the indicated number of carbon atoms attached through a sulfinyl bridge (i.e. —S(=O)alkyl).

The term "substituted" refers to a molecule wherein at least one hydrogen atom is replaced with a substituent. When substituted, one or more of the groups are "substituents." The molecule may be multiply substituted. In the case of an oxo substituent ("=O"), two hydrogen atoms are replaced. Example substituents within this context may include halogen, hydroxy, alkyl, alkoxy, nitro, cyano, oxo, carbocyclyl, carbocycloalkyl, heterocarbocyclyl, heterocarbocycloalkyl, aryl, arylalkyl, heteroaryl, heteroarylalkyl, —NRaRb, —NRaC(=O)Rb, —NRaC(=O)NRaNRb, —NRaC(=O)ORb, —NRaSO2Rb, —C(=O)Ra, —C(=O)ORa, —C(=O)NRaRb, —OC(=O)NRaRb, —ORa, —SRa, —SORa, —S(=O)2Ra, —OS(=O)2Ra and —S(=O)2ORa. Ra and Rb in this context may be the same or different and independently hydrogen, halogen hydroxyl, alkyl, alkoxy, alkyl, amino, alkylamino, dialkylamino, carbocyclyl, carbocycloalkyl, heterocarbocyclyl, heterocarbocycloalkyl, aryl, arylalkyl, heteroaryl, heteroarylalkyl.

The term "optionally substituted," as used herein, means that substitution is optional and therefore it is possible for the designated atom to be unsubstituted.

The terms "cycloalkyl" and "cycloalkenyl" refer to mono-, bi-, or tri homocyclic ring groups of 3 to 15 carbon atoms which are, respectively, fully saturated and partially unsaturated. The term "cycloalkenyl" includes bi- and tricyclic ring systems that are not aromatic as a whole, but contain aromatic portions (e.g., fluorene, tetrahydronapthalene, dihydroindene, and the like). The rings of multi-ring cycloalkyl groups may be either fused, bridged and/or joined through one or more spiro unions. The terms "substituted cycloalkyl" and "substituted cycloalkenyl" refer, respectively, to cycloalkyl and cycloalkenyl groups substituted with one or more groups, preferably selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane, sulfonyl, and the like.

The terms "halogen" and "halo" refer to fluorine, chlorine, bromine, and iodine.

Throughout the specification, groups and substituents thereof may be chosen to provide stable moieties and compounds.

The disclosed compounds form salts which are also within the scope of this disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when a compound contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation.

The disclosed compounds that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those Tormea with sulfuric acid), sulfonates (such as those mentioned herein), tartrates, thiocyanates, toluenesulfonates such as tosylates, undecanoates, and the like.

The disclosed compounds that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

To the extent that the disclosed compounds, and salts thereof, may exist in their tautomeric form, all such tautomeric forms are contemplated herein as part of the present disclosure.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this disclosure. Individual stereoisomers of the compounds of the disclosure may, for example, be substantially free of other isomers, or may be admixed, for example, as racemates or with all other, or other selected, stereoisomers. The chiral centers of the compounds of the present disclosure can have the S or R configuration as defined by the IUPAC 1974 Recommendations.

The terms "including", "such as", "for example" and the like are intended to refer to exemplary embodiments and not to limit the scope of the present disclosure.

2. Hypoxia Inducible Factor (HIF-1)

HIF-1 is a primary transcriptional factor responsible for specific induction of genes in hypoxia. HIF-1 is composed of two subunits belonging to the bHLH-PAS family: HIF-1α and aryl hydrocarbon receptor nuclear translocator (ARNT also known as HIF-1β). To activate transaction of target genes, HIF-1α dimerizes with HIF-1β and binds to consensus sequences (hypoxia responsive element, HRE) in the promoter or enhancer regions of these genes. Proteins encoded by such genes include vascular endothelial growth factor (VEGF), erythropoietin, glucose transporter-1, glycolytic enzymes and tyrosine hydroxylase (Semenza, 1999, *Annu Rev Cell Dev Biol.*, 15:551-578).

In normoxia, von Hippel Lindau protein (pVHL) organizes the assembly of a complex that activates the E3 ubiquitin ligase which then ubiquitinylates HIF-1α, targeting its degradation. The interaction between HIF-1α and pVHL is regulated through hydroxylation of two proline residues of HIF-1α by a prolyl hydroxylase. In the absence of oxygen, this enzyme is no longer active and HIF-1α does not interact with pVHL and accumulates intracellularly (Ivan et al., 2001, *Science*, 292:464-468; Jaakkola et al., 2001, *Science*, 292:468-472).

Tumor hypoxia increases malignant progression and metastasis by promoting angiogenesis through the induction of proangiogenic proteins such as VEGF (Schweiki et al., 1992, *Nature*, 359:843-845). Most genes induced by hypoxia are regulated by HIF-1α, this protein therefore plays a pivotal role in tumor development (Dachs and Chaplin, 1998, *Semin Radiat Oncol.*, 8:208-216; Maxwell et al., 1997, *Proc Natl Acad Sci USA.*, 94:8104-8109; Semenza, 1998, *Curr Opin Genet Dev.*, 8:588-594). Histological analyses have shown that an increased level of intracellular HIF-1α was associated with poor prognosis and resistance to therapy in head and neck, breast, cervical and oropharyngeal cancers (Beasley et al., 2002, *Cancer Res.*, 62:2493-2497; Schindl et al., 2002, *Clin Cancer Res.*, 8:1831-1837; Birner et al., 2000, *Cancer Res.*, 60:4693-4696; Aebersold et al., 2001, *Cancer Res.*, 61:2911-2916). HIF-1α was overexpressed in the cytoplasm and the nucleus of colon, breast, gastric, lung, skin, ovarian, pancreatic, prostate and renal carcinomas.

3. Compounds

General aspects of the present disclosure are directed to HIF inhibitors and derivatives thereof, pharmaceutical compositions including a HIF inhibitor, and methods of using these compounds in the treatment of hypoxia-related pathologies, for example, in the treatment of ischemic diseases, proliferative diseases such as cancer, diseases related to excessive vascularization and the like.

In certain embodiments, the disclosure relates to compounds of Formula I

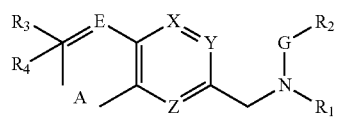

Formula I or salt, ester, or prodrug thereof wherein,

--- is a single bond or a double bond if $R^4$ is absent; A is $—CR^5R^6—$, $—CR^7=CR^8—$, or $—CR^7R^9—CR^8R^{10}—$; E is O, S, or $CR^{11}$; G is $—SO_2—$, $—SO—$, $—C(=O)—$, or a single bond between N and $R^2$; X is N or $CR^{12}$; Y is N or $CR^{13}$; Z is N or $CR^{14}$; $R^1$ is alkyl, carbocyclyl, aryl, or heterocyclyl, wherein $R^1$ is optionally substituted with one or more, the same or different, $R^{15}$; $R^2$ is alkyl, carbocyclyl, aryl, or heterocyclyl, wherein $R^2$ is optionally substituted with one or more, the same or different, $R^{16}$; $R^3$ is hydrogen or alkyl, wherein $R^3$ is optionally substituted with one or more, the same or different, $R^{17}$; $R^4$ is hydrogen, alkyl, or absent, wherein if $R^4$ is alkyl it is optionally substituted with one or more, the same or different, $R^{18}$;

$R^5$, $R^6$, $R^7$, $R^8$, $R^9$, $R^{10}$, $R^{11}$, $R^{12}$, $R^{13}$, and $R^{14}$ are each individually and independently selected from hydrogen, alkyl, halogen, nitro, cyano, hydroxy, amino, mercapto, formyl, carboxy, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, optionally substituted with one or more, the same or different, $R^{19}$;

$R^{15}$, $R^{16}$, $R^{17}$, $R^{18}$, and $R^{19}$ are halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, A is $—CR^5R^6—$; X is N, Y is $CR^{13}$, and Z is $CR^{14}$; Y is N, X is $CR^{12}$, and Z is $CR^{14}$; Z is N, X is $CR^{12}$, and Y is $CR^{13}$; $R^1$ is a cyclopropyl, cyclobutyl or cyclopentyl; G is $—C(=O)—$; $R^3$ is alkyl other than methyl; --- is a double bond, E is $CR^{11}$, and A is $—CR^7=CR^8—$ or methylene; $R^2$ is 4-methoxyphenyl, 3,4-dimethoxyphenyl, or 3,5-dimethylphenyl; and $R^3$ and $R^4$ are alkyl.

In certain embodiments, the disclosure relates to compounds of Formula IV

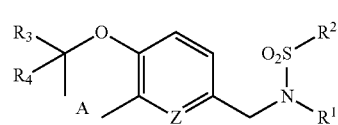

Formula IV or salt, ester, or prodrug thereof wherein,

A is $—CR^5R^6—$ or $—CR^7=CR^8—$; Z is N or $CR^{14}$; $R^1$ is alkyl, carbocyclyl, aryl, or heterocyclyl, wherein $R^1$ is optionally substituted with one or more, the same or different, $R^{15}$; $R^2$ is alkyl, carbocyclyl, aryl, or heterocyclyl, wherein $R^2$ is optionally substituted with one or more, the same or different, $R^{16}$; $R^3$ is hydrogen or alkyl, wherein $R^3$ is optionally substituted with one or more, the same or different, $R^{17}$; $R^4$ is hydrogen, alkyl, or absent, wherein if $R^4$ is alkyl it is optionally substituted with one or more, the same or different, $R^{18}$;

$R^5$, $R^6$, $R^7$, $R^8$, and $R^{14}$ are each individually and independently selected from hydrogen, alkyl, halogen, nitro, cyano, hydroxy, amino, mercapto, formyl, carboxy, carbamoyl, alkoxy, alkylthio, alkylamino, (alkyl)$_2$-amino, alkylsulfinyl, alkylsulfonyl, arylsulfonyl, carbocyclyl, aryl, or heterocyclyl, optionally substituted with one or more, the same or different, $R^{19}$;

$R^{15}$, $R^{16}$, $R^{17}$, $R^{18}$, and $R^{19}$ are halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

In certain embodiments, A is $—CR^5R^6—$; $R^1$ is a cyclopropyl, cyclobutyl, or cyclopentyl; $R^2$ is 4-methoxyphenyl, 3,4-dimethoxyphenyl, or 3,5-dimethylphenyl; and $R^3$ and $R^4$ are alkyl.

Compounds, pharmaceutical compositions and methods of treatment or prophylaxis of a hypoxia-related pathology including certain compounds of Formula A are provided

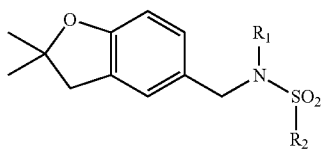

Formula A or pharmaceutically acceptable salts, prodrugs or derivatives thereof, wherein $R_1$ and $R_2$ are independently selected from: a substituted or unsubstituted phenyl group, an amide group, a heterocyclic group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. The substituents may be optional substituted with any of the following: H, OH, a substituted or unsubstituted phenyl group, an amide group, a heterocyclic group, a halogen, an alkoxy group, a carboxylic acid group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group. In certain embodiments, the —$SO_2$— group may be replaced by a carbonyl group.

In specific embodiments, the group $R_2$ is limited to 3,4-dimethoxybenzene, as depicted in Formula A1

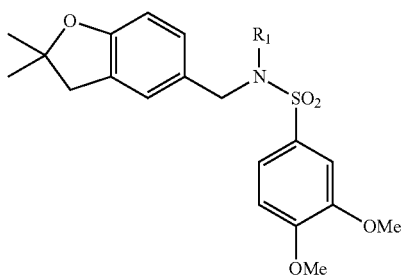

Formula A1 or pharmaceutically acceptable salts, prodrugs or derivatives thereof, wherein $R_1$ is independently selected from: a phenyl group, a monosubstituted phenyl group, a disubstituted phenyl group, an amide group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. In certain embodiments $R_1$ a phenyl group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. In specific embodiments $R_1$ is a phenyl group, a $C_5$ to $C_7$ cycloalkyl group or a $C_4$ alkyl group, which may be branched or unbranched. In certain embodiments, the —$SO_2$— group may be replaced by a carbonyl group.

Further provided are compounds, pharmaceutical compositions and methods of inhibition or treatment or prophylaxis of a hypoxia-related pathology including certain compounds of Formula B

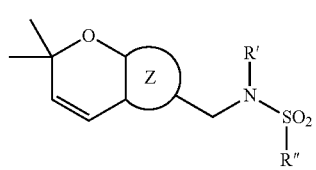

Formula B or pharmaceutically acceptable salts, prodrugs or derivatives thereof, wherein ring Z is a nitrogen containing aromatic ring and R' and R" are independently selected from: a phenyl group, a monosubstituted phenyl group, a disubstituted phenyl group, an amide group, a heteroaromatic group, a bicyclic aromatic or heteroaromatic group a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. The substituents may be optional substituted with any of the following: H, OH, a substituted or unsubstituted phenyl group, an amide group, a heterocyclic group, a halogen, an alkoxy group, a carboxylic acid group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group. In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring.

Further provided are compounds, pharmaceutical compositions and methods of inhibition or treatment or prophylaxis of a hypoxia-related pathology including certain compounds of Formula B1

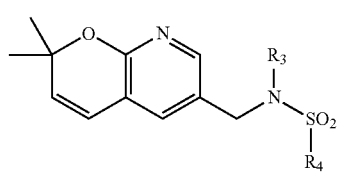

Formula B1 or pharmaceutically acceptable salts, prodrugs or derivatives thereof, wherein $R_3$ and $R_4$ are independently selected from: a phenyl group, a monosubstituted phenyl group, a disubstituted phenyl group, an amide group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring.

In specific embodiments, the group $R_4$ is limited to 3,4-dimethoxybenzene, as depicted in Formula B2

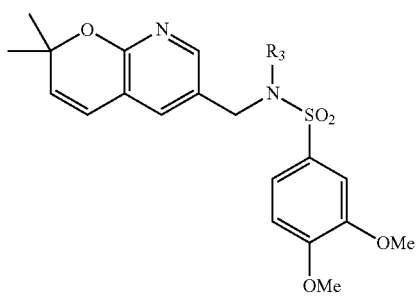

Formula B2 or pharmaceutically acceptable salts, prodrugs or derivatives thereof, wherein $R_3$ is independently selected from: a phenyl group, a monosubstituted phenyl group, a disubstituted phenyl group, an amide group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. In certain embodiment $R_3$ is selected from a monosubstituted phenyl group, a disubstituted phenyl group, a $C_1$ to $C_7$ alkyl group or any branched derivatives thereof, or a $C_3$ to $C_8$ cycloalkyl group, which may be saturated or unsaturated. In certain embodiment $R_3$ is selected from a phenyl group or a $C_3$ to $C_8$ cycloalkyl group which may be saturated or unsaturated. In a more specific embodiment $R_3$ is selected from a phenyl group or a $C_6$ cycloalkyl group (cyclohexyl). In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring.

Another aspect provides compounds, pharmaceutical compositions and methods of inhibition or treatment or prophylaxis of a hypoxia-related pathology including certain compounds of Formula C

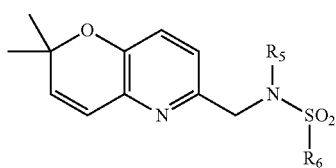

Formula C or pharmaceutically acceptable salts, prodrugs or derivatives thereof, wherein $R_5$ and $R_6$ are independently selected from: a phenyl group, a monosubstituted phenyl group, a disubstituted phenyl group, a heteroaromatic group, a bicyclic aromatic or heteroaromatic group, an amide group, a $C_1$ to $C_7$ alkyl group or any branched derivatives thereof, a $C_2$ to $C_7$ alkenyl group or any branched derivatives thereof, a $C_2$ to $C_7$ alkynyl group or a $C_3$ to $C_8$ cycloalkyl group, which may be saturated or unsaturated. In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring. In certain embodiments, at least one of $R_5$ or $R_6$ is a monosubstituted phenyl group with a substituent chosen from alkoxy, a phenyl or a halogen. In certain other embodiments, at least one of $R_5$ or $R_6$ is a disubstituted phenyl group wherein the substituents are chosen from an alkoxy group or an alkyl group and when the substituents are ortho to each other, where the substituents may come together to form a fused dioxane or a fused dioxolane ring system or a cycloalkyl ring.

In specific embodiments, the group $R_6$ is 3,4-dimethoxybenzene, as depicted in Formula C1

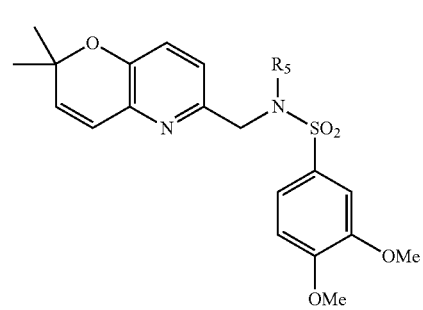

Formula C1 or pharmaceutically acceptable salts, prodrugs or derivatives thereof, wherein $R_5$ is independently selected from: a phenyl group, a monosubstituted phenyl group (wherein the substituents may be chosen from for example an alkoxy group, a phenyl group or a halogen), a disubstituted phenyl group (wherein the substituents may be chosen from for example an alkoxy group or an alkyl group and when the substituents are ortho to each other, may come together to form a fused dioxane or a fused dioxolane ring system or a cycloalkyl ring), a heteroaromatic group, a bicyclic aromatic or heteroaromatic group, an amide group, a $C_1$ to $C_7$ alkyl group or any branched derivatives thereof, a $C_2$ to $C_7$ alkenyl group or any branched derivatives thereof, a $C_2$ to $C_7$ alkynyl group or a $C_3$ to $C_8$ cycloalkyl group, which may be saturated or unsaturated.

In a further embodiment, $R_5$ may be selected from a phenyl group, a monosubstituted phenyl group (wherein the substituents may be chosen from for example an alkoxy group, a phenyl group or a halogen), a disubstituted phenyl group (wherein the substituents may be chosen from for example an alkoxy group or an alkyl group and when the substituents are ortho to each other, may come together to form a fused dioxane or a fused dioxolane ring system or a cycloalkyl ring), a $C_1$ to $C_7$ alkyl group or any branched derivatives thereof, or a $C_3$ to $C_8$ cycloalkyl group which may be saturated or unsaturated.

In a more specific embodiment, $R_5$ may be chosen from a phenyl group, a monosubstituted phenyl group (wherein the substituent is halogen), a disubstituted phenyl group (wherein the substituents may be chosen from for example an alkoxy group or an alkyl group and when the substituents are ortho to each other, may come together to form a fused dioxane or a fused dioxolane ring system or a cycloalkyl ring), a $C_1$ to $C_7$ alkyl group, or a $C_4$ to $C_8$ cycloalkyl group.

More specifically $R_5$ may be chosen from a phenyl group, a monosubstituted phenyl group (wherein the substituent is flourine), a dimethoxybenzene group, a benzene ring fused to a cyclohexyl group, a $C_4$ alkyl group (butyl), or a $C_4$ to $C_8$ cycloalkyl group.

In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring.

In specific embodiments, the group $R_5$ is limited to a phenyl group, as depicted in Formula C2

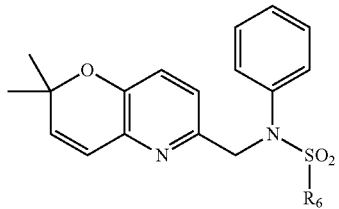

Formula C2 or pharmaceutically acceptable salts, prodrugs or derivatives thereof, wherein $R_6$ is independently selected from: a phenyl group, a monosubstituted phenyl group (wherein the substituents may be chosen from for example an alkoxy group, a phenyl group or a halogen), a disubstituted phenyl group (wherein the substituents may be chosen from for example an alkoxy group and when the substituents are ortho to each other, may come together to form a fused dioxane or a fused dioxolane ring system), a heteroaromatic group, a bicyclic aromatic or heteroaromatic group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof or a $C_3$ to $C_8$ cycloalkyl group, which may be saturated or unsaturated.

In a further embodiment $R_6$ is selected from a monosubstituted phenyl group (wherein the substituents may be chosen from for example a phenyl group or a halogen), a disubstituted phenyl group (wherein the substituents may be chosen from for example an alkoxy group and when the substituents are ortho to each other, may come together to form a fused dioxane or a fused dioxolane ring system), a heteroaromatic group, a bicyclic aromatic or heteroaromatic group, a $C_1$ to $C_7$ alkyl group or any branched derivatives thereof, or a $C_3$ to $C_8$ cycloalkyl group which may be saturated or unsaturated.

In a specific embodiment $R_6$ is selected from a monosubstituted phenyl group (wherein the substituent is a phenyl group), a disubstituted phenyl group (wherein the substituents may be chosen from for example an alkoxy group and when the substituents are ortho to each other, may come together to form a fused dioxane or a fused dioxolane ring system), a bicyclic heteroaromatic group, a $C_3$ to $C_4$ alkyl group or any branched derivatives thereof, or a $C_3$ to $C_6$ cycloalkyl group.

In a more specific embodiment $R_6$ may be selected from a monosubstituted phenyl group (wherein the substituent is a phenyl group), a dihydrobenzo[1,4]dioxine, a benzodioxole, a quinoline group, a $C_3$ to $C_4$ alkyl group or any branched derivatives thereof (n-propyl, i-propyl, n-butyl or i-butyl), or a $C_3$ to $C_6$ cycloalkyl group (cyclopropyl or cyclohexyl).

In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring.

Further provided are compounds, pharmaceutical compositions and methods of inhibition or treatment or prophylaxis of a hypoxia-related pathology including certain compounds of Formula D

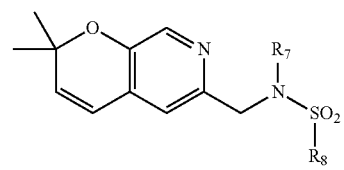

Formula D or pharmaceutically acceptable salts, prodrugs or derivatives thereof, wherein $R_7$ and $R_8$ are independently selected from: a phenyl group, a monosubstituted phenyl group or a disubstituted phenyl group, an amide group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivative thereof, or a $C_3$ to $C_8$ cycloalkyl group, which may be saturated or unsaturated. In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring. In certain embodiments, at least one of $R_7$ and $R_8$ is a monosubstituted or disubstituted phenyl group wherein the substituents are chosen from a $C_1$ to $C_7$ alkyl group or any branched derivatives thereof, an alkoxy group, a nitro group and a halogen.

In specific embodiments, the group $R_7$ is limited to a phenyl group, as depicted in Formula D1

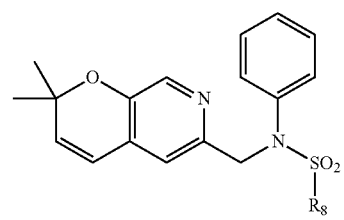

Formula D1 or pharmaceutically acceptable salts, prodrugs or derivatives thereof, wherein $R_8$ may be selected from: a phenyl group, a monosubstituted phenyl group or a disubstituted phenyl group (wherein the substituents may be chosen from for example a $C_1$ to $C_7$ alkyl group or any branched derivatives thereof, an alkoxy group, a nitro group and a halogen), an amide group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivative thereof, or a $C_3$ to $C_8$ cycloalkyl group, which may be saturated or unsaturated.

In a further embodiment $R_8$ may be chosen from a monosubstituted phenyl group or a disubstituted phenyl group (wherein the substituents may be chosen from for example a $C_1$ to $C_7$ alkyl group or any branched derivatives thereof, an alkoxy group, a nitro group and a halogen).

In a more specific embodiment $R_8$ may be chosen from a monosubstituted phenyl group (wherein the substituents may be an isopropyl group, a methoxy group or nitro group) or may be a dimethoxybenzene group.

In specific embodiments, the group $R_7$ is a cyclohexyl group, as depicted in Formula D2

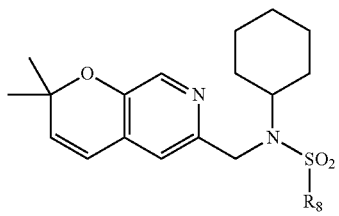

Formula D2 or pharmaceutically acceptable salts, prodrugs or derivatives thereof, wherein $R_8$ may be selected from: a phenyl group, a monosubstituted phenyl group or a disubstituted phenyl group (wherein the substituents may be chosen from for example a $C_1$ to $C_7$ alkyl group or any branched derivatives thereof, an alkoxy group, a nitro group and a halogen), an amide group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivative thereof, or a $C_3$ to $C_8$ cycloalkyl group, which may be saturated or unsaturated.

In a further embodiment $R_8$ may be chosen from a monosubstituted phenyl group or a disubstituted phenyl group (wherein the substituents may be chosen from for example a $C_1$ to $C_7$ alkyl group or any branched derivatives thereof, an alkoxy group, a nitro group and a halogen).

In a more specific embodiment $R_8$ may be chosen from a monosubstituted phenyl group (wherein the substituents may be an isopropyl group, a methoxy group or nitro group) or may be a dimethoxybenzene group.

Further provided are compounds, pharmaceutical compositions and methods of inhibition or treatment or prophylaxis of a hypoxia-related pathology including certain compounds of Formula E

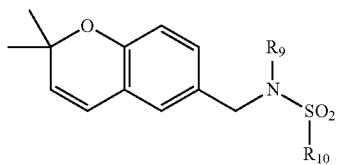

Formula E or pharmaceutically acceptable salts, prodrugs or derivatives thereof, wherein $R_9$ and $R_{10}$ are independently selected from: a phenyl group, a monosubstituted phenyl group, a disubstituted phenyl group, an amide group, a heteroaromatic group, a bicyclic aromatic or heteroaromatic group a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. The substituents may be optional substituted with any of the following: H, OH, a substituted or unsubstituted phenyl group, an amide group, a heterocyclic group, a halogen, an alkoxy group, a carboxylic acid group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group Wherein at least one of $R_9$ and $R_{10}$ is a substituted phenyl wherein at least on substituent is a carboxylic acid group or an ester derivative thereof). The carboxylic acid group may be linked to phenyl ring by a $C_1$ to $C_5$ alkyl group or a $C_1$ to $C_5$ alkoxy group. The second substitutent may be chosen from H, an alkoxy group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivatives thereof, or a $C_3$ to $C_8$ cycloalkyl group, which may be saturated or unsaturated. In certain embodiments, the —$SO_2$— group may be replaced by a carbonyl group. In certain embodiments, the double bond of the pyran ring is absent. In further embodiments, the pyran ring may be replaced by a 2,2-dimethyl dihydrofuran ring.

In specific embodiments, the group $R_9$ is limited to a phenyl group, as depicted in Formula E1

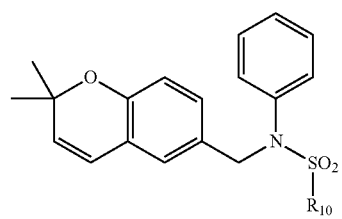

Formula E1 or pharmaceutically acceptable salts, prodrugs or derivatives thereof, wherein $R_{10}$ may be selected from: phenyl group, a monosubstituted phenyl group or a disubstituted phenyl group (wherein at least one of the substituents on the phenyl ring is a carboxylic acid group or an ester derivative thereof). The carboxylic acid group may be linked to phenyl ring by a $C_1$ to $C_5$ alkyl group or a $C_1$ to $C_5$ alkoxy group. The second substitutent may be chosen from H, an alkoxy group, a $C_1$ to $C_7$ alkyl group or any branched derivatives thereof, a $C_2$ to $C_7$ alkenyl group or any branched derivatives thereof, a $C_2$ to $C_7$ alkynyl group or any branched derivative thereof, or a $C_3$ to $C_8$ cycloalkyl group, which may be saturated or unsaturated.

In further embodiments $R_{10}$ may be selected from: a monosubstituted phenyl group or a disubstituted phenyl group (wherein at least one of the substituents on the phenyl ring is a carboxylic acid group or an ester derivative thereof). The carboxylic acid group may be linked to phenyl ring by a $C_1$ to $C_5$ alkyl group or a $C_1$ to $C_5$ alkoxy group. The second substituent may be chosen from H, an alkoxy group or a $C_1$ to $C_7$ alkyl group or any branched derivatives thereof.

In more specific embodiments the group $R_{10}$ may be chosen from: a monosubstituted phenyl group or a disubstituted phenyl group (wherein at least one of the substituents on the phenyl ring is a carboxylic acid group or an ester derivative thereof). The carboxylic acid group may be linked to phenyl ring by a $C_1$ to $C_5$ alkoxy group. The second substituent may be chosen from H or an alkoxy group.

Compounds according to formulas described herein can be synthesized by conventional techniques using readily available starting materials. In general, a compound of formula I, IV, A, B, C, D or E is conveniently obtained and isolated via standard organic chemistry methods. These scaffolds, containing an aldehyde functionality, can be subsequently modified using a reductive amination, to introduce the amine, followed by sulfonation to introduce the sulfone, with its respective R group. Compounds can be synthesized using parallel synthesis, purified by common chromatographic techniques, and characterized by LC- or GC-MS.

The term "pharmaceutically acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification, or formulation of compounds described herein. In general, the useful properties of the compounds described herein do not depend critically on whether the compound is or is not in a salt form. Unless clearly indicated otherwise (such as specifying that the compound should be in "free base" or "free acid" form), reference in the specification to a compound of formula I, IV, A, B, C, D or E should be understood as encompassing salt forms of the compound, whether or not this is explicitly stated.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic, and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric, and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal, and transition metal salts such as, for example, calcium, magnesium, potassium, sodium and zinc salts. Pharmaceutically acceptable base addition salts also include organic salts made from basic amines such as, for example, N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared by conventional means from the corresponding compound according to formula I, IV, A, B, C, D or E by reacting, for example, the appropriate acid or base with a compound according to formula I, IV, A, B, C, D or E. Preferably the salts are in crystalline form, and preferably prepared by crystallization of the salt from a suitable solvent. A person skilled in the art will know how to prepare and select suitable salt forms for example, as described in Handbook of Pharmaceutical Salts Properties, Selection, and Use By P. H. Stahl and C. G. Wermuth (Wiley-VCH 2002).

The compounds described herein may be administered in the form of prodrugs. By "prodrug" is meant, for example, any compound (whether itself active or inactive) that is converted chemically in vivo into a biologically active compound as described herein following administration of the prodrug to a subject.

The term "prodrug" refers to an agent that is converted into a biologically active form in vivo. Prodrugs are often useful because, in some situations, they may be easier to administer than the parent compound. They may, for instance, be bioavailable by oral administration whereas the parent compound is not. The prodrug may also have improved solubility in pharmaceutical compositions over the parent drug. A prodrug may be converted into the parent drug by various mechanisms, including enzymatic processes and metabolic hydrolysis. Harper, N.J. (1962). Drug Latentiation in Jucker, ed. Progress in Drug Research, 4:221-294; Morozowich et al. (1977). Application of Physical Organic Principles to Prodrug Design in E. B. Roche ed. Design of Biopharmaceutical Properties through Prodrugs and Analogs, APhA; Acad. Pharm. Sci.; E. B. Roche, ed. (1977). Bioreversible Carriers in Drug in Drug Design, Theory and Application, APhA; H. Bundgaard, ed. (1985) Design of Prodrugs, Elsevier; Wang et al. (1999) Prodrug approaches to the improved delivery of peptide drug, Curr. Pharm. Design. 5(4):265-287; Pauletti et al. (1997). Improvement in peptide bioavailability: Peptidomimetics and Prodrug Strategies, Adv. Drug. Delivery Rev. 27:235-256; Mizen et al. (1998). The Use of Esters as Prodrugs for Oral Delivery of β-Lactam antibiotics, Pharm. Biotech. 11,: 345-365; Gaignault et al. (1996). Designing Prodrugs and Bioprecursors I. Carrier Prodrugs, Pract. Med. Chem. 671-696; M. Asgharnejad (2000). Improving Oral Drug Transport Via Prodrugs, in G. L. Amidon, P. I. Lee and E. M. Topp, Eds., Transport Processes in Pharmaceutical Systems, Marcell Dekker, p. 185-218; Balant et al. (1990) Prodrugs for the improvement of drug absorption via different routes of administration, Eur. J. Drug Metah. Pharmacokinet, 15(2): 143-53; Balimane and Sinko (1999). Involvement of multiple transporters in the oral absorption of nucleoside analogues, Adv. Drug Delivery Rev., 39(1-3):183-209; Browne (1997). Fosphenyloin (Cerebyx), Clin. Neuropharmacol. 20(1): 1-12; Bundgaard (1979). Bioreversible derivatization of drugs-principle and applicability to improve the therapeutic effects of drugs, Arch. Pharm. Chemi. 86(1): 1-39; H. Bundgaard, ed. (1985) Design of Prodrugs, New York: Elsevier; Fleisher et al. (1996). Improved oral drug delivery: solubility limitations overcome by the use of prodrugs, Adv. Drug Delivery Rev. 19(2): 115-130; Fleisher et al. (1985). Design of prodrugs for improved gastrointestinal absorption by intestinal enzyme targeting, Methods Enzymol. 112: 360-81; Farquhar D, et al. (1983). Biologically Reversible Phosphate-Protective Groups, J. Pharm. Sci., 72(3): 324-325; Han, H. K. et al. (2000). Targeted prodrug design to optimize drug delivery, AAPS PharmSci., 2(1): E6; Sadzuka Y. (2000). Effective prodrug liposome and conversion to active metabolite, Curr. Drug Metab., 1(1):31-48; D. M. Lambert (2000) Rationale and applications of lipids as prodrug carriers, Eur. J. Pharm. Sci., 11 Suppl 2:S15-27; Wang, W. et al. (1999) Prodrug approaches to the improved delivery of peptide drugs. Curr. Pharm. Des., 5(4):265-87.

A prodrug can include a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include, for example, compounds wherein a hydroxyl group is bonded to any group that, when administered to a mammalian subject, cleaves to form a free hydroxyl group. Examples of prodrugs include, but are not limited to, acetate, formate and benzoate derivatives of alcohol functional groups in the compounds according to formula I, IV, A, B, C, D or E.

The suitability and techniques involved in making and using prodrugs are well known by those skilled in the art. Preparation and use of prodrugs is discussed in T. Higuchi and V. Stella, "Pro-drugs as Novel Delivery Systems," Vol. 14 of the ACS Symposium Series, and in Bioreversible Carriers in Drug Design, ed. Edward B. Roche, American Pharmaceutical Association and Pergamon Press, 1987, both of which are hereby incorporated by reference in their entirety.

4. Methods of Use

Some embodiments of the present disclosure are directed to interfering, inhibiting, or blocking signal transduction through the HIF pathway e.g., protein-protein and protein-nucleic acid and protein-lipid interactions involving HIF. Such inhibition can be accomplished by binding of HIF-1 or molecules associated with HIF with the disclosed compounds or their derivatives to render HIF-1 inactive or unavailable. Alternatively, the HIF-1 pathway can be inhibited, in whole or in part, by preventing the expression of HIF-1 in a cell (through preventing HIF mRNA transcription, post-transcriptional modification of HIF mRNA, translation of HIF mRNA, posttranslational modification of HIF protein and HIF stability). HIF-1 inhibition can also be achieved by interfering with the binding of HIF-1 or HIF-1 complexes to the hypoxia responsive element.

Methods of treatment or prophilaxis of a hypoxia-related pathology are provided comprising administering a compound described herein, or a pharmaceutically acceptable salt form thereof, to a subject in need thereof.

In certain embodiments, a basic-helix-loop-helix transcription factor is modulated by contacting an effective amount of compound described herein, or a salt form thereof, with the basic-helix-loop-helix transcription factor. In some embodiments, the modulation of a basic-helix-loop-helix transcription factor includes inhibition of the transcription factor. The basic-helix-loop-helix transcription factor can be any basic-helix-loop-helix transcription factor, or a heterodimeric structure basic-helix-loop-helix transcription factor. In some embodiments, the basic-helix-loop-helix transcription factor can be selected from ATOH1; AhR; AHRR; ARNT; ASCL1; BHLHB2; BMAL (e.g., ARNTL, ARNTL2); CLOCK; EPAS1; HAND (e.g, HAND-I and HAND-2); HES (e.g., HES-5 and HES-6); HEY (e.g., HEY-I, HEY-2, and HEY-L); HES-I; HIF (e.g., HIF-1α and HIF-3α); ID (e.g., ID-I, ID-2, ID-3, ID-4); LYL1; MXD4; MYCL1; MYCN; Myogenic regulatory factors (e.g., MyoD, Myogenin, MYF-5, MYF-6); Neurogeninsi; NeuroD (e.g., NeuroD-1 and NeuroD-2); NPAS (NPAS-I, NPAS-2, and NPAS-3); OLIG (e.g., OLIG-I and OLIG-2); Scleraxis; TAL-I; Twist; and USF-I.

In some embodiments, the basic-helix-loop-helix transcription factor can be a HIF transcription factor (e.g., HIF-I, HIF-1α, HIF-1β, HIF-2, and HIF-3α). In some embodiments, the basic-helix-loop-helix transcription factor can be HIF-1 (e.g., HIF-1α and HIF-1β). Also provided herein is a method of modulating HIF activity comprising contacting an effective amount of compound according to formula A, B, C, D and E, or a salt form thereof, with HIF. In some embodiments, modulating HIF activity includes inhibition of the transcription factor. In some embodiments, modulating HIF activity includes interfering, inhibiting, or blocking signal transduction through the HIF pathway. In some embodiments, modulating HIF activity includes inhibiting HIF activity Inhibition of HIF activity can be accomplished by binding HIF, molecules associated with HIF, or molecules needed for proper HIF folding with the disclosed compounds or their derivatives to render HIF inactive or unavailable. Alternatively, the HIF pathway can be inhibited, in whole or in part, by preventing the expression of HIF in a cell (through preventing HIF mRNA transcription, post-transcriptional modification of HIF mRNA, translation of HIF mRNA, posttranslational modification of HIF protein and HIF stability). HIF inhibition can also be achieved by interfering with the binding of HIF or HIF complexes to a hypoxia responsive element (HRE). In some embodiments, HIF can be HIF-1 or HIF-2. In some embodiments, HIF-1 can be HIF-1α or HIF-10. In some embodiments, HIF-2 can be HIF-2α or HIF-2β or HIF-3.

This disclosure also provides a method of modulating transcription and/or translation of a nucleic acid sequence (e.g., present in the genome or isolated there from) comprising contacting an effective amount of compound described herein, or a salt form thereof, with a cell. In some embodiments, the modulation of nucleic acid transcription or translation includes inhibition of the activity of a HIF transcription factor. The inhibition of HIF activity with the disclosed compounds and compositions can occur at transcriptional, translational, and/or posttranslational levels. The disclosed compounds can modulate nucleic acid transcription by binding to HIF and preventing HIF from forming complexes with other molecules including DNA and proteins. For example, the disclosed compounds and compositions can bind to HIF and induce conformational changes that prevent HIF from interacting with its biological targets. Alternatively, the disclosed compounds can bind HIF and form aggresomes or other complexes that sequester HIF or otherwise physically prevent HIF from interacting with other biological molecules. Finally, the disclosed compounds and compositions can inhibit or interfere with HIF folding including, but not limited to, the inhibiting or interfering with intracellular transport of chaperone species (e.g., HSP90) from the cytoplasm to the nucleus. The nucleic acid sequence can be any nucleic acid sequence, or a mixture of sequences. In some embodiments, the nucleic acid sequence can be selected from those encoding VEGF, erythropoietin, a glucose transporter (e.g., glucose transporter-1), a glycolytic enzyme, or tyrosine hydroxylase.

A method of modulating mRNA, including microRNA, translation is provided, the method comprising contacting an effective amount of a compound described herein, or a salt form thereof, with a cell. In some embodiments, the modulating of mRNA translation includes inhibition of a HIF transcription factor.

This disclosure also provides a method of inhibiting angiogenesis in a subject, comprising contacting an effective amount of a compound described herein, or a salt form thereof, with a cell. In some embodiments, the method includes inhibiting angiogenesis in a non-cancerous cell.

The methods described above may be performed in vitro or in vivo. In some embodiments, the methods can be performed by contacting a cell with a compound described herein or a salt form thereof, in vitro. Contacting can be performed in the presence of cells or alternatively may be performed in a cell free medium. Uses of such in vitro methods include, but are not limited to, use in a screening assay (for example, wherein the compound described herein is used as a positive control or standard compared to compounds of unknown activity or potency).

In some embodiments, the methods can be performed by contacting a cell with a compound described herein, or a salt form thereof, in vivo. Contacting can be achieved by causing the compound to be present in the subject in an amount effective to achieve the desired result. In some embodiments, an effective amount of a compound can be administered to the subject, or a prodrug of a compound can be administered to the subject.

Uses of such in vivo methods include, but are not limited to, use in methods of treating a disease or condition. In some embodiments, the methods may be used in a cancer cell, for example in a patient suffering from cancer. The method is preferably performed by administering an effective amount of a compound described herein, or a pharmaceutically acceptable salt form thereof, to a subject who is suffering from cancer.

In any of the above described methods, in some embodiments the cell can be a non-cancer cell. In any of the above described methods, in some embodiments the cell can be a cancer cell. Further provided herein is a method for treating cancer comprising administering a therapeutically effective amount of a compound described herein, or a salt form or prodrug thereof, to the subject.

Cancer is a general term for diseases in which abnormal cells divide without control. Cancer cells can invade nearby tissues and can spread through the bloodstream and lymphatic system to other parts of the body. It has been discovered that the administration of an HIF-1 inhibitor to a host, for example a mammal, inhibits or reduces cancer, tumor growth or formation, and the metastasis of tumor cells.

The compounds described herein are believed effective against a broad range of cancers and tumor types, including but not limited to bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. More particularly, cancers that may be treated by the compounds, compositions and methods described herein include, but are not limited to, the following: cardiac cancers, including, for example sarcoma, e.g., angiosarcoma, fibrosarcoma, rhabdomyosarcoma, and liposarcoma; myxoma; rhabdomyoma; fibroma; lipoma and teratoma; lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma; gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma; genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and lipoma; liver cancers, including, for example, hepatoma, e.g., hepatocellular carcinoma; cholangiocarcinoma; hepatoblastoma; angiosarcoma; hepatocellular adenoma; and hemangioma; bone cancers, including, for example, osteogenic sarcoma (osteosarcoma), fibrosarcoma, malignant fibrous histiocytoma, chondrosarcoma, Ewing's sarcoma family of tumors, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull, e.g., osteoma, hemangioma, granuloma, xanthoma, and osteitis deformans; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiforme, oligodendroglioma, PNET, schwannoma, retinoblastoma, neuroma and congenital tumors; neural crest derived cancers, e.g. neuroblastoma and cancers of the spinal cord, e.g., neurofibroma, meningioma, glioma, and sarcoma; gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma; hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

Cancers may be solid tumors that may or may not be metastatic. Cancers may also occur, as in leukemia, as a diffuse tissue. Thus, the term "tumor cell", as provided herein, includes a cell afflicted by any one of the above identified disorders, as well as cancer stem cells.

The compounds described herein can also be administered in combination with existing methods of treating cancers, for example by chemotherapy, irradiation, or surgery.

Thus, there is further provided a method of treating cancer comprising administering a therapeutically effective amount of a compound described herein, or a salt thereof, to a subject in need of such treatment, wherein a therapeutically effective amount of at least one further cancer chemotherapeutic agent is administered to the subject. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, geldanamycin derivatives (e.g., 17-AAG or 17-DMAG), gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, radicicol (Hsp90 inhibitor), rasburicase, rituximab, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Further provided herein is a method of treating a hypoxia-related pathology in a subject, comprising administering to the subject a therapeutically effective amount of a compound described herein. The compounds are believed effective against a broad range of hypoxia-related pathologies, including but not limited to hypoxemic hypoxia, such as the hypoxia caused by sleep apnea or hypopnea, chronic obstructive pulmonary disease or respiratory arrest, and shunts; anemic hypoxia; hypemic hypoxia, for example, as the result of carbon monoxide poisoning and methaemoglobinaemia; histotoxic hypoxia; and ischemic, or stagnant hypoxia (e.g., cerebral ischemia, ischemic heart disease and intrauterine hypoxia). The term "hypoxia-related pathology" can include a pathology that is caused in part, either directly or indirectly, by conditions of below typical physiological amounts of oxygen. The term "hypoxia-related pathology" also means a pathology caused by a non-hypoxic stimuli. The term includes cancer, cancer metastasis, ischemia, stroke and related conditions, diseases, or syndromes.

This disclosure also provides a method of treating non-cancerous angiogenic diseases in a subject, comprising administering to the subject a therapeutically effective amount of a compound described herein, or a salt form thereof. As used herein, "non-cancerous angiogenic diseases" refers to non-cancerous diseases or conditions wherein inappropriate angiogenesis is observed as a symptom of the disease. Non-limiting examples include, atherosclerotic plaque growth and hemorrhage; chronic cystitis; Crohn's disease; diabetic retinopathy; dystrophic epidermolysis bullosa; infantile hemangiomas; intraperitoneal bleeding in endometriosis; macular degeneration; prostate growth in benign prostatic hypertrophy; psoriasis; rheumatoid arthritis; verruca vulgaris; surgical adhesions; keloids; non-cancerous lesions; aneurysms and vascular malformations in the brain; varicose veins; hemorrhoids; and rosacea.

In some embodiments, a compound can be used to treat macular degeneration in a subject, comprising administering to the subject a therapeutically effective amount of a compound, or a salt form thereof. Macular degeneration can include age-related macular degeneration (AMD), dry macular degeneration, wet macular degeneration (e.g., classic choroidal neovascularization and occult choroidal neovascularization), and juvenile macular degeneration or macular dystrophy (e.g., Best's disease, Doyne's honeycomb retinal dystrophy, Sorsby's disease, and Stargardt's disease).

Another embodiment provides a method of treating psoriasis including administering to the host an HIF inhibiting amount of the disclosed compounds, compositions, derivatives, pharmaceutically acceptable salts, prodrugs, or combinations thereof. Inhibition of HIF-1 results in the inhibition of HIF mediated activation of VEGF, which interferes or inhibits VEGF signal transduction involved in psoriasis. It will be appreciated that the disclosed compositions can also be used to treat other VEGF mediated pathologies by interfering or inhibiting HIF mediated activation of VEGF.

Also provided herein is a method of treating excessive vascularization in a subject, comprising administering to the subject a therapeutically effective amount of a compound described herein. Tumors are thought to form their own vasculature by different mechanism such as angiogenesis, e.g. the local remodeling of existing vessels; vasculogenesis, the recruitment of endotheial progenitors from the bone-marrow; and transdifferentiation of cancer stem cells into vascular cells. Certain compounds disclosed herein are believed effective against a broad range of pathologies associated with excessive vascularization pathologies, including those of the eye such as age-related macular degeneration (AMD) and Diabetic retinopathy. In the methods of treatment described herein, the compounds described herein according to formula I, IV, A, B, C, D and E may be administered to subjects (mammals, including animals and humans) afflicted with a disease such as cancer or non-cancerous angiogenesis. In particular embodiments, the subject treated is a human.

The compounds may be administered by any route, including oral, rectal, sublingual, ocular, and parenteral administration. Parenteral administration includes, for example, intrathecal, intravenous, intramuscular, intraarterial, intraperitoneal, intranasal, intravaginal, intraocular, intravesical (e.g., to the bladder), intradermal, transdermal, topical, or subcutaneous administration. Also contemplated is the instillation of a drug in the body of the patient in a controlled formulation, with systemic or local release of the drug to occur at a later time. For example, the drug may be localized in a depot for controlled release to the circulation, or for release to a local site, e.g., at the site of tumor growth. Advantageously, the compounds are administered in the form of a pharmaceutical composition.

One or more compounds useful in the practice of the methods described herein may be administered simultaneously, by the same or different routes, or at different times during treatment. The compounds may be administered before, along with, or after other medications, including other compounds.

The treatment using methods described herein may be carried out for as long a period as necessary, either in a single, uninterrupted session, or in discrete sessions. The treating physician will know how to increase, decrease, or interrupt treatment based on patient response. According to one embodiment, treatment is carried out from about four to about sixteen weeks. The treatment schedule may be repeated as required. There is additionally provided a compound described herein, or any of the embodiments thereof, or a salt thereof, for use in any of the aforementioned methods of treatment, or for use in treatment of any of the aforementioned diseases or conditions. Also provided is a use of a compound described herein, or any of the embodiments thereof, or a salt thereof, for use in the manufacture of a medicament, for use in any of the aforementioned methods of treatment, or for use in of any of the aforementioned diseases or conditions.

5. Pharmaceutical Compositions

Pharmaceutical compositions and dosage forms of the disclosure comprise a pharmaceutically acceptable salt of disclosed or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical compositions and unit dosage forms of the disclosure typically also comprise one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient.

Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. For example, a dosage form used in the acute treatment of a disease or disorder may contain larger amounts of the active ingredient, for example the disclosed compounds or combinations thereof, than a dosage form used in the chronic treatment of the same disease or disorder. Similarly, a parenteral dosage form may contain smaller amounts of the active ingredient than an oral dosage form used to treat the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Typical pharmaceutical compositions and dosage forms comprise one or more excipients. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid. Like the amounts and types of excipients, the amounts and specific type of active ingredient in a dosage form may differ depending on factors such as, but not limited to, the route by which it is to be administered to patients. However, typical dosage forms of the compounds of the disclosure comprise a pharmaceutically acceptable salt, or a pharmaceutically acceptable polymorph, solvate, hydrate, dehydrate, co-crystal, anhydrous, or amorphous form thereof, in an amount of from about 10 mg to about 1000 mg, preferably in an amount of from about 25 mg to about 750 mg, and more preferably in an amount of from 50 mg to 500 mg.

Additionally, the compounds and/or compositions can be delivered using lipid- or polymer-based nanoparticles. For example, the nanoparticles can be designed to improve the pharmacological and therapeutic properties of drugs administered parenterally (Allen et al., 2004, *Science*, 303:1818-1822).

Pharmaceutical compositions of the disclosure that are suitable for oral administration can be presented as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington's Pharmaceutical Sciences, 18th ed., Mack Publishing, Easton, Pa. (1990).

Typical oral dosage forms of the compositions of the disclosure are prepared by combining the pharmaceutically acceptable salt of disclosed compounds in an intimate admixture with at least one excipient according to conventional pharmaceutical compounding techniques. Excipients can take a wide variety of forms depending on the form of the composition desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, microcrystalline cellulose, kaolin, diluents, granulating agents, lubricants, binders, and disintegrating agents.

Due to their ease of administration, tablets and capsules represent the most advantageous solid oral dosage unit forms, in which case solid pharmaceutical excipients are used. If desired, tablets can be coated by standard aqueous or non-aqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary. For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Examples of excipients that can be used in oral dosage forms of the disclosure include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, and AVICEL-PH-105 (available from FMC Corporation, American Viscose Division, Avicel Sales, Marcus Hook, Pa., U.S.A.), and mixtures thereof. An exemplary suitable binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions of the disclosure is typically present in from about 50 to about 99 weight percent of the pharmaceutical composition or dosage form.

Disintegrants are used in the compositions of the disclosure to provide tablets that disintegrate when exposed to an aqueous environment. Tablets that contain too much disintegrant may swell, crack, or disintegrate in storage, while those that contain too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) should be used to form solid oral dosage forms of the disclosure. The amount of disintegrant used varies based upon the type of formulation and mode of administration, and is readily discernible to those of ordinary skill in the art. Typical pharmaceutical compositions comprise from about 0.5 to about 15 weight percent of disintegrant, preferably from about 1 to about 5 weight percent of disintegrant. Disintegrants that can be used to form pharmaceutical compositions and dosage forms of the disclosure include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, clays, other algins, other celluloses, gums, and mixtures thereof.

Lubricants that can be used to form pharmaceutical compositions and dosage forms of the disclosure include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W. R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

This disclosure further encompasses lactose-free pharmaceutical compositions and dosage forms, wherein such compositions preferably contain little, if any, lactose or other mono- or di-saccharides. As used herein, the term "lactose-free" means that the amount of lactose present, if any, is insufficient to substantially increase the degradation rate of an active ingredient.

Lactose-free compositions of the disclosure can comprise excipients which are well known in the art and are listed in the USP (XXI)/NF (XVI), which is incorporated herein by reference. In general, lactose-free compositions comprise a pharmaceutically acceptable salt of an HIF-1 inhibitor, a binder/filler, and a lubricant in pharmaceutically compatible and pharmaceutically acceptable amounts. Preferred lactose-free dosage forms comprise a pharmaceutically acceptable salt of the disclosed compounds, microcrystalline cellulose, pre-gelatinized starch, and magnesium stearate. This disclosure further encompasses anhydrous pharmaceutical compositions and dosage forms comprising the disclosed compounds as active ingredients, since water can facilitate the degradation of some compounds. For example, the addition of water (e.g., 5%) is widely accepted in the pharmaceutical arts as a means of simulating long-term storage in order to determine characteristics such as shelf life or the stability of formulations over time. See, e.g., Jens T. Carstensen, Drug Stability: Principles & Practice, 379-80 (2nd ed., Marcel Dekker, NY, N.Y.: 1995). Water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms of the disclosure can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials) with or without desiccants, blister packs, and strip packs.

5.2 Controlled and Delayed Release Dosage Forms

Pharmaceutically acceptable salts of the disclosed compounds can be administered by controlled- or delayed-release means. Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Chemg-ju, Controlled Release Dosage Form Design, 2 (Technomic Publishing, Lancaster, Pa.: 2000).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under dosing a drug (i.e., going below the minimum therapeutic levels) as well as exceeding the toxicity level for the drug. Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds. A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), multilayer coatings, microparticles, liposomes, or microspheres or a combination thereof to provide the desired release profile in varying proportions. Additionally, ion exchange materials can be used to prepare immobilized, adsorbed salt forms of the disclosed compounds and thus effect controlled delivery of the drug. Examples of specific anion exchangers include, but are not limited to, Duolite® A568 and Duolite® AP143 (Rohm&Haas, Spring House, Pa. USA).

One embodiment of the disclosure encompasses a unit dosage form which comprises a pharmaceutically acceptable salt of the disclosed compounds (e.g., a sodium, potassium, or lithium salt), or a polymorph, solvate, hydrate, dehydrate, co-crystal, anhydrous, or amorphous form thereof, and one or more pharmaceutically acceptable excipients or diluents, wherein the pharmaceutical composition or dosage form is formulated for controlled-release. Specific dosage forms utilize an osmotic drug delivery system.

A particular and well-known osmotic drug delivery system is referred to as OROS® (Alza Corporation, Mountain View, Calif. USA). This technology can readily be adapted for the delivery of compounds and compositions of the disclosure. Various aspects of the technology are disclosed in U.S. Pat. Nos. 6,375,978 B1; 6,368,626 B1; 6,342,249 B1; 6,333,050 B2; 6,287,295 B1; 6,283,953 B1; 6,270,787 B1; 6,245,357 B1; and 6,132,420; each of which is incorporated herein by reference. Specific adaptations of OROS® that can be used to administer compounds and compositions of the disclosure include, but are not limited to, the OROS® Push-Pull™, Delayed Push-Pull™, Multi-Layer Push-Pull™, and Push-Stick™ Systems, all of which are well known. See, e.g. worldwide website alza.com. Additional OROS® systems that can be used for the controlled oral delivery of compounds and compositions of the disclosure include OROS®-CT and L-OROS®; see, Delivery Times, vol. 11, issue II (Alza Corporation).

Conventional OROS® oral dosage forms are made by compressing a drug powder (e.g., a HIF-1 inhibitor salt) into a hard tablet, coating the tablet with cellulose derivatives to form a semi-permeable membrane, and then drilling an orifice in the coating (e.g., with a laser). Kim, Chemg-ju, Controlled Release Dosage Form Design, 231-238 (Technomic Publishing, Lancaster, Pa.: 2000). The advantage of such dosage forms is that the delivery rate of the drug is not influenced by physiological or experimental conditions. Even a drug with a pH-dependent solubility can be delivered at a constant rate regardless of the pH of the delivery medium. But because these advantages are provided by a build-up of osmotic pressure within the dosage form after administration, conventional OROS® drug delivery systems cannot be used to effectively delivery drugs with low water solubility. Because HIF-1 inhibitor salts and complexes of this disclosure (e.g., an HIF-1 inhibitor sodium salt) may be far more soluble in water than an HIF-1 inhibitor itself, they may be well suited for osmotic-based delivery to patients. This disclosure does, however, encompass the incorporation of an HIF-1 inhibitor, and non-salt isomers and isomeric mixtures thereof, into OROS® dosage forms. A specific dosage form of the compositions of the disclosure comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a dry or substantially dry state drug layer located within the cavity adjacent the exit orifice and in direct or indirect contacting relationship with the expandable layer; and a flow-promoting layer interposed between the inner surface of the wall and at least the external surface of the drug layer located within the cavity, wherein the drug layer comprises a salt of an HIF-1 inhibitor, or a polymorph, solvate, hydrate, dehydrate, co-crystal, anhydrous, or amorphous form thereof. See U.S. Pat. No. 6,368,626, the entirety of which is incorporated herein by reference.

Another specific dosage form of the disclosure comprises: a wall defining a cavity, the wall having an exit orifice formed or formable therein and at least a portion of the wall being semipermeable; an expandable layer located within the cavity remote from the exit orifice and in fluid communication with the semipermeable portion of the wall; a drug layer located within the cavity adjacent the exit orifice and in direct or indirect contacting relationship with the expandable layer; the drug layer comprising a liquid, active agent formulation absorbed in porous particles, the porous particles being adapted to resist compaction forces sufficient to form a compacted drug layer without significant exudation of the liquid, active agent formulation, the dosage form optionally having a placebo layer between the exit orifice and the drug layer, wherein the active agent formulation comprises a salt of a HIF-1 inhibitor, or a polymorph, solvate, hydrate, dehydrate, co-crystal, anhydrous, or amorphous form thereof. See U.S. Pat. No. 6,342,249, the entirety of which is incorporated herein by reference.

Topical dosage forms of the disclosure include, but are not limited to, creams, lotions, ointments, gels, shampoos, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18.sup.th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466,465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of an HIF-1 inhibitor of the disclosure. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of an HIF-1 inhibitor can be used to further adjust the properties of the resulting composition

6. Kits

Typically, active ingredients of the pharmaceutical compositions of the disclosure are preferably not administered to a patient at the same time or by the same route of administration. This disclosure therefore encompasses kits which, when used by the medical practitioner, can simplify the administration of appropriate amounts of active ingredients to a patient.

A typical kit comprises a unit dosage form of a pharmaceutically acceptable salt of an HIF-1 inhibitor and optionally, a unit dosage form of a second pharmacologically active compound, such as anti-proliferative agent, or anti-cancer agent In particular, the pharmaceutically acceptable salt of an HIF-1 inhibitor is the sodium, lithium, or potassium salt, or a polymorph, solvate, hydrate, dehydrate, co-crystal, anhydrous, or amorphous form thereof.

A kit may further comprise a device that can be used to administer the active ingredient. Examples of such devices include, but are not limited to, syringes, drip bags, patches, and inhalers. Kits of the disclosure can further comprise pharmaceutically acceptable vehicles that can be used to administer one or more active ingredients (e.g, an HIF-1 inhibitor). For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

7. Examples

Class 1

Benzopyran Analogues A, See FIG. 1

To afford these analogues, the aldehyde derivative of the benzopyran moiety was synthesized followed by reductive amination and methylation of the resulting secondary amine.

The synthesis of class I analogues (See FIG. 1) began with compound 1 that was synthesized according to literature procedures. See Prado et al., Bioorgan. Med. Chem., 2007, 15, 2177-2186, hereby incorporated by reference. Reductive amination of 1 with several primary amines gave analogues 2. Methylation of secondary amine 2 with MeI and NaH generated analogues 3 (Scheme 1)

Scheme 1. Synthesis of benzopyran analogues A[a]

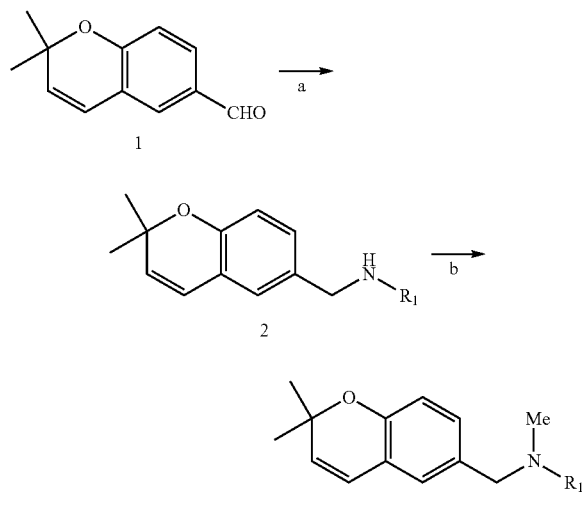

R$_1$ = 3,4-dimethoxyphenyl (2a, 3a), 2-pyridinyl (2b, 3b), 2,4-dimethylphenyl (2c, 3c), 4-carboxyphenyl (2d), 2-bromophenyl (2e), 2-fluorophenyl (2f)
[a]Reagents and Conditions: (a) R$_1$NH$_2$, ZnCl$_2$, NaCNBH$_3$, r.t., 60-70%; (b) MeI, NaH, THF, r.t., 50%.

Class 2

Benzopyran Analogues B

Reductive amination of aldehyde 1 with various aryl or alkyl amines afforded compound 4 that was subsequently converted to sulfonamides with various sulfonylchlorides to give analogues 5 (Scheme 2).

Scheme 2. Synthesis of benzopyran analogues B[a]

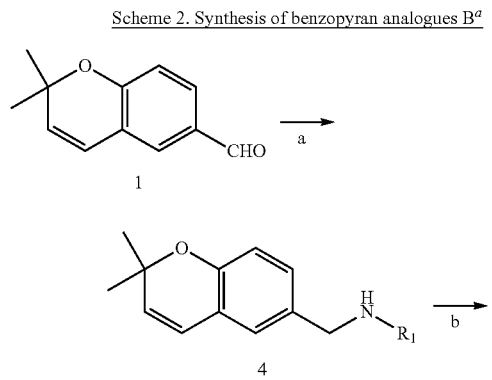

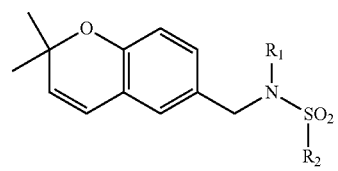

R$_2$ = 3,4-dimethoxyphenyl and
R$_1$ = isopropyl (5a), propargyl (5b), butyl (5c), t-butyl (5d), allyl (5e), 2-pyridinyl (5f), isobutyl (5g), cyclopentyl (5h), cyclopropyl (5i), cyclohexyl (5j)
R$_1$ = phenyl and
R$_2$ = 4-methoxyphenyl (5k), 2,4-dimethylphenyl (5l), 2,4-dichlorophenyl (5m), 2-trifluoromethoxy-4-bromophenyl (5n)
[a]Reagents and Conditions: (a) R$_1$NH$_2$, ZnCl$_2$, NaCNBH$_3$, r.t., 60-70%; (b) R$_2$SO$_2$Cl, Et$_3$N, DCM, r.t., 30-95%.

Class 3

2-Ethyl-2-methyl Benzopyran Analogues

For the synthesis of these analogues, O-alkylation of 4-hydroxybenzophenone 6 with 3-methylpentyn-3-ol afforded compound 7. Claisen rearrangement and re-aromatization of 7 by microwave irradiation yielded compound 8. Reductive amination of aldehyde 8 gave the secondary amine 9 that was converted to the corresponding sulfonamide 10 with 3,4-dimethoxybenzenesulfonyl chloride.

Scheme 3. Synthesis of 2-ethyl-2-methylbenzopyran analogue[a]

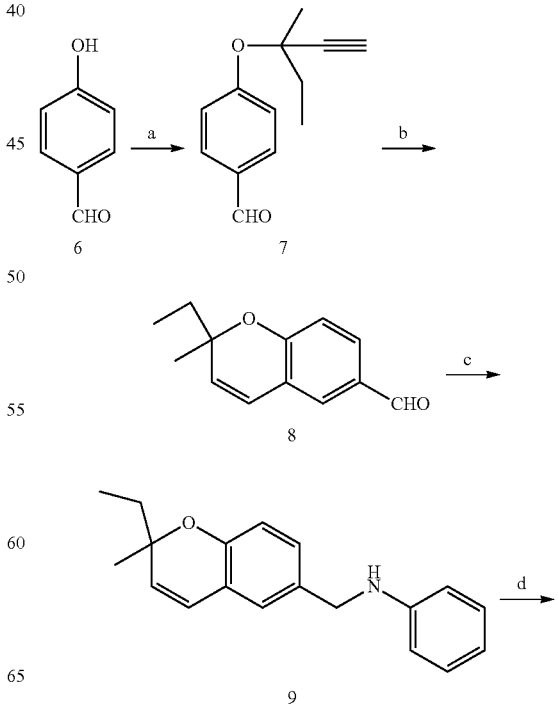

-continued

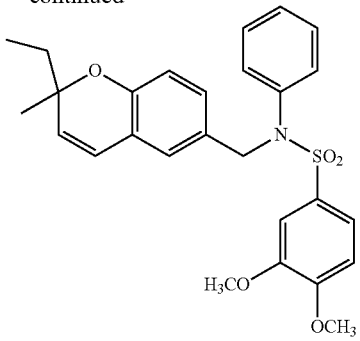

10

[a]Reagents and Conditions: (a) 3-Methyl-pent-1-yn-3-ol DBU, TFAA, CuCl, CH₃CN, 0° C. to r.t., 30%; (b) xylene, microwave (220 W, 200 torr, 120° C., 100 min); (c) aniline, ZnCl₂, NaCNBH₃, r.t., overnight, 42%; d) 3,4-dimethoxybenzylsulfonyl chloride, Et₃N, DCM, r.t., 24 h, 32%.

Class 4

Quinoline Analogues

Commercially available quinoline aldehyde 11 was subjected to reductive amination, followed by sulfonylation to afford compound 13 in 45% yield.

Scheme 4. Synthesis of quinoline analogue[a]

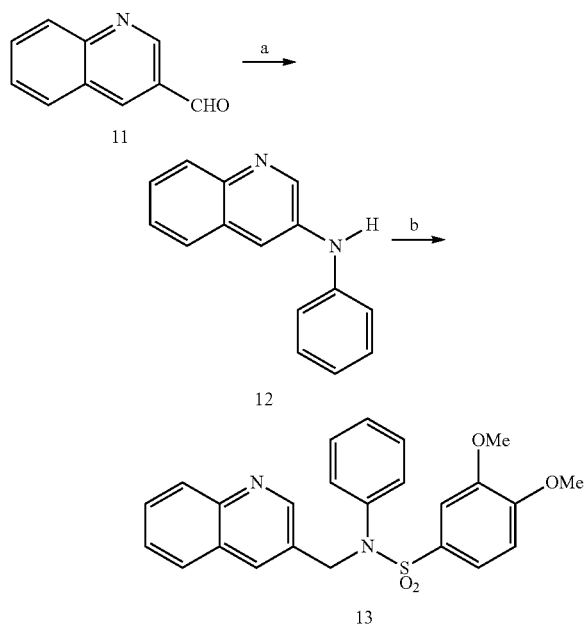

[a]Reagents and Conditions: (a) aniline, ZnCl₂, NaCNBH₃, r.t., 64%; (b) 3,4-dimethoxybenzylsulfonyl chloride, pyridine, r.t., 45%.

Class 5

Benzofuran Analogues

Additionally, the 2,2-dimethylbenzopyran ring (Region IV) of KCN-1 was replaced with a 2,2-dimethylbenzofuran ring (Scheme 5). Commercially available 2,2-dimethyl-2,3-dihydrobenzofuran-5-carbaldehyde 14 was subjected to reductive amination with various primary amines to give compound 15 and then sulfonylation with 3,4-dimethoxybenzenesulfonyl chloride to give analogues 16.

Scheme 5. Synthesis of benzofuran analogues[a]

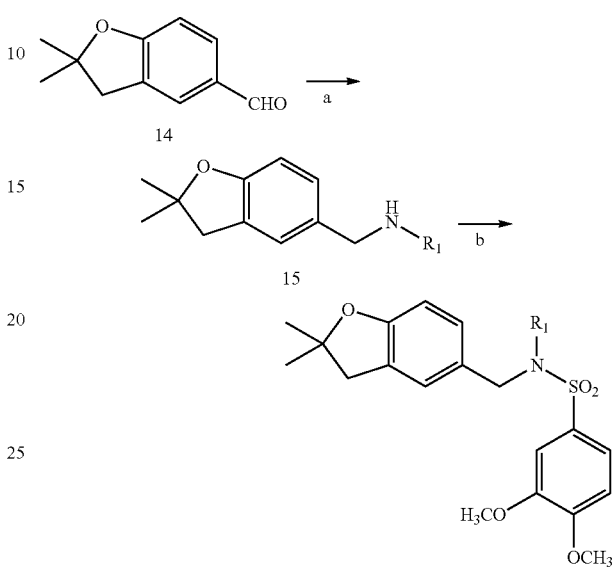

R₁ = phenyl (16a), cycloheptyl (16b), isopropyl (16c), butyl (16d), cyclohexyl (16e), cyclopentyl (16f)
[a]Reagents and Conditions: (a) R₁NH₂, ZnCl₂, NaCNBH₃, r.t., 2 h; (b) 3,4-dimethoxybenzenesulfonyl chloride, Et₃N, DCM, r.t., 20-42%.

Class 6

Pyranopyridines

The first of these compounds was the pyrano(2,3b)pyridines 20. The 2H-pyrano-[2,3b]-pyridine core 17 was synthesized as previously described. Evans & Short, Synthetic Commun. 1988, 18, 1111-1118. Formylation of 17 with BuLi and DMF gave compound 18. Reductive amination with aniline (19a) or cyclohexylamine (19b) followed by sulfonylation with 3,4-dimethoxybenzesulfonyl chloride afforded compounds 20a and 20b (Scheme 6).

Scheme 6. Synthesis of pyrano(2,3b)pyridine analogues[a]

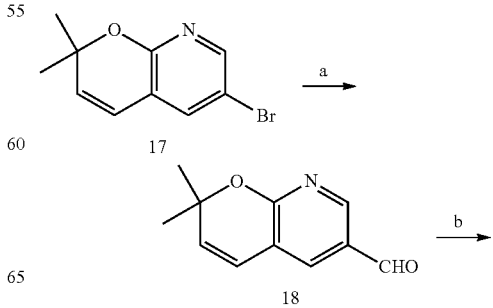

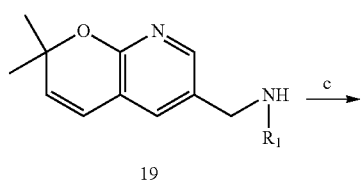

19

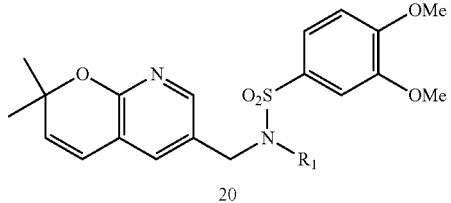

20

R₁ = phenyl (20a), cyclohexyl (20b)
[a]Reagents and Conditions: (a) (i) BuLi, -78° C. (ii). DMF, anh. ether, 31%; (b) R₁NH₂, ZnCl₂, NaCNBH₃, MeOH, 49%; (c) 3,4-diethoxybenzenesulfonyl chloride, Et₃N, DCM, r.t., 43-60%.

Another set of analogues in this class was the pyrano(3,2b) pyridines that were prepared using the following procedure: O-alkylation of commercially available 2-bromo-5-hydroxypyridine 22 followed by Claisen rearrangement and formylation gave compound 24 with a 23% overall yield for the two steps. Subsequent reductive amination of 24 and then reaction of secondary amine 25 with various sulfonyl chlorides afforded analogues 26 (Scheme 7).

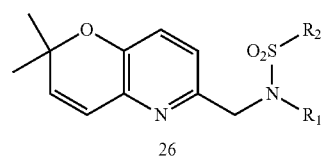

26

R₂ = 3,4-dimethoxyphenyl and
R₁ = phenyl (26a), butyl (26b), 3,4-dimethoxyphenyl (26c), cyclopentyl (26d), cyclohexyl (26e), tetrahydranapthyl (26f), cycloheptyl (26g), cyclooctyl (26h), cyclobutyl (26i)

R₁ = phenyl and
R₂ = cyclohexyl (26j), isopropyl (26k), butyl (26l), propyl (26m), isobutyl (26n), 4-biphenyl (26o), propyl (26p), benzodioxolyl (26q), 2,3-dihydrobenzo(1,4)dioxinyl (26r), 4-fluorophenyl (26s)

[a]Reagents and Conditions: (a) 2-methylbut-3-yn-2-ol, TFAA, DBU, CH₃CN; (b) xylene, microwave heating 120° C., 30 min, 23% for 2 steps; (c) 1. BuLi, 2. DMF, anhydrous THF, 23%; (d) R₁NH₂, ZnCl₂, NaCNBH₃, MeOH; (d) R₂SO₂Cl, Et₃N, DCM, 40-65% for 2 steps.

To synthesize these analogues, 2-hydroxy-5-methylpyridine 27 was brominated to afford compound 28. N-oxidation of 28 with m-CPBA gave product 29 in 70% yield. Rearrangement of 29, facilitated by TFAA afforded compound 30. O-alkylation of 30 with 3-chloro-3-methyl-1-butene followed by Claisen rearrangement gave compound 32. Substitution of the primary alcohol 32 with bromine followed to give 33. Subsequent nucleophilic substitution of 33 with various primary amines followed by removal of the bromine with BuLi afforded compound 35. Next sulfonylation of 35 with aryl sulfonylchlorides resulted in analogues 36 (Scheme 8).

Scheme 7. Synthesis of pyrano(3,2b)pyridine analogues[a]

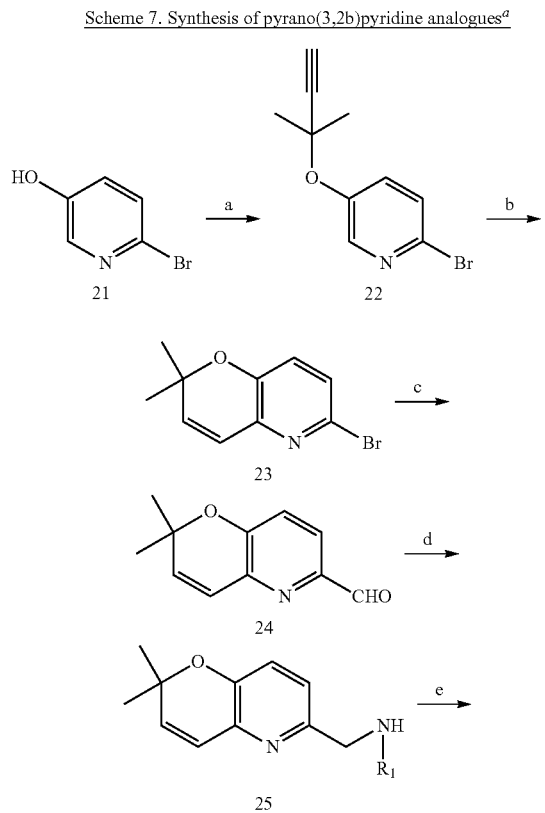

Scheme 8. Synthesis of pyrano(2,3c) pyridine analogues[a]

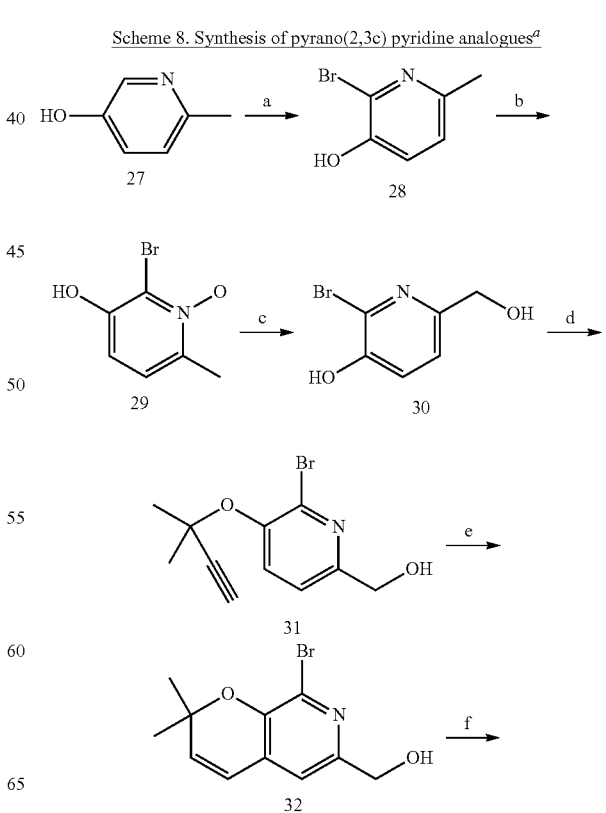

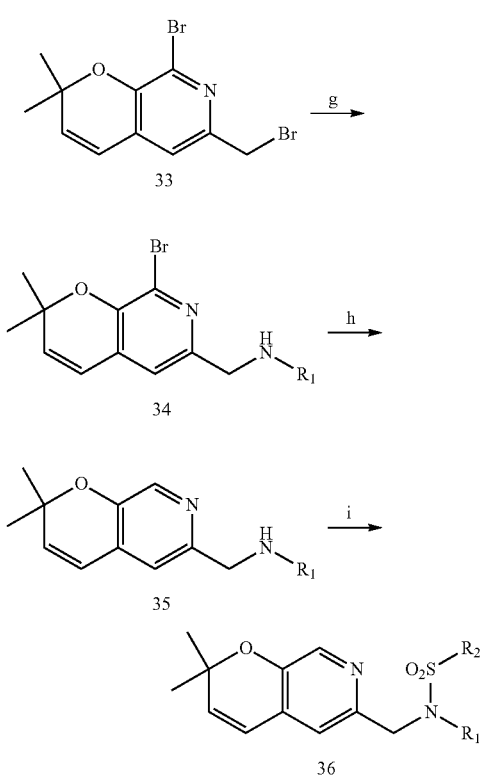

$R_1$ = phenyl and $R_2$ = 4-methoxyphenyl (36a), 4-nitrophenyl (36b)
$R_1$ = cyclohexyl and $R_2$ = 4-isopropylphenyl (36c), 3,4-dimethoxyphenyl (36d)
[a]Reagents and Conditions: (a) Br$_2$, pyridine, 0° C., 74%; (b) m-CPBA, THF, 70%; (c) 1. TFAA, 2. MeOH, 30%; (d) 3-chloro-3-methyl-1-butene, K$_2$CO$_3$, KI, CuCl$_2$, acetone, 57%; (e) CuCl, toluene, microwave heating (200 W, 120° C., 1 hour), 70%; (f) CBr$_4$, PPh$_3$, DCM, 40%; (g) DIEA, DMF, 60-78%; (h) BuLi, THF, -78° C., 50-70% (i) R$_2$SO$_2$Cl, pyridine, r.t., 70-89%.

Class 7

Amide Analogue

The sulphonamide of compound 26a was replaced with an amide group. The amide group is a common bioisostere for sulfonamide and may enhance activity. In this case, the previously synthesized 25a was reacted with 3,4-dimethoxybenzoyl chloride in the presence of triethylamine to give the product 37 with a 98% yield (Scheme 9).

Scheme 9. Synthesis of compound 37

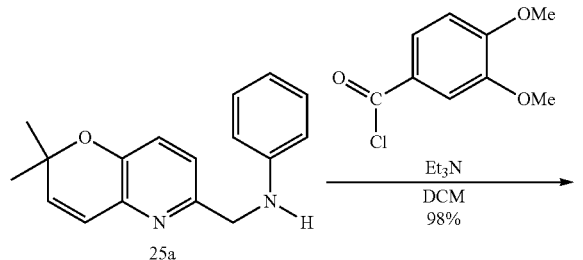

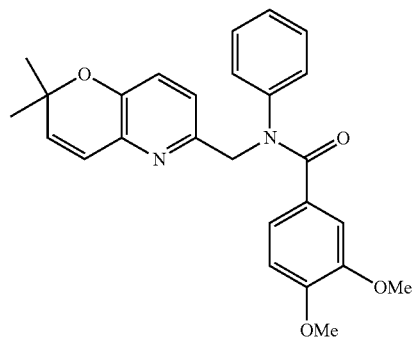

Biological Activity

The synthesized analogues were evaluated for their potential to inhibit HIF-1-mediated transcription under hypoxia (1% O$_2$) using a human glioma cell line LN229-HRE-Lux, which stably expresses a hypoxia-responsive luciferase reporter gene (Table 1-9). The IC$_{50}$ values of all compounds were calculated based on a concentration curve testing of compounds at 0, 1, 5, 10 and 25 μM. The compounds were tested in single (n=1) or multiple (n>1) independent experiments each carried out in quadruplicate. KCN-1 (N-((2,2-dimethyl-2H-chromen-6-yl)methyl)-3,4-dimethoxy-N-phenylbenzenesulfonamide) had an IC$_{50}$ of 700±400 nM (n=26) using this cell-based reporter assay.

Class I (benzopyran A) analogues were designed to probe the importance of the sulfonyl group. For secondary amine compounds 2a-2f, only 2a and 2b had IC$_{50}$ values below 10 μM, the others were higher than 25 μM. A typical compound in that series was the 3,4-dimethoxyphenyl derivative 2a with an IC$_{50}$ of 3.0 μM. Analogues 3a-3c showed similar IC$_{50}$ values as their secondary amine counterparts 2a-2c, with the exception of the 2,4-dimethoxyphenyl derivative 3c that had an IC$_{50}$ of 2.6 μM.

TABLE 1

Structures and activities of analogues 2a to 3c

| Compound | $R_1$ | $R_2$ | IC$_{50}$ (μM) |
|---|---|---|---|
| 2a | H | 3,4-dimethoxyphenyl | 3.0 |
| 2b | H | 2-pyridyl | 8.5 |

TABLE 1-continued

Structures and activities of analogues 2a to 3c

| Compound | R₁ | R₂ | IC$_{50}$ (μM) |
|---|---|---|---|
| 2c | H | 2,4-dimethylphenyl | >25 |
| 2d | H | 4-COOH-phenyl | >25 |
| 2e | H | 2-Br-phenyl | >25 |
| 2f | H | 2-F-6-methylphenyl | >25 |
| 3a | Me | 3,4-dimethoxyphenyl | 5.0 |
| 3b | Me | 2-pyridyl | 8.4 |
| 3c | Me | 2,4-dimethylphenyl | 2.6 |

Next, Region II (FIG. 1) of the molecule was probed with various alkyl and aryl substituent (5a-5k). Typical compounds of this group were the propargyl derivative 5b, iso-butyl derivative 5g and the cyclopropyl derivative 5i with IC$_{50}$ values of 1.3, 1.6 and 1.5 μM respectively. In general, longer branched alkyl chains such as the iso-butyl group of 5g (1.6 μM) tended to do better than long unbranched chains such as the butyl group of 5c (3.3 μM) or shorter branched chains as the tert-butyl group of 5d (3.5 μM). Also, alkyl rings smaller than 6 carbons were better tolerated.

TABLE 2

Structures and activities of analogues 5a-

| Compound | R₁ | IC$_{50}$ (μM) |
|---|---|---|
| 5a | iso-propyl | 3.1 |
| 5b | propargyl | 1.3 |
| 5c | butyl | 3.3 |
| 5d | tert-butyl | 3.5 |
| 5e | allyl | 3.4 |
| 5f | iso-butyl | 1.6 |
| 5g | cyclopentylmethyl | 0.5 |
| 5h | cyclopropyl | 1.5 |
| 5i | cyclohexyl | 4.0 |

Compound 5k-5u, were modified at region III of with various aryl substitutions (Table 3). Typical compounds in this group were the 4-methoxyphenyl substituted 5k and 2,4-dimethylphenylsubstituted 5i with IC$_{50}$ values of 0.6 and 0.5 μM respectively. The 4-bromosubstituted analogue has an IC$_{50}$ of 5.5 μM.

TABLE 3

Structures and activities of analogues 5j-5m [a]

| Compound | R$_2$ | IC$_{50}$ (μM) |
|---|---|---|
| 5j | 4-OMe-phenyl | 0.6 |
| 5k | 3,5-dimethylphenyl | 0.5 |
| 5l | 2,4-dichlorophenyl | 2.1 |
| 5m | F$_3$CO, Br-substituted phenyl | >25 |

Compound 10, represented a change to region IV, had an IC$_{50}$ of 2.2 μM (Table 4). In the case of compound 13, replacement of the benzopyran ring with a quinoline ring led to compound with an IC$_{50}$ of 3.5 μM (Table 4).

TABLE 4

Structures and activities of analogues 10 and 13 [a]

| Compound | R$_1$ | IC$_{50}$ (μM) |
|---|---|---|
| 10 | ethyl-dimethyl-benzopyran | 3.1 |
| 13 | quinoline | 1.3 |

The benzofuran derivatives 16 afforded some potent compounds (Table 5). The foreseeable benefit of the benzofuran structure of 16 is that it eliminates the double bond on the pyran ring. Since that double bond may be susceptible to epoxidation in vivo and thereby introduce toxicity, the benzofuran ring may be a better alternative. The ring size of the cycloalkyl derivatives seems to have an effect on activity. A comparison of the cycloheptyl ring of 16b (9.1 μM), the cyclohexyl ring of 16e (8.2 μM) and the cyclopentyl ring of 16f (0.4 μM) seems to suggest that smaller rings (ring size 5 or smaller), tend to be more favorable than large rings (6 carbons or more). This is similar to the trend seen with the benzopyran analogues B (class 2).

TABLE 5

Structures and activities of analogues 16a-f [a]

| Compound | R$_1$ | IC$_{50}$ |
|---|---|---|
| 16a | phenyl | 0.5 |

TABLE 5-continued

Structures and activities of analogues 16a-f [a]

| Compound | R₁ | IC₅₀ |
|---|---|---|
| 16b | cycloheptyl | 9.1 |
| 16c | isopropyl | 1.5 |
| 16d | n-pentyl | 0.6 |
| 16e | cyclohexyl | 8.2 |
| 16f | cyclopentyl | 0.4 |

The first of the pyranopyridine analogues was Class 6a, the pyrano(2,3b)pyridines. Two compounds were synthesized in this class. Compound 20a showed activity with an IC$_{50}$ of 2.5 µM.

TABLE 6

Structures and activities analogues 20 [a]

| compound | R₁ | IC50 (µM) |
|---|---|---|
| 20a | phenyl | 2.5 |

TABLE 6-continued

Structures and activities analogues 20 [a]

| compound | R₁ | IC50 (µM) |
|---|---|---|
| 20b | cyclohexyl | >25 |

The next group of compounds in this class was the pyrano(3,2b)pyridine (class 6b). Compounds 26a-26k were modified at region I (FIG. 1) with various alkyl and aryl amines. Phenyl derivative 26a had an IC$_{50}$ of 1.3 Cyclobutyl derivative 26i with an IC$_{50}$ of 0.25 µM consistently showed ~3-fold higher potency than KCN-1. Comparing all the cylcoalkyl analogues, the general trend remained about the same as that of other series, in that smaller rings (<6 carbons) tend to have better activity than larger ring derivatives (>6 carbons).

Additionally, these pyrano(3,2b)pyridines 26k-26t were also modified at region III (FIG. 1) with alkyl and aryl sulphonyl derivatives. (Table 8). The cyclohexyl group was well tolerated in this position leading to derivative 26i, with an IC$_{50}$ of 0.4 µM. Also noted is the quinoline derivative 26s that had an IC$_{50}$ of 0.9 µM.

TABLE 7

Structures and activities of analogues 26a -26j [a]

| Compound | R₁ | IC₅₀ (µM) |
|---|---|---|
| 26a | phenyl | 1.3 |
| 26b | n-butyl | 0.9 |
| 26c | 3,4-dimethoxyphenyl | >25 |

TABLE 7-continued

Structures and activities of analogues 26a-26j [a]

| Compound | R₁ | IC$_{50}$ (μM) |
|---|---|---|
| 26d | cyclopentyl | 0.6 |
| 26e | cyclohexyl | 0.8 |
| 26f | 8-methyl-tetrahydronaphthalenyl | 6.2 |
| 26g | cycloheptyl | 6.6 |
| 26h | cyclooctyl | 0.7 |
| 26i | cyclobutyl | 0.25 |
| 26j | 4-fluorophenyl | 5.7 |

[a] Results were from single runs

TABLE 8

Structure and activities of analogues 26k-26t [a]

| Compound | R₂ | IC$_{50}$ (μM) |
|---|---|---|
| 26k | cyclohexyl | 0.4 |
| 26l | isobutyl | 13.4 |
| 26m | tert-butyl | >25 |
| 26n | n-butyl | 5.0 |
| 26o | n-butyl (branched) | 6.4 |
| 26p | isobutyl | 0.9 |
| 26q | 4-biphenyl | 3.4 |
| 26r | methylenedioxyphenyl | 6.5 |
| 26s | 8-quinolinyl | 0.9 |
| 26t | 2,3-dihydrobenzodioxinyl | 0.9 |

[a] Results were from single runs

The third group of compounds in class 6 was the pyrano (2,3c)pyridinyl derivatives (class 6c) (Table 9). Derivatives 36a, 36b and 36c had IC$_{50}$ values of 1.42, 1.80 and 1.08 μM respectively.

TABLE 9

Structures and activities analogues 36 [a]

| compound | R₁ | R₂ | IC₅₀ (μM) |
|---|---|---|---|
| 36a | phenyl | 4-OMe-phenyl | 1.4 |
| 36b | phenyl | 4-NO₂-phenyl | 1.8 |
| 36c | cyclohexyl | 4-isopropyl-phenyl | 1.1 |
| 36d | cyclohexyl | 3,4-dimethoxy-phenyl | 5.8 |

[a] Results were from single runs

The sulphonamide group was replaced with an amide group to see what effect this modification would have on activity (FIG. 3). This amide group can be incorporated in future modifications of the compound.

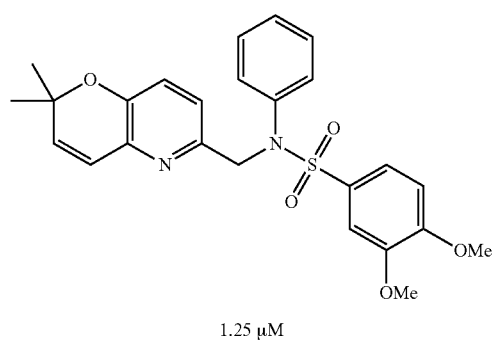

26a 1.25 μM

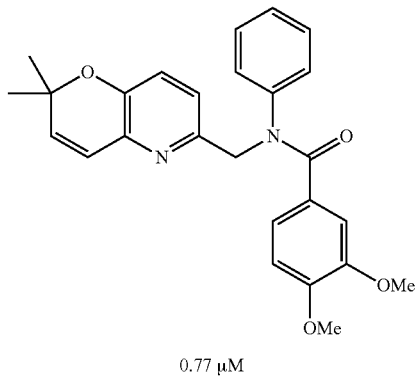

37

0.77 μM

FIG. 3. Comparison of Structures and Activities of 26a and 37

Assay

LN229-HRE-luciferase human glioblastoma cells were used to perform the assay. These cells contain stably integrated reporter construct (V6R) made of six copies of the HIF responsive element derived from the VEGF gene as described in Post & Van Meir, Gene Ther., 2001, 8, 1801-7, hereby incorporated by reference. 48-well plates were seeded with $3.10^4$ cells per well and incubated under normoxic conditions for 24 h. Cells were then pre-treated with different concentrations of KCN-1 or its analogues for 1 h and then transferred to hypoxic conditions. After 24 h, media was aspirated, cells were lysed and reporter activity was measured in the lysate using Luciferase Assay System (Promega, Madison, Wis.) with 20/20ⁿ Luminometer (Promega).

Chemistry

Commercial chemicals and solvents were typically reagent grade and were used without further purification unless otherwise indicated. Microwave heating was performed in a single-mode microwave cavity of a Discover Synthesis System (CEM corp.) and microwave-irradiated reactions were conducted in a heavy walled glass vials sealed with Teflon septa. $^1$H NMR and $^{13}$C NMR were recorded at 400 MHz and 100 MHz respectively on a Bruker 400 NMR spectrometer with TMS or deuterated solvent as the internal standard. Coupling constants are in Hz. Mass Spectral analysis was performed by the Mass Spectrometry Facilities at Georgia State University. The purities of tested compounds were assessed as being at least 95% with analytical HPLC, which was performed using a C18 5 μm (250×4.6 mm) column at 254 nm and eluted with a gradient of 70-80% solvent B (methanol) in solvent A (water) at 0.8 mL/min.

General Procedure for Reductive Amination for Synthesis of 2a-2f

To a solution of 2,2-dimethyl-2H-chromene-6-carbaldehyde 1 (1 equiv.) in methanol was added the amine (2 equiv.), sodium cyanoborohydride (2 equiv.) and zinc chloride (anhydrous) (2 equiv.). The reaction was stirred overnight, then the solvent removed by rotary evaporation and 1M NaOH added to the residue. The organic layer was extracted with ethyl acetate or DCM (×2), dried over magnesium sulfate and concentrated in vacuo. The crude product was purified by flash column chromatography (silica gel).

(3,4-Dimethoxy-phenyl)-(2,2-dimethyl-2H-chromen-6-ylmethyl)-amine (2a). Yield: 60%. $^1$H NMR (CDCl₃): δ 7.09 (dd, J=8.2, 2.1 Hz, 1H), 6.99 (d, J=2.0 Hz, 1H), 6.74 (d, J=8.4 Hz, 2H), 6.30 (s, 1H), 6.30-6.24 (m, 1H), 6.17 (dd, J=8.5, 2.6 Hz, 1H), 5.61 (d, J=9.8 Hz, 1H), 4.15 (s, 2H), 3.81 (t, J=6.2 Hz, 6H), 1.43 ppm (s, 6H). $^{13}$C NMR (CDCl₃): δ 152.2, 150.0, 143.3, 141.6, 131.6, 131.1, 128.4, 125.7, 122.2, 121.4, 116.4, 113.3, 103.6, 99.0, 76.2, 56.7, 55.7, 48.8, 28.1 ppm. HRMS (ESI) m/z calcd for $C_{20}H_{23}NO_3$ [(M+H)$^+$]; 326.1756. found: 326.1750, calc.: HPLC, ret. time=9.41 min, 99.5%

(2,2-Dimethyl-2H-chromen-6-ylmethyl)-methyl-pyridin-2-yl-amine (2b). Yield: 60%. $^1$H NMR (CDCl$_3$): δ 8.10-8.08 (m, 1H), 7.77-7.35 (m, 1H), 7.08-7.07 (m, 1H), 7.00-6.96 (m, 1H), 6.77-6.72 (m, 1H), 6.50-6.58 (m, 1H), 6.36 (d, J=8.4 Hz, 1H), 6.28 (d, J=9.6 Hz, 1H), 4.80 (s, br, 1H), 4.40 (s, 2H), 1.41 ppm (s, 1H). HRMS (ESI) m/z calcd for $C_{17}H_{18}N_2O$ [(M+H)$^+$] 267.149. found: 267.1505. ret. time=12.8 min, 99.6%.

(2,2-Dimethyl-2H-chromen-6-ylmethyl)-(2,4-dimethyl-phenyl)-amine (2c). Yield: 69%. $^1$H NMR (CDCl$_3$): δ 7.10 (dd, J=6.0 Hz, 2.4 Hz, 1H), 6.99 (d, J=8.0 Hz), 6.92-6.90 (m, 1H), 6.74 (d, J=8.4 Hz, 1H), 6.54 (d, J=7.6 Hz, 1H), 6.30 (d, J=9.6 Hz, 1H) 4.21 (s, 2H), 2.23 (s, 3H), 2.12 (s, 3H), 1.43 ppm (s, 6H). MS (ESI) m/z 292 [(M+H)$^+$]. HPLC, ret. time=20.84 min, 97.9%

4-[(2,2-Dimethyl-2H-chromen-6-ylmethyl)-amino]-benzoic acid (2d). Yield: 58%. $^1$H NMR ((CD$_3$)$_2$SO): δ 1.35 (s, 6H), 4.17 (d, J=5.5 Hz, 2H), 5.72 (d, J=9.8 Hz, 1H), 6.37 (d, J=9.8 Hz, 1H), 6.54 (d, J=7.7 Hz, 2H), 6.68 (d, J=8.2 Hz, 1H), 7.03 (s, 1H), 7.08 (s, 1H), 7.71 ppm (s, 2H). HRMS (ESI) m/z calcd for $C_{19}H_{19}NO_3$ [(M–H)$^+$] 308.1287. found: 308.1276.

(2-Bromo-phenyl)-(2,2-dimethyl-2H-chromen-6-ylmethyl)-amine (2e). Yield: 11%. $^1$H NMR (CDCl$_3$): δ 7.43 (d, J=7.8 Hz, 1H), 7.20-7.04 (m, 2H), 6.97 (s, 1H), 6.75 (d, J=8.2 Hz, 1H), 6.62 (d, J=8.0 Hz, 1H), 6.58 (d, J=7.1 Hz, 1H), 6.30 (d, J=9.8 Hz, 1H), 5.61 (d, J=9.8 Hz, 1H), 4.63 (s, 1H), 4.26 (d, J=5.3 Hz, 2H), 1.43 ppm (s, 6H). $^{13}$C NMR (CDCl$_3$): δ 152.3, 144.9, 132.3, 131.1, 130.7, 128.1, 125.4, 122.2, 121.4, 117.9, 116.5, 111.6, 109.6, 76.3, 47.6, 28.0 ppm. HRMS (ESI) m/z calcd for $C_{18}H_{18}NOBr$ [(M+H)$^+$] 344.0650. found: 344.0663. HPLC, ret. time=19.71 min, 97.9%

(2,2-Dimethyl-2H-chromen-6-ylmethyl)-(2-fluoro-phenyl)-amine (2f). Yield: 71%. $^1$H NMR (CDCl$_3$): δ 7.10 (dd, J=6.0, 2.0 Hz, 1H), 6.99-6.94 (m, 3H), 6.76-6.56 (m, 3H), 6.29 (d, J=9.6 Hz, 1H), 5.61 (d, J=9.6 Hz, 1H), 4.23 (s, 3H), 1.43 ppm (s, 6H). $^{13}$C NMR (CDCl$_3$): δ 152.4, 143.9, 138.1, 136., 130.9, 128.3, 128.2, 127.5, 127.1, 124.7, 123.5, 122.3, 121.2, 116.2, 77.4, 28.1, 21.5 ppm. HRMS 0(ESI) m/z calcd for $C_{18}H_{18}NOF$ [(M+H)$^+$]284.1451. found: 284.1442. HPLC: ret. time=16.55 min, 97.3%

General Procedure for synthesis of 3a-3c by methylation of secondary amines 2a, 2b and 2c respectively. A solution of secondary amine 2 (1 equiv.) in THF was added to a flask containing NaH (2 equiv) in THF. After 5 min, MeI (2 equiv) was added and the reaction stirred overnight. The reaction mixture was quenched with water and diluted with ethyl acetate. The organic layer was washed with water and brine, dried over MgSO$_4$ and concentrated in vacuo. The crude product was purified by flash column chromatography (silica gel).

(3,4-Dimethoxy-phenyl)-(2,2-dimethyl-2H-chromen-6-ylmethyl)-methylamine (3a). Yield: 60%. $^1$H NMR (CDCl$_3$): δ 6.98 (dt, J=7.2, 3.6 Hz, 1H), 6.87 (s, 1H), 6.78 (d, J=8.7 Hz, 1H), 6.73 (s, 1H), 6.43 (d, J=8.7 Hz, 1H), 6.27 (d, J=10.1 Hz, 2H), 5.59 (d, J=9.8 Hz, 1H), 4.31 (s, 2H), 3.82 (d, J=2.2 Hz, 6H), 2.89 (s, 3H), 1.42 ppm (s, 6H). $^{13}$C NMR (CDCl$_3$): δ 149.7, 145.6, 131.2, 130.9, 127.9, 125.1, 122.3, 121.3, 116.3, 113.0, 104.8, 99.5, 77.4, 77.0, 76.7, 76.2, 57.6, 56.7, 55.8, 38.9, 28.0 ppm. HRMS (ESI) m/z calcd for $C_{21}H_{25}NO_3$ [(M+H)$^+$] 340.1913. found: 340.1900.

(2,2-Dimethyl-2H-chromen-6-ylmethyl)-methyl-pyridin-2-yl-amine (3b). Yield: 81%. $^1$H NMR (CDCl$_3$): δ 8.21 (m, 1H), 7.45 (m, 1H), 6.99 (d, J=8.5 Hz, 1H), 6.86 (s, 1H), 6.72 (d, J=8.0 Hz, 1H), 6.52-6.59 (m, 2H), 6.28 (d, J=10 Hz, 1H), 5.60 (d, J=10 Hz, 1H), 4.70 (s, 2H), 3.06 (s, 3H), 1.44 ppm (s, 6H). $^{13}$C NMR (CDCl$_3$): δ 151.9, 148.0, 137.3, 130.9, 130.8, 127.8, 125.0, 122.4, 121.3, 116.3, 11.7, 105.8, 76.1, 52.6, 36.0, 28.0 ppm. HRMS (ESI) m/z calcd for: $C_{18}H_{20}N_2O_3$ [M+H)+] 281.1654. found: 281.1659. HPLC, ret. time=16.55, 97.3%.

(2,2-Dimethyl-2H-chromen-6-ylmethyl)-(2,4-dimethylphenyl)-methyl-amine (3c). Yield: 48%. $^1$H NMR (CDCl$_3$): d 7.13 (dd, J=2.0, 6.0 Hz, 1H), 7.05-7.00 (m, 4H), 6.75 (d, J=8.0 Hz, 1H), 6.34 (d, J=9.6 Hz, 1H), 5.63 (d, J=9.2 Hz, 1H), 3.88 (s, 2H), 2.55 (s, 3H), 2.40 (s, 3H), 2.31 (s, 3H), 1.45 ppm (s, 6H). MS (ESI) m/z 308 [(M+H)$^+$].

General Procedure for Synthesis of 5a-5m by Alkyl Sulfonylation.

To a solution of 1 (1 eq) in methanol was added the primary amine (1 equiv.), ZnCl$_2$ (2 equiv.) and the reaction was stirred at room temperature for 2 h. Then NaCNBH$_3$ (2 equiv.) was added and the reaction was stirred at room temperature overnight. The solvent was removed by rotary evaporation and EtOAc was added to the residue. The solid was filtered through Celite and the filtrate washed with 1M NaOH, water and brine. The organic layer was dried over MgSO$_4$ and concentrated under reduced pressure. The crude secondary amine product 4 was used without further purification.

To a solution of the secondary amine 4 (1 equiv.) in DCM was added triethylamine (3 equiv.) and the sulfonylchloride (1.5 equiv.). The reaction was stirred for 24 to 48 h. Then water was added and the organic layer extracted with DCM, dried over MgSO$_4$, concentrated under reduced pressure, and purified by flash column chromatography.

N-(2,2-Dimethyl-2H-chromen-6-ylmethyl)-N-isopropyl-3,4-dimethoxy-benzenesulfonamide (5a). Yield: 58%. $^1$H NMR (CDCl$_3$): δ 7.39 (dd, J=6.4, 2.0 Hz, 1H), 7.22 (d, J=2.0 Hz, 1H), 7.07 (dd, J=6.0, 2.0 Hz, 1H), 7.00 (d, J=2.0 Hz, 1H), 6.90 (t, J=8.6 Hz, 1H), 6.69 (d, J=8.2 Hz, 1H), 6.28 (d, J=9.8 Hz, 1H), 5.60 (d, J=9.8 Hz, 1H), 4.39-4.19 (m, 2H), 4.23-4.02 (m, 1H), 4.04-3.73 (m, 6H), 1.41 (s, 6H), 1.05 ppm (d, J=7.2 Hz, 6H). $^{13}$C NMR (CDCl$_3$): δ 152.2, 152.2, 149.0, 133.2, 131.0, 130.8, 128.6, 126.0, 122.3, 121.2, 120.8, 116.1, 110.5, 109.6, 76.3, 56.2, 56.1, 50.0, 46.0, 27.9, 21.3 ppm. HRMS (ESI) m/z calcd for $C_{23}H_{29}NO_5S$ [(M+Na)$^+$] 451.1664. found: 451.1651. HPLC: ret. time=11.76 min, 97.2%.

N-(2,2-Dimethyl-2H-chromen-6-ylmethyl)-3,4-dimethoxy-N-prop-2-ynyl-benzenesulfonamide (5b). Yield: 95%. $^1$H NMR (CDCl$_3$): δ 7.53 (dd, J=2.0 Hz, 1H), 7.38 (d, J=2.0 Hz, 1H), 7.09-7.07 (m, 1H), 7.00-6.96 (m, 2H), 6.74 (d, J=8.0 Hz, 1H), 6.31 (d, J=9.6 Hz, 1H), 5.64 (d, J=9.6 Hz, 1H), 4.24 (s, 1H), 4.01-3.96 (m, 7H), 1.59 (s, 2H), 1.43 ppm (s, 6H). HRMS (ESI) m/z calcd for $C_{23}H_{25}NO_5S$ [(M+Na)$^+$] 450.1351. found: 450.1352. HPLC, ret. time=10.65 min, 96.61%

(N-Butyl-N-(2,2-dimethyl-2H-chromen-6-ylmethyl)-3,4-dimethoxy-benzenesulfonamide(5c). Yield: 55%. $^1$H NMR (CDCl$_3$): δ 7.46 (dd, J=6.4, 2.1 Hz, 1H), 7.28 (m, 1H), 7.00-6.89 (m, 2H), 6.71 (d, J=8.0 Hz, 1H), 6.27 (d, J=10.0 Hz, 1H), 5.63 (d, J=9.6 Hz, 1H), 4.23 (s, 1H), 3.97-3.92 (m, 6H), 3.10 (t, J=7.6 Hz, 2H), 1.43 (s, 6H), 1.38-1.16 (m, 6H), 0.79 ppm (t, J=7.6 Hz, 3H). $^{13}$C NMR (CDCl$_3$): δ 152.3, 149.0, 132.2, 131.1, 129.1, 128.5, 126.4, 122.1, 121.3, 121.0, 116.2, 110.6, 109.8, 76.3, 56.2, 56.2, 51.1, 47.4, 30.0, 27.9, 19.9, 13.6 ppm. HRMS (ESI) m/z calcd for $C_{24}H_{31}NO_5S$+Na 468.1821. found: 468.1815. HPLC: ret. time=14.0 min, 96.3%

N-tert-Butyl-N-(2,2-dimethyl-2H-chromen-6-ylmethyl)-3,4-dimethoxy-benzenesulfonamide (5d). Yield: 49%. $^1$H NMR (CDCl$_3$): δ 7.41 (dd, J=8.5, 2.1 Hz, 1H), 7.22-7.12 (m, 2H), 7.06 (d, J=2.1 Hz, 1H), 6.87 (d, J=8.5 Hz, 1H), 6.74 (t, J=9.7 Hz, 1H), 6.30 (t, J=8.9 Hz, 1H), 5.62 (t, J=9.5 Hz, 1H), 4.56 (s, 2H), 3.94 (d, J=13.4 Hz, 3H), 3.85 (d, J=14.6 Hz, 3H), 1.48-1.39 (m, 6H), 1.33 ppm (s, 9H). MS (ESI) m/z 468 [(M+Na)$^+$]. HPLC: ret. time=13.2 min, 96.3%.

N-Allyl-N-(2,2-dimethyl-2H-chromen-6-ylmethyl)-3,4-dimethoxy-benzenesulfonamide (5e). Yield: 53%. $^1$H NMR (CDCl$_3$): δ 7.48 (dd, J=8.4, 2.2 Hz, 1H), 7.29 (t, J=2.3 Hz, 1H), 7.01-6.91 (m, 2H), 6.88 (d, J=2.1 Hz, 1H), 6.72 (t, J=9.7 Hz, 1H), 6.29 (d, J=6.4 Hz, 1H), 5.64 (t, J=10.6 Hz, 1H), 5.53 (ddt, J=16.7, 10.2, 6.5 Hz, 1H), 5.09 (ddd, J=18.4, 13.6, 1.3 Hz, 2H), 4.28 (d, J=25.4 Hz, 2H), 4.03-3.95 (m, 3H), 3.95-3.88 (m, 3H), 3.84-3.72 (m, 2H), 1.44 ppm (s, 6H). $^{13}$C NMR (CDCl$_3$): δ 152.6, 152.4, 149.1, 132.4, 132.4, 131.9, 129.4, 127.9, 126.6, 122.1, 121.3, 121.1, 199.2, 116.2, 110.6, 109.8, 76.4, 56.2, 56.18, 49.6, 49.2, 28.0 ppm. EI probe: M$^+$ 429. HPLC: ret. time=11.9 min, 97.0%

N-(2,2-Dimethyl-2H-chromen-6-ylmethyl)-3,4-dimethoxy-N-(3-methyl-butyl)-benzenesulfonamide (5f). Yield: 31%. $^1$H NMR (CDCl$_3$): δ 7.44 (dd, J=6.4, 2.0 Hz), 7.29-7.28 (m, 1H), 6.96-6.94 (m, 2H), 6.83 (s, 1H), 6.24 (d, J=10.0 Hz, 1H), 5.62 (d, J=10.0 Hz, 1H), 3.97-3.92 (m, 6H), 2.90 (d, J=7.6 Hz, 2H), 1.75 (sep, J=6.8 Hz, 1H), 1.43 (s, 6H), 0.792-0.779 ppm (m, 6H). $^{13}$C NMR (CDCl$_3$): δ 152.5, 152.3, 149.0, 132.1, 131.1, 129.2, 128.5, 126.5, 122.1, 121.1, 116.1, 110.5, 109.9, 76.3, 56.2, 56.2, 55.8, 52.1, 27.9, 26.8, 20.0 ppm. HRMS (ESI) m/z calcd for C$_{24}$H$_{31}$NO$_5$S 468.1821 [(M+Na)+]. found: 468.1801. HPLC: ret. time=13.92 min, 97.5%.

N-Cyclopentyl-N-(2,2-dimethyl-2H-chromen-6-ylmethyl)-3,4-dimethoxy-benzenesulfonamide (5 g). Yield: 58%. $^1$H NMR (CDCl$_3$): δ 7.39 (d, J=6.4 Hz, 1H), 7.21 (d, J=2.1 Hz, 1H), 7.10-6.82 (m, 3H), 6.67 (d, J=8.2 Hz, 1H), 6.26 (d, J=9.8 Hz, 1H), 5.57 (d, J=9.8 Hz, 1H), 4.22 (s, 3H), 3.88 (d, J=20.2 Hz, 6H), 1.70-1.18 ppm (m, 15H). $^{13}$C NMR (CDCl$_3$): δ 152.2, 152.1, 150.0, 132.7, 131.0, 130.9, 127.9, 152.3, 122.3, 121.2, 121.0, 116.1, 110.5, 109.8, 76.2, 59.5, 56.2, 56.1, 46.8, 29.3, 28.0, 23.5 ppm. HRMS (ESI) m/z calcd for C$_{25}$H$_{31}$NO$_5$S 480.1842 [(M+Na)+]. found: 480.1822. HPLC: ret. time=14.11 min, 98.1%

Cyclopropyl-N-(2,2-dimethyl-2H-chromen-6-ylmethyl)-3,4-dimethoxy-benzenesulfonamide (5h). Yield: 47%. $^1$H NMR (CDCl$_3$): δ 7.46 (dd, J=2.0, 6.4 Hz, 1H), 7.27 (d, J=2.0 Hz, 1H), 7.06 (dd, J=2.0, 6.4 Hz, 1H), 6.97-6.93 (m, 2H), 6.70 (d, J=8.0 Hz, 1H), 6.29 (d, J=9.6 Hz, 1H), 4.27 (s, 2H), 5.62 (d, J=9.6 Hz, 1H), 2.01 (quin, J=4.0 Hz, 1H), 1.44 (s, 6H), 0.72 (q, J=3.2 Hz, 2H), 0.59 ppm (q, J=3.2 Hz, 2H). $^{13}$C NMR (CDCl$_3$): δ 152.5, 148.9, 131.0, 130.5, 129.7, 129.0, 126.9, 122.2, 121.6, 121.1, 116.0, 110.4, 110.2, 76.3, 56.2, 56.2, 54.2, 30.6, 28.0, 27.3 ppm. HRMS (ESI) m/z calcd for C$_{23}$H$_{27}$NO$_5$S 452.1508 [(M+Na)+]. found: 452.1489. HPLC: ret. time=7.48 min, 99.5%.

N-Cyclohexyl-N-(2,2-dimethyl-2H-chromen-6-ylmethyl)-3,4-dimethoxy-benzenesulfonamide (5i). Yield: 79.2%. $^1$H NMR (CDCl$_3$): δ 7.42 (dd, J=2.0 Hz, 6.4 Hz, 1H), 7.30-7.15 (m, 1H), 7.16 (d, J=8.4 Hz, 1H), 7.10-7.08 (m, 1H), 7.02 (d, J=2.0 Hz, 1H), 6.91 (d, J=8.4 Hz, 1H), 6.71 (d, J=8.0 Hz, 1H), 6.31 (d, J=9.6 Hz, 1H), 5.63 (d, J=9.6 Hz, 1H), 4.31 (s, 2H), 3.95 (s, 3H), 3.90 (s, 3H), 1.70-1.54 (m, 4H), 1.43 (s, 6H), 1.27-1.20 ppm (m, 6H). Yield: 79%. HPLC: ret. time=14.4 min, 99.5%.

General Procedure for the Synthesis of 5j-5m.

To a solution of secondary amine 4 (1 equiv) in DCM was added triethylamine (3 equiv.) and then the appropriate sulfonylchloride (2 equiv.). The reaction was stirred at room temperature for 24 h. Then sat. NH$_4$Cl was added to the reaction mixture, which was extracted with DCM (×2). After drying over MgSO$_4$ the DCM solution was concentrated under vacuum. The crude product was purified by flash column chromatography (silica gel).

N-((2,2-Dimethyl-2H-chromen-6-yl)methyl)-4-methoxy-N-phenylbenzenesulfonamide (5j). Yield: 26.4 mg (30%). $^1$H NMR (CDCl$_3$): δ 7.60 (d, J=9.2 Hz, 1H), 7.28-7.22 (m, 3H), 7.00-6.90 (m, 4H), 6.62 (d, J=9.2 Hz, 1H), 6.24 (d, J=10.0 Hz, 1H), 5.58 (d, J=10 Hz, 1H), 4.62 (s, 2H), 3.90 (s, 3H), 1.40 ppm (s, 6H). $^{13}$C NMR (CDCl$_3$): δ 162.9, 139.1, 130.9, 129.8, 129.3, 129.1, 128.8, 128.1, 127.8, 126.6, 122.3, 116.0, 114.0, 76.3, 55.6, 54.3, 28.0 ppm. HRMS (ESI) m/z calcd for C$_{23}$H$_{27}$NO$_5$S: 452.1508 [(M+H)$^+$]. found: 452.1489. HPLC, ret. time=14.03 min, 96.1%

N-((2,2-Dimethyl-2H-chromen-6-yl)methyl)-3,5-dimethyl-N-phenylbenzenesulfonamide (5k). $^1$H NMR: δ 7.54 (s, 2H), 7.30-7.23 (m, 3H), 7.00-6.97 (m, 1H), 6.90-6.88 (m, 2H), 6.60 (d, J=8.8 Hz, 1H), 6.24 (d, J=10 Hz, 1H), 5.58 (d, J=9.6 Hz, 1H), 4.63 (s, 2H), 2.41 (s, 3H), 2.36 (s, 3H), 1.42 (s, 6H). MS (ESI) m/z 458 [(M+Na)$^+$].

2,5-Dichloro-N-((2,2-dimethyl-2H-chromen-6-yl)methyl)-N-phenylbenzenesulfonamide (5l). NMR (CDCl$_3$): δ 7.84 (d, J=2.4 Hz, 1H), 7.48 (d, J=8.4 Hz, 1H), 7.44-7.40 (m, 1H), 7.23-7.21 (m, 3H), 7.06-7.04 (m, 2H), 6.92-6.90 (m, 2H), 6.64 (d, J=7.6 Hz, 1H), 6.27 (d, J=10.0 Hz, 1H), 5.60 (d, J=9.6 Hz, 1H), 4.92 (s, 2H), 1.42 ppm (s, 6H). MS (ESI) m/z 471 [(M+Na)$^+$].

4,4-Bromo-N-((2,2-dimethyl-2H-chromen-6-yl)methyl)-N-phenyl-2-(trifluoromethyl)benzenesulfonamide (5m). Yield: 23%. $^1$H NMR (CDCl$_3$): δ 1.45 (s, 6H), 4.95 (s, 2H), 5.60 (d, 1H, J=9.6), 6.27 (d, 1H, J=10), 6.64 (s, 1H, J=7.6), 6.91 (m, 2H), 7.05 (m, 2H), 7.21 (m, 3H,) 7.43 (m, 1H) 7.48 (m, 1H), 7.84 ppm (d, 1H, 2.4). HPLC: ret. time=19.6 min, 96.7%.

4-(3-Methylpent-1-yn-3-yloxy)benzaldehyde (7). To a solution of 3-methyl-1-pentyn-3-ol 6 (0.319 mL, 2.83 mmol) in acetonitrile (3 mL) at 0° C. was added DBU (0.55 mL, 3.69 mmol). Then TFAA (0.34 mL, 2.46 mmol) was added drop wise and the solution was stirred at 0° C. for 30 min. To a solution of 4-hydroxybenzaldehyde (300 mg, 2.46 mmol) in acetonitrile at 0° C. was added DBU (0.55 mL 3.69 mmol) and CuCl$_2$.2H$_2$O (0.42 mg, 0.0025 mmol). The first mixture was added to the second mixture over a period of five min. The reaction was stirred overnight. The solvent was removed by rotary evaporation and the residue diluted with DCM. Then the organic layer washed with 1M HCl, 1M NaOH, sat NaHCO$_3$ and brine, dried over MgSO$_4$ and concentrated in vacuum to give 170 mg (32%) of product. $^1$H NMR (CDCl$_3$): δ 9.91 (s, 1H), 7.83-7.81 (m, 2H), 7.36-7.34 (m, 2H), 2.69 (s, 1H), 2.06-1.92 (m, 2H), 1.66 (s, 3H), 1.12 ppm (t, J=7.2 Hz, 3H).

2-Ethyl-2-methyl-2H-chromene-6-carbaldehyde (8). A solution of 7 (170 mg) in xylene (3 mL) was subjected to microwave irradiation for 100 min at 220 W, 200 torr, 120° C. The solvent was removed in vacuum to give a quantitative yield of the product (170 mg). $^1$H NMR (CDCl$_3$): δ 9.81 (s, 1H), 7.63 (dd, J=8.0 Hz, 2.0 Hz, 1H), 7.50 (d, J=2.0 Hz, 1H), 6.85 (d, J=8.4 Hz, 1H), 6.42 (d, J=10.0 Hz, 1H), 5.62 (d, J=10.0 Hz, 1H), 1.81-1.66 (m, 3H), 1.43 (s, 3H), 0.97 ppm (t, J=7.6 Hz, 3H).

N-((2-Ethyl-2-methyl-2H-chromen-6-yl)methyl)benzenamine (9). Reaction was carried out following the same procedure as for 2a-2f using 170 mg of 8 to give 90.9 mg (41%) of product. $^1$H NMR (CDCl$_3$): δ 7.22-7.18 (m, 5H), 7.11 (d, J=6.0 Hz, 2.4 Hz, 1H), 6.99 (d, J=2.0 Hz, 2H), 6.77-6.74 (m, 3H), 6.68-6.66 (m, 2H), 6.36 (d, J=10.0 Hz, 1H), 5.58 (d, J=10.0 Hz, 1H), 4.21 (s, 2H), 1.76-1.71 (m, 3H), 1.33 (s, 3H), 0.96 ppm (t, J=7.6 Hz, 3H).

N-((2-Ethyl-2-methyl-2H-chromen-6-yl)methyl)-3,4-dimethoxy-N-phenylbenzenesulfonamide (10). To a solution of 9 (80 mg, 0.29 mmol) in DCM (3 mL) was added Et$_3$N (0.12 mL, 0.85 mmol) and 3,4-dimethoxybenzenesulfonyl chloride (135 mg, 0.573 mmol). After 24 h, sat. NH4Cl was added to the reaction mixture and the aqueous layer was extracted with DCM (5×2 mL). The organic layers was combined, dried over MgSO$_4$ and concentrated under vacuum. The crude product was purified by column (silica gel, 5:1 Hx/EtOAc) to give a white solid (42.6 mg). Yield: 32%. $^1$H NMR (CDCl$_3$): δ 7.35 (dd, J=6.4 Hz, 2.0 Hz, 1H), 7.25-7.23 (m, 3H), 7.02-6.98 (m, 3H), 6.94 (d, J=8.4 Hz, 1H), 6.91-6.88 (m, 2H), 4.62 (s, 2H), 3.98 (s, 3H), 3.77 (s, 3H), 1.71-1.65 (m, 2H), 1.43 (s, 3H), 0.94 ppm (t, J=7.6 Hz, 3H). $^{13}$C NMR (CDCl$_3$): δ 152.8, 152.5, 148.7, 139.2, 130.5, 129.8, 129.3, 129.2, 128.8, 127.9, 127.8, 126.6, 122.8, 121.4, 121.1, 115.8, 110.4, 79.0, 56.2, 56.1, 54.3, 34.0, 26.0 ppm. MS (ESI) m/z 502 [(M+Na)$^+$]. HPLC: ret. time=5.9 min, 98.9%.

N-Phenylquinolin-3-amine (12). To a solution of quinoline-3-carbaldehyde 11 (79 mg, 0.5 mmol) in MeOH (5 mL) was added aniline (0.05 mL, 0.55 mmol) and ZnCl$_2$ (136 mg, 2.0 mmol) and the reaction was stirred at room temperature for 15 min. Then NaCNBH$_3$ (62.8 mg, 2.0 mmol) was added and to the reaction was stirred overnight at room temperature. The solvent was removed by rotary evaporation and the residue suspended in EtOAc. The organic layers were combined and washed with NaHCO$_3$, water, and brine and then dried over MgSO. Concentration in vacuo gave the crude product, which was used in the next step without further purification. $^1$H NMR (CDCl$_3$): 9.05 (s, 1H), 8.23 (d, J=7.6 Hz, 2H), 7.77 (d, J=8.0 Hz, 1H), 7.71-7.66 (m, 1H), 7.54-7.51 (m, 1H), 7.21-7.16 (m, 2H), 6.76-6.72 (m, 1H), 6.68-6.60 (m, 2H), 4.54 (s, 2H), 4.16 (s, br, 1H).

3,4-Dimethoxy-N-phenyl-N-(quinolin-3-ylmethyl)benzenesulfonamide (13). To a solution of 12 (75 mg, 0.320 mmol) in DCM was added 3,4 dimethoxybenzylsulfonyl chloride (83 mg, 0.35 mmol) and triethylamine (0.09 mL, 0.640 mmol). The reaction was stirred overnight at room temperature and the reaction mixture was washed with water and brine. The organic layer was dried over MgSO$_4$, concentrated in vacuo, and purified by column chromatography (silica gel, 2:1 Hexane/EtOAc) to give a white powder. Yield: 45%. $^1$H NMR (CDCl$_3$): 8.86 (s, 1H), 8.14 (d, J=8.0 Hz, 2H), 7.84 (dd, J=7.2 Hz, 1.2 Hz, 1H), 7.80-7.76 (m, 1H), 7.64-7.60 (m, 1H), 7.49 (dd, J=6.0 Hz, 2.4 Hz, 1H), 7.38-7.30 (m, 3H), 7.17-7.14 (m, 2H), 7.08-7.05 (m, 2H), 5.03 (s, 2H), 4.08 (s, 3H), 3.85 ppm (s, 3H). $^{13}$C NMR (CDCl$_3$): 152.8, 150.8, 148.8, 147.6, 138.0 135.7, 129.6, 129.2, 129.1, 129.0, 128.2, 127.7, 127.7, 126.9, 121.6, 110.5, 110.4, 56.2, 56.1, 52.4 ppm. MS (ESI) m/z 435 [(M+H)$^+$]. HPLC: ret. time=14.6 min, 95.2%.

N-((2,2-Dimethyl-2H-chromen-6-yl)methyl)benzenamine (15a). To a solution of 2,3-dihydro-2,2-dimethylbenzofuran-5-carboxaldehyde 14 (250 mg, 1.42 mmol) in MeOH (10 mL) was added aniline (0.14 mL, 1.022 mmol), NaCNBH$_3$ (178 mg, 2.84 mmol) and ZnCl$_2$ (dried in oven) (387 mg, 2.84 mmol). The reaction was stirred at room temperature overnight, and then the solvent was removed by rotary evaporation. 0.1M NaOH was added to the resulting residue, which was extracted with EtOAc (×2). The combined organic layers were dried over MgSO$_4$ and concentrated in vacuum to give 301 mg of the product (84%). $^1$H NMR (CDCl$_3$): d 7.29-7.22 (m, 3H), 7.17 (d, J=8.0 Hz, 1H), 6.95-6.70 (m, 4H), 4.28 (s, 2H), 3.06 (s, 2H), 1.55 ppm (s, 6H).

N-((2,2-Dimethyl-2,3-dihydrobenzofuran-5-yl)methyl)-3,4-dimethoxy-N-phenylbenzenesulfonamide (16a). To a solution of 15a (100 mg, 0.395 mmol) in DCM (5 mL) was added triethylamine (0.17 mL, 0.790 mmol) and 3,4-dimethoxybenzenesulfonylchloride (187 mg, 0.790 mmol) dissolved in 1 mL of DCM and the reaction was stirred for 72 h. Ammonium chloride was added to the reaction mixture, which was then extracted with DCM (×2). After drying the combined organic layers over MgSO$_4$ and concentration in vacuum, the crude reaction mixture was purified by column (silica gel, 3:1 Hx/EtOAc) to give a white solid (76 mg, 42%). $^1$H NMR (CDCl$_3$): δ 7.33 (dd, J=2.13, 8.44, 1H), 7.26-7.21 (m, 3H), 7.09 (s, 1H) 7.00-6.96 (m, 3H), 6.92 (d, J=8.5, 1H), 6.83 (d, J=8.1, 1H), 6.52 (d, J=8.1, 1H), 4.62 (s, 2H), 3.95 (s, 1H), 3.75 (s, 1H), 2.92 (s, 2H), 1.42 ppm (s, 1H). $^{13}$C NMR (CDCl$_3$): δ 158.4, 152.5, 148.7, 139.3, 129.2, 127.5, 125.6, 121.4, 110.4, 108.9, 86.9, 56.2, 56.1, 54.6, 42.7, 28.2 ppm. MS (ESI) m/z 435 [(M+H)]. HPLC: ret. time=10.5 min, 96.1%.

General Procedure for the Synthesis of Compound 16b-16f.

To a solution of 14 in methanol was added amine (1.1 equiv.), zinc chloride (2 equiv.) and the reaction mixture was stirred for 2 h before NaCNBH$_3$ (2 equiv.) was added. The reaction was then stirred at room temperature overnight. The solvent was removed by rotary evaporation and the residue diluted with EtOAc and washed with Na$_2$CO$_3$ (sat) and brine. The organic layers were dried over MgSO$_4$ and concentrated in vacuo. The product was used without further purification in the next step. To the resulting secondary amine 15 (1 equiv.) in DCM was added Et$_3$N (2 equiv.) and the appropriate aryl or alkyl sulfonyl chloride (1.1 equiv.) and the reaction stirred at room temperature overnight. The reaction mixture was diluted with DCM and washed with water and brine. The organic layer was dried over Na$_2$SO$_4$ and concentrated in vacuo. The crude product was purified by flash chromatography (silica gel).

N-Cycloheptyl-N-((2,2-dimethyl-2,3-dihydrobenzofuran-5-yl)methyl)-3,4dimethoxybenzenesulfonamide (16b). Yield: 14%. $^1$H NMR (CDCl$_3$): δ 7.43 (dd, J=2.14, 8.44, 1H), 7.25-7.24 (m, 2H), 7.05 (d, J=8.13, 1H), 6.92 (d, J=8.5, 1H), 6.65 (d, J=8.1, 1H), 4.28 (s, 2H), 3.96 (s, 3H), 3.90 (s, 3H), 3.00 (s, 2H), 1.63-1.51 (m, 8H), 1.48 (s, 6H), 1.45-1.27 ppm (m, 7H). HRMS (ESI) calcd for C$_{26}$H$_{35}$NO$_5$S m/z [(M+Na)$^+$] 496.2134. found: 496.2122. HPLC: ret. time=18.6 min, 99.4%.

N-((2,2-dimethyl-2,3-dihydrobenzofuran-5-yl)methyl)-N-isopropyl-3,4-dimethoxybenzenesulfonamide(16c). Yield: 18%. $^1$H NMR (CDCl$_3$): δ 7.45 (d, J=8.2 Hz, 1H), 7.27 (s, 1H), 7.10 (d, J=15.6 Hz, 1H), 6.94 (t, J=7.5 Hz, 2H), 6.63 (d, J=7.6 Hz, 1H), 4.24 (s, 2H), 3.94 (d, J=19.3 Hz, 6H), 3.05-2.93 (m, 2H), 2.91 (d, J=6.9 Hz, 2H), 1.82-1.66 (m, 1H), 1.48 (s, 6H), 0.77 ppm (d, J=5.7 Hz, 6H). $^{13}$C NMR (CDCl$_3$): δ 158.5, 152.3, 149.0, 132.1, 128.4, 127.9, 127.7, 125.6, 121.1, 110.5, 109.9, 109.0, 87.1, 77.4, 77.1, 76.7, 56.2, 56.1, 55.8, 52.4, 42.7, 28.1, 26.9, 20.0 ppm. HRMS (ESI) m/z calcd for C$_{23}$H$_{31}$NO$_5$S [(M+Na)$^+$] 456.1821. found: 456.1833. HPLC: ret. time=11.5 min, 97.6%.

N-Butyl-N-((2,2-dimethyl-2,3-dihydrobenzofuran-5-yl)methyl)-3,4-dimethoxybenzenesulfonamide(16d). Yield: 21%. $^1$H NMR (CDCl$_3$): δ 7.47 (dd, J=8.4, 1.5 Hz, 1H), 7.34-7.22 (m, 2H), 7.13 (s, 1H), 6.96 (d, J=8.4 Hz, 2H), 6.65 (d, J=8.1 Hz, 1H), 4.25 (s, 2H), 3.95 (d, J=16.7 Hz, 6H), 3.22-3.03 (m, 2H), 2.99 (s, 2H), 1.57 (d, J=21.8 Hz, 1H), 1.49 (s, 6H), 1.41-1.24 (m, 3H), 1.23-1.08 (m, 2H), 0.79 ppm (t, J=7.3 Hz, 3H). $^{13}$C NMR (CDCl$_3$): δ 158.6, 152.2, 149.2, 143.0, 132.3, 128.3, 127.4, 125.5, 120.9, 110.5, 109.8, 109.0, 87.1, 77.4, 77.0, 76.7, 56.2, 56.1, 51.3, 47.3, 42.7, 29.9, 28.1, 19.9, 13.7 ppm. HRMS (ESI) m/z calcd for C$_{23}$H$_{31}$NO$_5$S [(M+Na)$^+$] 456.1821. found: 456.1812. HPLC: ret. time=11.2 min, 98.0%

N-Cyclohexyl-N-((2,2-dimethyl-2,3-dihydrobenzofuran-5-yl)methyl)-3,4-dimethoxybenzenesulfonamide (16e). Yield: 36%. $^1$H NMR (CDCl$_3$) δ 7.41 (d, J=8.4, 1H), 7.22 (s, 2H), 7.03 (d, J=7.9, 1H), 6.90 (d, J=8.3, 1H), 6.63 (d, J=7.9, 1H), 4.31 (s, 2H), 3.70 (1H) 3.94 (s, 3H) 3.88 (s, 3H), 2.98 (s, 1H), 1.69-1.52 (m, 7H), 1.47 (s, 6H), 1.27-1.22 ppm (m, 4H). HRMS (ESI) m/z calcd for C$_{25}$H$_{33}$NO$_5$S [(M Na)] 482.1977. found: 482.1981. HPLC: ret. time=16.4 min, 95.6%.

N-Cyclopentyl-N-((2,2-dimethyl-2,3-dihydrobenzofuran-5-yl)methyl)-3,4-dimethoxybenzenesulfonamide (16f). Yield: 31%. $^1$H NMR (CDCl$_3$): δ 7.44 (d, J=8.5, 1H), 7.27 (s, 2H), 7.04 (d, J=8.10, 1H), 6.92 (d, J=8.4, 1H), 6.65 (d, J=8.1, 1H), 4.29 (s, 3H), 3.95 (s, 3H), 3.90 (s, 3H), 2.99 (s, 2H), 1.85-1.58 (m, 3H), 1.60-1.22 ppm (m, 12H). HRMS (ESI) m/z calcd for C$_{24}$H$_{31}$NO$_5$S [(M+Na)$^+$] 468.1821. found: 468.1817. HPLC: ret. time=14.4 min, 95.0%

2,2-Dimethyl-2H-pyrano[2,3-b]pyridine-6-carbaldehyde (18). To a solution of 17 (100 mg, 0.390 mmol) in dry ether (2 mL) was added BuLi (0.25 mL, 2.5 M solution in THF) drop wise at −65° C. and the reaction stirred for 15 min. Then DMF (anhydrous) was added drop wise and the reaction was stirred at −65° C. for 1.5 h. Water was added to quench the reaction, which was extracted with EtOAc (×2). The organic layers were washed with water (×1), brine (×1), dried over MgSO$_4$ and concentrated in vacuo to give a yellow oil. Purification by column chromatography (silica gel) 6:1 Hx/EtOAc gave a white solid 23 mg (31%). $^1$H NMR (CDCl$_3$): δ 1.58 (s, 1H); 5.79 (d, 1H, J=8.0 Hz), 6.36 (d, 1H, J=9.6 Hz), 7.76 (s, 1H), 8.50 (s, 1H), 9.92 ppm (s, 1H).

N-((2,2-Dimethyl-2H-pyrano[2,3-b]pyridin-6-yl)methyl)benzenamine (19a). To a solution of 2,2-dimethyl-2H-pyrano[2,3-b]pyridine-6-carbaldehyde 18 (20 mg, 0.106 mg) in methanol (1 ml) was added aniline (0.01 mL, 0.12 mmol), NaCNBH$_3$ (13 mg, 0.212 mmol) and ZnCl$_2$ (29 mg, 0.212 mmol). The reaction was stirred for 30 minutes after which the solvent was removed by rotary evaporation and the 1M NaOH added to the residue, extracted with DCM, dried over MgSO4 and concentrated in vacuo. Purified by column chromatography (3:1 Hx/EtOAc) to give a white solid 20 mg (72%). $^1$H NMR (CDCl$_3$) δ 8.01 (s, 1H), 7.29 (s, 1H), 7.26-7.16 (m, 2H), 6.74 (t, J=7.2 Hz, 1H), 6.63 (d, J=8.0 Hz, 1H), 6.26 (d, J=9.6 Hz, 1H), 5.67 (d, J=9.6 Hz, 1H), 4.21 (s, 2H), 1.51 ppm (s, 6H). $^{13}$C NMR (CDCl$_3$) δ 159.6, 147.8, 146.4, 133.8, 132.2, 129.3, 128.4, 120.9, 118.0, 115.4, 113.0, 79.2, 45.4, 28.8 ppm. HRMS (ESI) m/z calcd for C$_{11}$H$_{11}$NO$_2$ [(M+H)$^+$] 190.0868. found: 190.0870.

N-((2,2-dimethyl-2H-pyrano[2,3-b]pyridin-6-yl)methyl)cyclohexanamine (19b). To a solution of 2,2-dimethyl-2H-pyrano[2,3-b]pyridine-6-carbaldehyde 18 (23 mg, 0.121 mmol) in MeOH (1 mL) was added cyclohexylamine (0.014 mL, 0.121 mmol), NaCNBH$_3$ (15 mg, 0.242 mmol) and Zinc chloride (33 mg, 0.242 mmol) and stirred overnight. The solvent was removed by rotary evaporation and the residue dissolved in EtOAc and washed with 1M NaOH, water and brine, dried over MgSO$_4$ and concentrated in vacuo. The product was used in the next step without further purification.

N-((2,2-Dimethyl-2H-pyrano[2,3-b]pyridin-6-yl)methyl)-3,4-dimethoxy-N-phenylbenzenesulfonamide (20a). To a solution of 19a (20 mg, 0.075 mmol) in DCM (1 mL) was added 3,4-dimethoxybenzenesulfonyl chloride (36 mg, 0.150 mmol) and triethylamine (0.021 mL, 0.150 mmol). The reaction was stirred for 24 hours at room temperature. The reaction mixture was washed with water (×2) and the organic layer dried over MgSO$_4$ and concentrated in vacuo. Column chromatography (2:1 hexane/EtOAc) gave a white solid (?? g). Yield: 43%. $^1$H NMR (CDCl$_3$): δ 1.47 (s, 6H), 3.76 (s, 3H), 3.97 (s, 3H), 4.60 (s, 2H), 5.66 (d, 1H, J=9.6), 6.26 (d, 1H, J=10), 6.93-6.99 (m, 4H), 7.23-7.25 (m, 3H), 7.32-7.36 (m, 2H), 7.63 ppm (d, 1H, J=2.4). HRMS (ESI) m/z calcd for C$_{25}$H$_{25}$N$_2$O$_5$S [M+H)$^+$] 467.1641. found: 467.1636. HPLC: ret. time=7.5 min, 99.0%

N-Cyclohexyl-N-((2,2-dimethyl-2H-pyrano[2,3-b]pyridin-6-yl)methyl)-3,4-dimethoxybenzenesulfonamide (20b). Yield: 60%. $^1$H NMR (CDCl$_3$): δ 7.89 (s, 1H), 7.49 (s, 1H), 7.44 (d, J=2.0 Hz, 1H), 7.28 (s, 1H), 6.93 (d, J=8.8 Hz, 1H), 6.31 (d, J=10 Hz, 1H), 5.69 (d, J=10 Hz, 1H), 4.30 (s, 2H), 3.95 (s, 3H), 3.91 (s, 3H), 1.71-1.52 (m, 10H), 1.29-1.21 ppm (m, 6H). HRMS (ESI) m/z calcd for C$_{25}$H$_{32}$N$_2$O$_5$S [(M+H)$^+$] 473.2110. found: 473.2127. HPLC: ret. time=11.4 min, 95.0%.

6-bromo-2,2-dimethyl-2H-pyrano[3,2-b]pyridine (23). To a solution 2-methyl-3-butyn-2-ol (21) in acetonitrile (6 mL) was added DBU (0.80 mL, 6.61 mmol) at 0° C., then TFAA was added dropwise, also at 0° C. The reaction was stirred for 30 min. In another round bottom flask, DBU (0.80 mL, 6.61 mmol) was added to a solution of 2-bromo-5-hydroxy pyridine (1 g, 5.75 mmol) in 6 mL of acetonitrile at 0° C. Then 2-methyl-3-butyn-2-ol was added dropwise into this reaction, which was stirred for 30 additional min. The solvent was removed by rotary evaporation, and the residue was diluted with DCM. After separation, the organic layer was washed with 1M HCl, 1M NaOH, sat NaHCO$_3$ and brine, was dried over MgSO$_4$ and concentrated in vacuum. The crude product was dissolved in 2 ml of xylene and subjected to microwave irradiation (130° C., 220 W) for 30 min. The solvent was removed by rotary evaporation and the product concentrated in vacuum. The crude product was purified by column chromatography (silica gel) (10:1 Hx/EtOAc) to give 300 mg of a yellow solid (23% over the two steps). $^1$H NMR (CDCl$_3$): 1.45 (s, 6H), 5.86 (d, 1H, J=10.4), 6.44 (d, 1H, J=10), 6.90 (d, 1H, J=8.8), 7.14 ppm (s, 1H, J=8.4). HRMS (ESI) m/z calcd for C$_{10}$H$_{11}$NOBr [(M+H)$^+$] 240.0024. found: 240.0026.

2,2-Dimethyl-2H-pyrano[3,2-b]pyridine-6-carbaldehyde (24). To a solution of 23 (200 mg, 0.83 mmol) in anhydrous THF (5 mL) at −78° C. was added BuLi (2.5M, 0.35 mL) and stirred for 35 minutes, then DMF (0.08 mL, 0.1 mmol) was added dropwise. The reaction was stirred at −78° C. for 30 additional minutes. Water (3 mL) was added to quench the reaction and was extracted with EtOAc. The organic layer was washed with water, brine, dried over MgSO$_4$ and concentrated under reduced pressure. The crude product was purified by flash column chromatography; 20:1 Hx/EtOAc. To give the product as a yellowish solid (23% yield). $^1$H NMR δ 1.53 (s, 6H), 6.01 (d 1H, J=10.4), 6.58 (d, 1H, J=10.4), 7.13 (d, 1H, J=8.4), 7.77 (d, 1H, J=8.4), 9.93 ppm (s, 1H). $^{13}$C NMR δ 28.8, 78.7, 123.0, 123.3, 123.4, 136.3, 145.8, 153.7, 191.9 ppm N-((2,2-Dimethyl-2H-pyrano[3,2-b]pyridin-6-yl)methyl)aniline (25a). To a solution of 2,2-dimethyl-2H-pyrano[3,2-b]pyridine-6-carbaldehyde (434 mg, 2.28 mmol) in methanol (3 mL) was added aniline (0.3 mL, 2.52 mmol) and zinc chloride (621 mg, 4.56 mmol) and stirred at room temperature for 2 hours. Then NaCNBH$_3$ (287 mg, 4.56 mmol) was added and stirred overnight. Purification by column: 4:1 Hx/EtOAc to give an off-white solid. Yield: 48%. $^1$H NMR (CDCl$_3$) δ 1.49 (s, 6H), 4.361 (s, 2H), 5.91 (d, 1H, J=10), 6.55 (d, 1H, J=10), 6.68-6.71 (m, 3H), 7.01 (d, 1H, J=8.4), 7.08 (d, 1H, J=8.4), 7.18-7.38 ppm (m, 2H).

N-((2,2-dimethyl-2H-pyrano[3,2-b]pyridin-6-yl)methyl)-3,4-dimethoxy-N-phenylbenzenesulfonamide (26a). To a solution of the 25a (60 mg, 0.237 mmol) in dichloromethane (2.5 mL) was added triethylamine (0.07 mL, 0.474 mmol) and the 3,4-dimethoxybenzenesulfonyl chloride (84 mg, 0.355 mmol), the reaction was stirred for 24 hours. The reaction mixture diluted with DCM and the organic layer washed with then water and brine, dried over magnesium sulfate and concentrated in vacuo. The crude product was purified by column chromatography (silica gel, 3:1 hexane/EtOAc to 1:1 hexane/EtOAc) to give an off-white solid (56 mg). Yield: 50%. $^1$H NMR (CDCl$_3$): δ 7.29 (dd, J=8.4, 2.1 Hz, 2H), 7.25-7.17 (m, 3H), 7.14-7.09 (m, 2H), 6.96 (d, J=8.4 Hz, 1H), 6.92-6.86 (m, 2H), 6.32 (d, J=10.1 Hz, 1H), 5.80 (d, J=10.1 Hz, 1H), 4.78 (s, 2H), 3.94 (s, 3H), 3.72 (s, 3H), 1.40 ppm (s, 6H). HRMS (ESI) m/z calcd for C$_{25}$H$_{26}$N$_2$O$_5$S [(M+H)$^+$] 467.1641. found 467.1641. HPLC: ret. time=9.7 min, 98.1%

General Procedure for the Synthesis of 26b-26j by Reaction with Alkylsulfonyl Chloride To a solution of 25 (1 eq) in methanol was added the primary amine (1 equiv.), ZnCl$_2$ (2 equiv.) and the reaction was stirred at room temperature for 2 h. Then NaCNBH$_3$ (2 equiv.) was added and the reaction was stirred at room temperature overnight. The solvent was removed by rotary evaporation and EtOAc was added to the residue. The solid was filtered through Celite and the filtrate washed with 1M NaOH, water and brine. The organic layer was dried over MgSO$_4$ and concentrated under reduced pressure. The crude secondary amine product was used without further purification.

To a solution of the secondary amine (1 equiv.) in DCM was added triethylamine (3 equiv.) and the sulfonylchloride (1.5 equiv.). The reaction was stirred for 24 to 48 h. Then water was added and the organic layer extracted with DCM, dried over MgSO$_4$, concentrated under reduced pressure, and purified by flash column chromatography.

N-Butyl-N-((2,2-dimethyl-2H-pyrano[3,2-b]pyridin-6-yl)methyl)-3,4-dimethoxybenzenesulfonamide (26b). Yield: 42%. $^1$H NMR (CDCl$_3$): δ 7.47 (d, J=2.4 Hz, 1H), 7.29-7.26 (m, 2H), 7.04 (d, J=8.4 Hz, 1H), 6.94 (d, J=8.8 Hz, 1H), 6.40 (d, J=8.0 Hz, 1H), 5.88 (d, J=10 Hz, 1H), 4.37 (s, 1H), 3.96 (s, 3H), 3.93 (s, 3H), 3.18 (t, J=7.6 Hz, 2H), 1.48 (s, 1H), 1.38 (m, 2H), 1.18 (sx, J=7.2, 2H), 0.79 ppm (t, J=7.2, 3H). $^{13}$C NMR (CDCl$_3$): δ 152.4, 149.0, 148.8, 148.7, 135.4, 131.6, 123.7, 123.7, 122.7, 121.0, 110.5, 109.8, 56.2, 56.2, 53.3, 48.8, 30.2, 28.2, 19.9, 13.6 ppm. HRMS (ESI) m/z calcd for C$_{23}$H$_{31}$N$_2$O$_5$S [(M+H)$^+$] 447.1954, observed: 447.1937. HPLC, ret. time=11.4 min, 95.4%

N-(3,4-Dimethoxyphenyl)-N-((2,2-dimethyl-2H-pyrano[3,2-b]pyridin-6-yl)methyl)-3,4-dimethoxybenzenesulfonamide (26c). Yield: 51%. $^1$H NMR δ (CDCl$_3$): δ 7.32-7.38 (m, 2H), 7.01-6.98 (m, 2H), 6.91 (d, J=8.4 Hz, 1H), 6.66 (d, J=8.4 Hz. 1H), 6.68-6.62 (m, 2H), 6.34 (dd, J=12.0, 0.4 Hz), 5.82 (d, J=10.0 Hz, 1H), 4.76 (s, 2H), 3.96 (s, 3H), 3.83 (s, 3H), 3.79 (s, 3H), 3.72 (s, 3H), 1.43 ppm (s, 6H). $^{13}$C NMR (CDCl$_3$): δ 152.6, 148.7, 148.7, 148.6, 148.5, 147.8, 140.2, 135.3, 132.2, 129.6, 123.6, 123.6, 122.6, 121.8, 121.0, 112.5, 110.5, 110.3, 56.2, 56.2, 56.1, 55.9, 28.2 ppm. HRMS (ESI) m/z calcd for C$_{27}$H$_{31}$N$_2$O$_7$S [(M+H)$^+$] 527.1852. found: 527.1866, ret. time=7.6 min, 98.4%

N-Cyclopentyl-N-((2,2-dimethyl-2H-pyrano[3,2-b]pyridin-6-yl)methyl)-3,4-dimethoxybenzenesulfonamide (26d). Yield: 31%. $^1$H NMR (CDCl$_3$): δ 7.55-7.35 (m, 2H), 7.35-7.22 (m, 1H), 7.07 (d, J=8.4 Hz, 1H), 6.98-6.86 (m, 1H), 6.46 (dd, J=14.7, 10.2 Hz, 1H), 5.89 (d, J=10.1 Hz, 1H), 4.44-4.24 (m, 3H), 3.96 (s, 3H), 3.93 (s, 3H), 1.76-1.15 ppm (m, 15H). $^{13}$C NMR (CDCl$_3$): δ 152.4, 150.7, 148.5, 135.4, 132.2, 123.8, 123.7, 121.9, 121.2, 110.5, 109.8, 59.4, 56.3, 56.2, 48.6, 29.1, 28.2, 23.4 ppm. HRMS (ESI) m/z calcd for C$_{24}$H$_{31}$N$_2$O$_5$ [(M+H)$^+$] 459.1954. found: 459.1938. HPLC: ret. time=11.3 min, 96.9%.

N-Cyclohexyl-N-((2,2-dimethyl-2H-pyrano[3,2-b]pyridin-6-yl)methyl)-3,4-dimethoxybenzenesulfonamide (26e). Yield: 46%. $^1$H NMR (CDCl$_3$): 7.47 (dd, J=2.4, 6.4 Hz, 1H), 7.42 (d, J=8.4 Hz, 1H), 7.30 (d, J=2.4 Hz, 1H), 7.06 (d, J=8.4, 1H), 6.93 (d, J=8.8 Hz, 1H), 6.45 (d, J=10 Hz, 1H), 5.88 (d, J=10 Hz, 1H), 3.96 (s, 3H), 3.92 (s, 3H), 3.80 (m, 1H), 1.64 (m, 3H), 1.48 (m, 9H), 1.25-1.20 ppm (m, 4H). $^{13}$C NMR (CDCl$_3$): δ 152.2, 150.7, 149.1, 148.5, 140.0, 135.2, 133.2, 123.7, 123.7, 122.5, 120.7, 110.6, 109.5, 58.4, 56.2, 56.1, 48.5, 31.3, 28.2, 26.1, 25.2 ppm. HRMS (ESI) m/z calcd for C$_{25}$H$_{33}$N$_2$O$_5$S [(M+H)$^+$] 473.2110. found: 473.2118. HPLC: ret. time=13.1 min, 96.8%

N-((2,2-Dimethyl-2H-pyrano[3,2-b]pyridin-6-yl)methyl)-3,4-dimethoxy-N-(5,6,7,8-tetrahydronaphthalen-2-yl)-benzenesulfonamide (26f). $^1$H NMR (CDCl$_3$): δ 7.39-7.31 (m, 2H), 6.99 (dd, J=13.4, 5.2 Hz, 2H), 6.92 (dd, J=8.1, 2.8 Hz, 2H), 6.81 (d, J=7.6 Hz, 2H), 6.35 (d, J=10.1 Hz, 1H), 5.94-5.71 (m, 1H), 4.78 (d, J=25.5 Hz, 2H), 3.97 (s, 3H), 3.79 (d, J=5.3 Hz, 3H), 2.65 (dd, J=25.6, 13.3 Hz, 4H), 1.83-1.66 (m, 4H), 1.41 ppm (d, J=16.1 Hz, 6H). MS (ESI) [(M+H)$^+$] 521. HPLC: ret. time=15.6 min, 96.9%

N-Cycloheptyl-N-((2,2-dimethyl-2H-pyrano[3,2-b]pyridin-6-yl)methyl)-3,4-dimethoxybenzenesulfonamide (26g). Yield: 18%. $^1$H NMR (CDCl$_3$): δ 7.47 (dt, J=4.4, 2.2 Hz, 1H), 7.44 (d, J=8.4 Hz, 1H), 7.31-7.27 (m, 1H), 7.07 (d, J=8.4 Hz, 1H), 6.94 (dd, J=8.5, 4.9 Hz, 1H), 6.45 (dd, J=10.1, 0.5 Hz, 1H), 5.88 (d, J=10.1 Hz, 1H), 4.44-4.29 (m, 2H), 3.96 (s, 3H), 3.94 (s, 3H), 3.93 (s, 3H), 1.62-1.29 ppm (m, 18H).

N-Cyclooctyl-N-((2,2-dimethyl-2H-pyrano[3,2-b]pyridin-6-yl)methyl)-3,4-dimethoxybenzenesulfonamide (26h). Yield: 45%. $^1$H NMR (CDCl$_3$): δ 7.49 (d, J=6.4, 1H), 7.46 (d, J=10, 1H), 7.32-7.29 (m, 1H), 7.07 (d, J=8.0, 1H), 6.94 (d, J=8.4, 1H), 6.45 (d, J=10, 1H), 5.89 (d, J=10, 1H), 4.38 (s, 2H), 3.97-3.93 (m, 7H), 1.61-1.42 ppm (m, 20H). MS (ESI) m/z [(M+H)$^+$] 501. HPLC, ret. time=16.5 min, 99.0%

N-Cyclobutyl-N-((2,2-dimethyl-2H-pyrano[3,2-b]pyridin-6-yl)methyl)-3,4-dimethoxybenzenesulfonamide (26i). Yield: 40%. $^1$H NMR (CDCl$_3$): δ 7.44 (dd, J=8.4, 2.2 Hz, 1H), 7.36 (d, J=8.4 Hz, 1H), 7.31-7.21 (m, 2H), 7.07 (d, J=8.4 Hz, 1H), 6.94 (t, J=6.9 Hz, 1H), 6.40 (dd, J=32.8, 10.0 Hz, 1H), 5.88 (t, J=10.6 Hz, 1H), 4.49-4.28 (m, 3H), 3.96 (s, 3H), 3.93 (d, J=3.0 Hz, 3H), 2.08-1.83 (m, 4H), 1.60-1.40 ppm (m, 8H). $^{13}$C NMR (CDCl$_3$): δ 152.5, 150.3, 149.0, 148.6, 140.1, 135.4, 131.7, 123.8, 123.7, 121.8, 121.0, 110.5, 109.6, 77.4, 77.0, 76.7, 56.2, 56.2, 52.7, 49.3, 28.9, 28.2, 15.0 ppm. MS (ESI+) m/z [(M+H)$^+$] 445. HPLC: ret. time=8.7 min, 97%

N-((2,2-dimethyl-2H-pyrano[3,2-b]pyridin-6-yl)methyl)-N-(4-fluorophenyl)-3,4-dimethoxybenzenesulfonamide (26j). Yield: 12%. $^1$H NMR (CDCl$_3$): δ 7.55-7.40 (m, 1H), 7.38-7.23 (m, 3H), 7.16-7.01 (m, 4H), 7.00-6.87 (m, 5H), 6.40 (t, J=11.7 Hz, 1H), 5.88 (t, J=13.4 Hz, 1H), 4.83 (d, J=14.0 Hz, 2H), 3.97 (s, 3H), 3.86-3.73 (m, 3H), 1.44 ppm (s, 6H). HRMS (ESI) m/z calcd for C$_{25}$H$_{25}$FN$_2$O$_5$S [(M+H)$^+$] 485.1546. found: 485.1531. HPLC: ret. time=10.2 min, 97.6%.

General Procedure for 26k-26t.

To a solution of 25a (1 equiv.) in pyridine at 0° C. was added the appropriate sulfonyl chloride dropwise. The reaction was allowed to warm up to room temperature overnight. The reaction mixture was then diluted with EtOAc and the organic layer was washed with 10% citric acid, sat. NaHCO$_3$, water and brine. The organic layer was dried over MgSO$_4$ and concentrated in vacuo. The crude product was purified by flash column chromatography (silica gel).

N-((2,2-Dimethyl-2H-pyrano[3,2-b]pyridin-6-yl)methyl)-N-phenylcyclohexanesulfonamide (26k). Yield: 60%. $^1$H NMR (CDCl$_3$): δ 7.30-7.22 (m, 4H), 7.07-7.01 (m, 2H), 6.90 (dd, J=24.2, 1.8 Hz, 1H), 6.46 (dd, J=29.3, 2.1 Hz, 1H), 5.86 (d, J=29.3 Hz, 1H), 5.05 (d, J=48.2 Hz, 1H), 4.90 (d, J=48.2 Hz, 1H), 2.13-1.96 (m, 4H), 1.78-1.70 (m, 5H), 1.44 (d, J=6.3 Hz, 6H), 1.27 ppm (m, 2H). $^{13}$C NMR (CDCl$_3$): δ 148.5, 148.3, 143.6, 140.4, 135.2, 129.1, 123.9, 123.8, 123.6, 122.0, 121.8, 92.4, 34.5, 31.8, 28.3, 28.2, 24.7, 21.7, 21.3 ppm. MS (ESI+) m/z [(M+Na)$^+$] 435. HPLC: ret. time=10.16 min, 97.6%

N-((2,2-Dimethyl-2H-pyrano[3,2-b]pyridin-6-yl)methyl)-N-phenylpropane-2-sulfonamide (26l). Yield: 58%. $^1$H NMR (CDCl$_3$): δ 7.37-7.19 (m, 4H), 7.16-6.99 (m, 2H), 6.93 (t, J=9.4 Hz, 1H), 6.46 (dd, J=10.1, 0.5 Hz, 1H), 5.87 (d, J=10.1 Hz, 1H), 4.92 (dd, J=36.5, 16.5 Hz, 2H), 1.81 (s, 3H), 1.75 (d, J=11.8 Hz, 4H), 1.45 ppm (t, J=5.8 Hz, 6H). $^{13}$C NMR (CDCl$_3$): δ 148.5, 148.2, 143.1, 140.5, 135.3, 129.1, 124.2, 123.7, 123.6, 122.2, 122.1, 86.0, 28.3, 28.2, 27.4, 25.4 ppm. MS (ESI+) m/z [(M+H)$^+$] 373. HPLC: ret. time=10.0 min, 97.8%.

N-((2,2-Dimethyl-2H-pyrano[3,2-b]pyridin-6-yl)methyl)-N-phenylcyclopropanesulfonamide (26m). Yield: 46%. $^1$H NMR (CDCl$_3$): δ 7.44-7.42 (m, 2H), 7.34-7.23 (m, 4H), 6.99 (d, J=8 Hz, 1H), 6.40 (d, J=10 Hz, 1H), 5.85 (dd, J=10, 1H), 4.98 (s, 2H), 2.55 (m, 1H), 1.44 (d, J=16.1 Hz, 6H), 1.13-1.11 (m, 2H), 0.98-0.95 ppm (m, 2H). $^{13}$C NMR (CDCl$_3$): δ 148.7, 148.1, 140.4, 139.7, 135.3, 129.1, 128.8, 127.7, 123.7, 123.6, 122.4, 56.2, 28.6, 28.2, 5.16 ppm. HPLC, ret. time=8.31 min, 95.8%. HRMS (ESI) m/z calcd for C$_{20}$H$_{22}$N$_2$O$_3$S [(M+Na)] 393.1212. found: 393.1231.

N-((2,2-Dimethyl-2H-pyrano[3,2-b]pyridin-6-yl)methyl)-N-phenylbutane-1-sulfonamide (26n). Yield: 48%. $^1$H NMR (CDCl$_3$): δ 7.41-7.29 (m, 4H), 7.27-7.22 (m, 1H), 7.18 (d, J=8.3 Hz, 1H), 7.00 (dd, J=12.4, 5.5 Hz, 1H), 6.41 (d, J=10.1 Hz, 1H), 5.86 (d, J=10.1 Hz, 1H), 4.94 (s, 2H), 3.38-2.79 (m, 2H), 1.96-1.77 (m, 2H), 1.54-1.38 (m, 8H), 1.12-0.77 ppm (m, 3H). $^{13}$C NMR (CDCl$_3$): δ 170.85, 148.78, 148.19, 139.60, 135.37, 129.28, 128.34, 127.62, 123.68, 123.62, 122.54, 56.25, 51.28, 28.22, 25.29, 21.68, 13.61 ppm. MS (ESI) m/z [(M+H)$^+$] 387. HPLC: ret. time=8.3 min, 95.8%.

N-((2,2-Dimethyl-2H-pyrano[3,2-b]pyridin-6-yl)methyl)-N-phenylpropane-1-sulfonamide (26o). Yield: 20%. $^1$H NMR (CDCl$_3$): δ 7.40-7.21 (m, 6H), 7.17 (d, J=8.3 Hz, 1H), 6.98 (t, J=7.2 Hz, 1H), 6.40 (d, J=10.1 Hz, 1H), 5.85 (d, J=10.1 Hz, 1H), 4.93 (s, 2H), 3.20-2.99 (m, 2H), 1.98-1.79 (m, 2H), 1.43 (s, 6H), 1.03 ppm (t, J=7.4 Hz, 3H). $^{13}$C NMR (CDCl$_3$): δ 148.78, 148.18, 139.59, 135.38, 129.28, 128.35, 127.62, 123.67, 123.63, 122.53, 77.34, 77.02, 76.70, 56.19, 53.17, 28.21, 17.08, 13.09 ppm. MS (ESI) m/z [(M+H)$^+$] 373. HPLC: ret. time=9.23 min, 97.4%.

N-((2,2-Dimethyl-2H-pyrano[3,2-b]pyridin-6-yl)methyl)-2-methyl-N-phenylpropane-1-sulfonamide (26p). Yield: 28%. $^1$H NMR (CDCl$_3$): δ 7.40-7.30 (m, 4H), 7.27-7.21 (m, 1H), 7.19 (d, J=8.3 Hz, 1H), 6.99 (d, J=8.3 Hz, 1H), 6.42 (d, J=10.1 Hz, 1H), 5.89 (dd, J=21.3, 10.0 Hz, 1H), 4.93 (s, 2H), 3.01 (dd, J=14.1, 6.5 Hz, 2H), 2.34 (dd J=13.3, 6.7 Hz, 1H), 1.47 (d, J=14.5 Hz, 6H), 1.10 ppm (d, J=6.7 Hz, 6H). MS (ESI) m/z [(M+H)$^+$] 387. HPLC: ret. time=10.4 min, 96.3%.

N-((2,2-Dimethyl-2H-pyrano[3,2-b]pyridin-6-yl)methyl)-N-phenylbiphenyl-4-sulfonamide (26q). Yield: 17%. $^1$H NMR (CDCl$_3$): δ 7.69 (s, 4H), 7.67-7.60 (m, 2H), 7.57-7.41 (m, 3H), 7.36-7.22 (m, 5H), 7.21-7.13 (m, 2H), 7.00 (t, J=7.3 Hz, 1H), 6.34 (d, J=10.1 Hz, 1H), 5.83 (t, J=9.5 Hz, 1H), 4.86 (d, J=5.9 Hz, 2H), 1.43 ppm (s, 6H). HRMS (ESI) m/z calcd for C$_{29}$H$_{27}$N$_2$O$_3$S [(M+H)$^+$] 483.1742. found: 483.1723. HPLC: ret. time=16.6 min, 96.1%.

N-((2,2-Dimethyl-2H-pyrano[3,2-b]pyridin-6-yl)methyl)-N-phenylbenzo[d][1,3]dioxole-4-sulfonamide (26r). Yield: 65%. $^1$H NMR (CDCl$_3$): δ 7.35-7.21 (m, 4H), 7.21-7.12 (m, 3H), 7.08 (t, J=3.9 Hz, 1H), 7.02-6.93 (m, 1H), 6.88-6.78 (m, 1H), 6.36 (dd, J=10.1, 0.5 Hz, 1H), 6.09 (s, 2H), 5.84 (dd, J=14.0, 9.0 Hz, 1H), 4.82 (s, 2H), 1.68 (s, 2H), 1.43 ppm (s, 6H). HRMS (ESI) m/z calcd for C$_{24}$H$_{23}$N$_2$O$_5$S [(M+H)$^+$] 451.1328. found: 451.1316. HPLC, ret. time=10.7 min, 99.7%.

N-((2,2-Dimethyl-2H-pyrano[3,2-b]pyridin-6-yl)methyl)-N-phenylquinoline-8-sulfonamide (26s). Yield: 65%. $^1$H NMR (CDCl$_3$): δ 9.19 (dd, J=4.2, 1.8 Hz, 1H), 8.43-8.16 (m, 2H), 8.00 (dt, J=10.5, 5.3 Hz, 1H), 7.66-7.56 (m, 2H), 7.54-7.47 (m, 1H), 7.14-6.94 (m, 6H), 6.40 (d, J=10.1 Hz, 1H), 5.85 (t, J=15.1 Hz, 1H), 5.58 (d, J=35.1 Hz, 2H), 1.45 ppm (s, 6H). $^{13}$C NMR (CDCl$_3$): δ 151.3, 150.0, 148.5, 144.2, 140.1, 139.6, 137.1, 136.5, 135.1, 133.7, 133.5, 128.8, 128.8, 128.2, 127.2, 125.4, 123.9, 123.8, 122.4, 122.1, 77.4, 77.1, 76.9, 76.7, 58.8, 28.2 ppm. HRMS (ESI) m/z calcd for C$_{26}$H$_{24}$N$_3$O$_3$S [(M+H)$^+$] 485.1538. found: 485.1543. HPLC: ret. time=10.0 min, 96.9%.

N-((2,2-dimethyl-2H-pyrano[3,2-b]pyridin-6-yl)methyl)-N-phenyl-2,3-dihydrobenzo[b][1,4]dioxine-6-sulfonamide (26t). Yield: 57%. $^1$H NMR (CDCl$_3$); δ 1.419 (s, 6H), 4.33-4.28 (m, 2H), 4.81 (s, 2H), 5.82 (d, 1H, J=10), 6.35 (d, 1H, J=10), 6.89 (d, 1H, J=8.4), 6.97 (d, 1H, J=8.4), 7.06 (dd, 1H), 7.12-7.15 (m, 2H), 7.20-7.30 ppm (m, 5H). $^{13}$C NMR (CDCl$_3$): δ 148.6, 147.7, 147.5, 143.4, 140.2, 139.4, 135.2, 130.4, 128.8, 128.5, 127.6, 123.7, 123.6, 122.4, 121.6, 117.4, 117.4, 77.4, 77.1, 77.0, 76.7, 64.6, 64.1, 60.4, 55.7, 28.2, 21.1, 14.2 ppm. HRMS (ESI) m/z calcd for C$_{15}$H$_{15}$N$_2$O$_5$S [(M+H)$^+$] 465.1484. found: 465.1489. HPLC: ret. time=10.9 min, 98.2%.

N-((2,2-Dimethyl-2H-pyrano[3,2-b]pyridin-6-yl)methyl)-3,4-dimethoxy-N-phenylbenzamide (27). To a solution of 25a (60 mg, 0.226 mmol) in DCM (3 mL) was added triethylamine (0.06 mL, 0.452 mmol) and 3,4-dimethoxybenzoyl chloride (54 mg, 0.271 mmol). The reaction was stirred overnight at room temperature. The reaction mixture was washed with dH2O (×2) and sat. NaHCO$_3$ (×2), dried over MgSO4 and concentrated in vacuo. Purification by column: silica gel: 3:1 DCM/EtOAc gave a quantitative yield of a light yellow oil. $^1$H NMR (CDCl$_3$): δ 7.26-7.17 (m, 3H), 7.17-7.08 (m, 3H), 7.06-6.97 (m, 2H), 6.95 (t, J=5.0 Hz, 1H), 6.66 (d, J=8.4 Hz, 1H), 6.53-6.40 (m, 1H), 5.92-5.79 (m, 1H), 5.16 (s, 2H), 3.83 (s, 3H), 3.66 (s, 3H), 1.46 ppm (s, 6H). $^{13}$C NMR (CDCl$_3$): δ 169.9, 150.3, 149.0, 148.6, 147.9, 144.7, 140.6, 135.1, 129.0, 127.8, 127.2, 126.3, 124.0, 123.6, 123.0, 122.3, 112.6, 109.9, 77.4, 77.0, 77.0, 76.7, 55.8, 55.7, 55.6, 28.2 ppm. HRMS (ESI) m/z calcd for C$_{26}$H$_{27}$N$_2$O$_4$ [(M+H)$^+$] 431.1971. found: 431.1951.

2-Bromo-6-(hydroxymethyl)pyridin-3-ol (30). A solution of 2-bromo-3-hydroxy-6-methylpyridine 1-oxide 29 (15 g, 0.075 mol) in TFAA (50 mL, 0.375 mol) and was stirred at 40° C. for 24 h. The solvent was removed under vacuum. The residue was purified by column chromatography (silica gel: EA:Hex, 2:1). Yield: 4.5 g, 30%. $^1$H NMR (CDCl$_3$): δ 7.32 (d, J=8.0 Hz, 1H), 7.25 (d, J=8.5 Hz, 1H), 4.56 (s, 2H).

(6-Bromo-5-(2-methylbut-3-yn-2-yloxy)pyridin-2-yl)methanol (31). Compound 30 was dissolved in acetone (20 mL) and then K$_2$CO$_3$ (166 mg, 7 mmol), KI (33.2 mg, 0.2 mmol), and CuCl$_2$.2H$_2$O (33.2 mg, 0.02 mmol) were added. The suspension was stirred at 60° C. for 10 min. The solution of 3-chloro-3-methyl-2-butyne (1.02 g, 5 mmol) in acetone (5 mL) was added dropwise to the solution of 30. The reaction mixture was cooled to room temperature and the suspension filtered. The solid residue was washed with MeOH. The filtrate was concentrated under vacuum and purified with column chromatography (silica gel, EA: hexane, 1:1). Yield: 700 mg, 57%. $^1$H NMR (CDCl$_3$): δ 7.88 (d, J=8.0 Hz, 1H), 7.23

(d, J=8.0 Hz, 1H), 4.72 (s, 2H), 1.73 ppm (s, 6H). $^{13}$C NMR (CDCl$_3$): δ 154.7, 149.6, 137.03, 129.5, 120.4, 85.7, 75.8, 75.7, 64.6, 30.1 ppm.

(8-Bromo-2,2-dimethyl-2H-pyrano[2,3-c]pyridin-6-yl)methanol (32). A solution of 31 (700 mg, 2.5 mmol) in toluene (10 mL) was subjected to microwave irradiation (200 W, 120° C.) for 1 h. The reaction mixture was cooled to room temperature and filtered. The filtrate was concentrated under vacuum and the residue purified by column chromatography (silica gel, EA:Hex 1:3-1:2). Yield: 500 mg, 70%. $^1$H NMR (CDCl$_3$): δ 6.88 (s, 1H), 6.28 (d, J=10 Hz, 1H), 5.90 (d, J=9.6 Hz, 1H), 4.63 (s, 2H), 1.51 ppm (s, 6H).

8-Bromo-6-(bromomethyl)-2,2-dimethyl-2H-pyrano[2,3-c]pyridine (33). To a solution of 32 in DCM (2 mL) was added CBr$_4$ (66 mg, 0.2 mmol) and PPh$_3$ (264 mg, 0.2 mmol). The reaction mixture was stirred at room temperature for 1 h. The solvent was removed under vacuum and the residue purified by column chromatography (silica gel, EA:Hex, 1:4). Yield: 260 mg, 40%. $^1$H NMR (CDCl$_3$): δ 6.28 (d, J=10 Hz, 1H), 5.91 (d, J=10 Hz, 1H), 4.47 (s, 2H), 1.53 ppm (s, 6H).

General Procedure for the Synthesis of 34.

To a degassed flask with 33 (1 eq) was added DMF, aniline (1.5 eq) and DIEA (1.5 eq). The mixture was stirred at room temperature overnight. Water (50 mL) was added to the reaction mixture and the resulting solution was extracted with ethyl acetate (3×25 ml). The combined organic layers was washed with 0.5 N HCl (50 mL), 40% NaHCO$_3$ (50 mL), water (50 mL) and brine, dried over Na$_2$SO$_4$ and concentrated under vacuum. The residue was purified by column chromatography (silica gel).

N-((8-bromo-2,2-dimethyl-2H-pyrano[2,3-c]pyridin-6-yl)methyl)benzenamine 34a. Yield: 78%. $^1$H NMR (CDCl$_3$): δ 7.26-7.21 (m, 3H), 6.97-6.95 (m, 3H), 6.23 (d, J=9.6 Hz, 1H), 5.85 (d, J=9.6 Hz, 1H), 4.40 (s, 2H), 1.48 ppm (s, 6H).

N-((8-Bromo-2,2-dimethyl-2H-pyrano[2,3-c]pyridin-6-yl)methyl)cyclohexanamine (34b). Yield: 60%. $^{13}$C NMR (CD$_3$OD): δ 152.0, 145.2, 136.9, 129.7, 129.1, 119.8, 118.7, 78.5, 56.0, 49.8, 32.4, 26.8, 25.8, 24.7 ppm.

General Procedure for the Synthesis of Compound 35.

A flask of secondary amine 34 (1 equiv.) was degassed and THF (anhydrous) was added under nitrogen. The solution was cooled to −78° C. and stirred for 1 h. BuLi (2.5 equiv.) was the added to the solution dropwise at −78° C. The resulting solution was stirred for 1 h. Water (10 mL) was added to the solution, which was diluted with ethyl acetate (25 mL). After separation, the aqueous layer was extracted with ethyl acetate and washed with water (25 ml×3) and brine (25 mL), dried over Na$_2$SO$_4$ and concentrated under vacuum. The residue was purified by column chromatography (silica gel, EA: Hex, 1:4)

N-((2,2-Dimethyl-2H-pyrano[2,3-c]pyridin-6-yl)methyl)benzenamine (35a). Yield: 70%. $^1$H NMR (CD$_3$OD): δ 7.91 (s, 1H), 7.08-7.04 (m, 3H), 6.59-6.57 (m, 3H), 6.28 (d, J=9.6 Hz, 1H), 5.92 (s, J=10 Hz, 1H), 4.88 (s, 2H), 1.41 ppm (s, 6H). $^{13}$C NMR (CD$_3$OD): δ 152.3, 148.3, 148.2, 136.7, 135.2, 128.9, 128.7, 119.9, 117.8, 116.8, 112.6, 76.9, 26.8 ppm.

N-((2,2-Dimethyl-2H-pyrano[2,3-c]pyridin-6-yl)methyl)cyclohexanamine (35b). Yield: 50%. $^1$H NMR (CD$_3$OD): δ 7.95 (s, 1H), 7.08 (s, 1H), 6.44 (d, J=9.6 Hz, 1H), 6.03 (d, J=10 Hz, 1H), 3.78 (s, 2H), 2.46 (m, 1H), 1.97-1.75 (m, 5H), 1.46 (s, 6H), 1.27-1.16 ppm (m, 5H). $^{13}$C NMR (CD$_3$OD): δ 151.5, 148.3, 136.7, 136.5, 128.7, 119.9, 119.0, 77.00, 56.0, 50.3, 32.4, 26.8, 25.8, 24.7 ppm.

General Procedure for Synthesis of 36.

A mixture of compound 35 (1 equiv.) and the appropriate sulfonyl chloride (2 equiv.) in pyridine was stirred overnight at room temperature. 1 M HCl was added to the reaction mixture and the solution extracted with ethyl acetate (3×15 mL). The combined organic layer was washed with water (3×20 mL), brine and dried over Na$_2$SO$_4$. The solvent was removed under vacuum and the residue purified by column chromatography: silica gel (EA: Hex; 1:4).

N-((2,2-Dimethyl-2H-pyrano[2,3-c]pyridin-6-yl)methyl)-4-methoxy-N-phenylbenzenesulfonamide (36a). Yield: 50%. $^1$H NMR (CD$_3$OD): δ 7.76 (s, 1H), 7.59-7.56 (m, 2H), 7.25-7.18 (m, 3H), 7.09-7.04 (m, 4H), 6.37 (d, J=10 Hz, 1H), 5.97 (d, J=10 Hz, 1H), 4.88 (s, 3H), 4.78 (s, 2H), 3.084 (s, 3H), 1.40 ppm (s, 6H). $^{13}$C NMR (CD$_3$OD): 163.5, 148.6, 139.3, 136.7, 136.1, 129.7, 129.3, 128.8, 128.5, 128.5, 127.6, 119.7, 119.4, 113.9, 77.1, 55.0, 54.9, 26.8 ppm. MS (ESI) m/z [(M+H)$^+$] 437. HPLC: ret. time=9.6 min, 97.8%.

N-((2,2-Dimethyl-2H-pyrano[2,3-c]pyridin-6-yl)methyl)-4-nitro-N-phenylbenzenesulfonamide (36b). Yield: 59%. $^1$H NMR (CD$_3$OD): δ 8.41 (dd, J=2.0 Hz, 4.8 Hz, 2H), 7.89 (dd, J=2.0 Hz, 4.8 Hz), 7.78 (s, 1H), 7.29-7.28 (m, 4H), 7.10-7.08 (m, 2H), 6.39 (d, J=10 Hz, 1H), 6.00 (d, J=10 Hz, 1H), 1.42 ppm (s, 6H). MS (ESI) m/z [(M+H)$^+$] 452. HPLC: ret. time=9.03 min, 95.2%.

N-Cyclohexyl-N-((2,2-dimethyl-2H-pyrano[2,3-c]pyridin-6-yl)methyl)-4-isopropylbenzenesulfonamide (36c). Yield: 28%. $^1$H NMR (CDCl$_3$): δ 7.98 (s, 1H), 7.77-7.75 (m, 2H), 7.37-7.34 (m, 1H), 7.28 (d, J=8.8 Hz, 1H), 6.34 (d, J=9.6 Hz, 1H), 5.84 (d, J=10 Hz, 1H), 4.42 (s, 2H), 3.80 (m, 1H), 2.99 (m, 1H), 1.75-1.59 (m, 3H), 1.55-1.39 (m, 9H), 1.29-1.27 (m, 6H), 1.23-1.19 ppm (m, 4H). $^{13}$C NMR (CDCl$_3$): δ 153.8, 151.8, 148.1, 138.7, 136.7, 135.8, 128.1, 127.1, 127.3, 120.9, 118.9, 58.5, 48.7, 34.1, 28.0, 26.1, 25.1, 23.7 ppm. MS (ESI) m/z [(M+H)$^+$] 455. HPLC: ret. time=18.6 min, 98.2%.

N-Cyclohexyl-N-((2,2-dimethyl-2H-pyrano[2,3-c]pyridin-6-yl)methyl)-3,4-dimethoxybenzenesulfonamide (36d). Yield: 28%. $^1$H NMR (CDCl$_3$) δ 8.00 (s, 1H), 7.50-7.47 (m, 1H), 7.33-7.29 (m, 2H), 6.94 (d, J=8.4 Hz, 1H), 6.36 (d, J=9.6 Hz, 1H), 5.86 (d, J=9.6 Hz, 1H), 5.32 (s, 2H), 3.967 (s, 3H), 3.94 (s, 3H), 3.97 (m, 1H), 1.68-1.52 (m, 4H), 1.48 (s, 6H), 1.28-1.20 ppm (m, 4H). $^{13}$C NMR (CDCl$_3$): δ 151.7, 149.1, 136.7, 135.9, 133.2, 128.1, 120.8, 120.7, 118.9, 110.6, 109.5, 83.1, 58.5, 56.2, 56.2, 48.6, 31.4, 28.0, 26.1, 25.1 ppm. MS (ESI) m/z [(M+H)$^+$] 473. HPLC: ret. time=10.3 min, 97.3%.

The invention claimed is:

1. A compound of Formula I

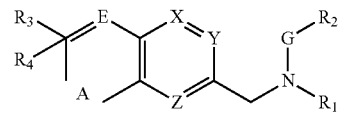

Formula I or salt, ester, or prodrug thereof wherein,

---- is a single bond;

A is —CR$^5$R$^6$—, —CR$^7$=CR$^8$—, or —CR$^7$R$^9$—CR$^8$R$^{10}$—;

E is O;

G is —SO$_2$—;

X is CR$^{12}$;

Y is CR$^{13}$;

Z is N;

R$^1$ is alkyl, carbocyclyl, aryl, or heterocyclyl, wherein R$^1$ is optionally substituted with one or more, the same or different, R$^{15}$;

R$^2$ is alkyl, carbocyclyl, aryl, or heterocyclyl, wherein R$^2$ is optionally substituted with one or more, the same or different, R$^{16}$;

$R^3$ is alkyl optionally substituted with one or more, the same or different, $R^{17}$;

$R^4$ is $R^4$ is alkyl optionally substituted with one or more, the same or different, $R^{18}$;

$R^5$, $R^6$, $R^7$, $R^8$, $R^9$, $R^{10}$, $R^{11}$, $R^{12}$, and $R^{13}$ are each individually and independently selected from hydrogen, alkyl, halogen, nitro, cyano, hydroxy, amino, mercapto, formyl, carboxy, carbamoyl, alkoxy, alkylthio, alkylamino, (alkyl)$_2$amino, alkylsulfinyl, alkylsulfonyl, arylsulfonyl, carbocyclyl, aryl, or heterocyclyl, optionally substituted with one or more, the same or different, $R^{19}$;

$R^{15}$, $R^{16}$, $R^{17}$, $R^{18}$, and $R^{19}$ are halogen, nitro, cyano, hydroxy, trifluoromethoxy, trifluoromethyl, amino, formyl, carboxy, carbamoyl, mercapto, sulfamoyl, methyl, ethyl, methoxy, ethoxy, acetyl, acetoxy, methylamino, ethylamino, dimethylamino, diethylamino, N-methyl-N-ethylamino, acetylamino, N-methylcarbamoyl, N-ethylcarbamoyl, N,N-dimethylcarbamoyl, N,N-diethylcarbamoyl, N-methyl-N-ethylcarbamoyl, methylthio, ethylthio, methylsulfinyl, ethylsulfinyl, mesyl, ethylsulfonyl, methoxycarbonyl, ethoxycarbonyl, N-methylsulfamoyl, N-ethylsulfamoyl, N,N-dimethylsulfamoyl, N,N-diethylsulfamoyl, N-methyl-N-ethylsulfamoyl, carbocyclyl, aryl, or heterocyclyl.

2. The compound of claim 1, wherein $R^1$ is a cyclopropyl, cyclobutyl or cyclopentyl.

3. The compound of claim 1, wherein $R^3$ and $R^4$ are alkyl.

4. The compound of claim 1, wherein $R^3$ is alkyl other than methyl.

5. The compound of claim 1, wherein $R^2$ is 4-methoxyphenyl, 3,4-dimethoxyphenyl, or 3,5-dimethylphenyl.

6. The compound of claim 1 selected from the group:
N-cyclopentyl-N-((2,2-dimethyl-2H-pyrano[3,2-b]pyridin-6-yl)methyl)-3,4-dimethoxybenzenesulfonamide;
N-cyclobutyl-N-((2,2-dimethyl-2H-pyrano[3,2-b]pyridin-6-yl)methyl)-3,4-dimethoxybenzenesulfonamide;
or salts thereof.

7. A pharmaceutical compositions comprising a compound as provided in claim 1 or pharmaceutically acceptable salt and a pharmaceutically acceptable excipient.

* * * * *